(12) United States Patent
Greig et al.

(10) Patent No.: US 9,050,329 B1
(45) Date of Patent: Jun. 9, 2015

(54) ARYL-PHENYL-SULFONAMIDO-CYCLOALKYL COMPOUNDS AND THEIR USE

(71) Applicant: PIMCO 2664 Limited, London (GB)

(72) Inventors: Iain Robert Greig, Aberdeen (GB); Rose Mary Sheridan, Northchurch (GB); Raymond Fisher, Chapel-en-le-Frith (GB); Matthew John Tozer, Chapel-en-le-Frith (GB); Juha Andrew Clase, Chapel-en-le-Frith (GB); Andrew Smith, Frodsham (GB); Andrew Robert Tuffnell, Liverpool (GB); Robert Jurgen Van 't Hof, Edinburgh (GB)

(73) Assignee: PIMCO 2664 Limited, London (GB)

( * ) Notice: Subject to any disclaimer, the term of this patent is extended or adjusted under 35 U.S.C. 154(b) by 0 days.

(21) Appl. No.: 14/464,973

(22) Filed: Aug. 21, 2014

Related U.S. Application Data

(63) Continuation of application No. 13/886,799, filed on May 3, 2013, now Pat. No. 8,822,507, which is a continuation of application No. 13/063,956, filed as application No. PCT/GB2009/002221 on Sep. 18, 2009, now Pat. No. 8,435,968.

(60) Provisional application No. 61/098,271, filed on Sep. 19, 2008.

(30) Foreign Application Priority Data

Sep. 19, 2008 (GB) .................................. 0817207.4

(51) Int. Cl.
| | |
|---|---|
| *C07C 311/20* | (2006.01) |
| *C07C 311/28* | (2006.01) |
| *C07D 213/52* | (2006.01) |
| *C07D 239/26* | (2006.01) |
| *C07D 239/30* | (2006.01) |
| *C07D 295/135* | (2006.01) |
| *A61K 31/18* | (2006.01) |
| *A61K 31/4418* | (2006.01) |

(52) U.S. Cl.
CPC .............. *A61K 31/4418* (2013.01); *A61K 31/18* (2013.01)

(58) Field of Classification Search
None
See application file for complete search history.

(56) References Cited

U.S. PATENT DOCUMENTS

| | | | |
|---|---|---|---|
| 4,119,784 A | 10/1978 | Conrow et al. | |
| 4,948,809 A | 8/1990 | Witte et al. | |
| 5,760,028 A | 6/1998 | Jadhav et al. | |
| 6,159,995 A | 12/2000 | Thorwart et al. | |
| 6,451,824 B1 | 9/2002 | Thorwart et al. | |
| 6,849,635 B2 | 2/2005 | Dhanak et al. | |
| 7,560,597 B2 | 7/2009 | Greig et al. | |
| 7,572,825 B2 | 8/2009 | Ralston et al. | |
| 7,598,289 B2 | 10/2009 | Ralston et al. | |
| 7,745,424 B2 | 6/2010 | Ralston et al. | |
| 7,964,643 B2 | 6/2011 | Ralston et al. | |
| 8,207,167 B2 | 6/2012 | Greig et al. | |
| 8,435,968 B2 | 5/2013 | Greig et al. | |
| 8,524,778 B2 | 9/2013 | Greig et al. | |
| 8,822,507 B2 | 9/2014 | Greig et al. | |
| 2003/0144292 A1 | 7/2003 | Natchus et al. | |
| 2005/0119305 A1 | 6/2005 | Naka et al. | |
| 2005/0227987 A1 | 10/2005 | Vicker et al. | |
| 2006/0030543 A1 | 2/2006 | Malecha et al. | |
| 2007/0191370 A1 | 8/2007 | Devasagayaraj et al. | |
| 2008/0119555 A1 | 5/2008 | Ralston et al. | |

(Continued)

FOREIGN PATENT DOCUMENTS

| | | |
|---|---|---|
| DE | 10 46 220 | 12/1958 |
| DE | 3000519 A1 | 8/1980 |

(Continued)

OTHER PUBLICATIONS

Annex to UK Search Report for GB 0705400.0—Jul. 9, 2007.

(Continued)

*Primary Examiner* — Kamal Saeed
(74) *Attorney, Agent, or Firm* — Swanson & Bratschun, L.L.C.

(57) ABSTRACT

The present invention pertains generally to the field of therapeutic compounds, and more specifically to certain aryl-phenyl-sulfonamido-cycloalkyl compounds of the following formula (collectively referred to herein as "APSAC compounds"). The present invention also pertains to pharmaceutical compositions comprising such compounds, and the use of such compounds and compositions, both in vitro and in vivo, in treatment, for example, of inflammation and/or joint destruction and/or bone loss; of disorders mediated by excessive and/or inappropriate and/or prolonged activation of the immune system; of inflammatory and autoimmune disorders, for example, rheumatoid arthritis, psoriasis, psoriatic arthritis, chronic obstructive pulmonary disease (COPD), atherosclerosis, inflammatory bowel disease, ankylosing spondylitis, and the like; of disorders associated with bone loss, such as bone loss associated with excessive osteoclast activity in rheumatoid arthritis, osteoporosis, cancer-associated bone disease, Paget's disease and the like, etc.; and of cancer, such as a haematological malignancy, a solid tumor, etc.

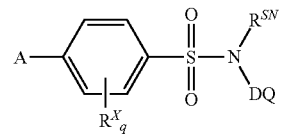

54 Claims, 4 Drawing Sheets

(56) References Cited

U.S. PATENT DOCUMENTS

| | | | |
|---|---|---|---|
| 2008/0255240 | A1 | 10/2008 | Christiansen et al. |
| 2010/0286266 | A1 | 11/2010 | Greig et al. |
| 2011/0172189 | A1 | 7/2011 | Greig et al. |
| 2011/0190302 | A1 | 8/2011 | Greig et al. |
| 2013/0245018 | A1 | 9/2013 | Greig et al. |

FOREIGN PATENT DOCUMENTS

| | | | |
|---|---|---|---|
| EP | 0877018 | A1 | 5/1998 |
| EP | 0 960 882 | | 12/1999 |
| EP | 0 877 019 | | 12/2001 |
| EP | 0 988 018 | | 3/2003 |
| EP | 1 431 267 | | 6/2004 |
| EP | 1 491 190 | | 12/2004 |
| EP | 1659113 | A1 | 5/2006 |
| GB | 597810 | | 2/1948 |
| JP | 11246527 | | 9/1999 |
| JP | 2001-504809 | | 4/2001 |
| WO | WO 96/37492 | | 11/1996 |
| WO | WO 97/16433 | | 5/1997 |
| WO | WO 97/33887 | | 9/1997 |
| WO | WO 98/03166 | | 1/1998 |
| WO | WO 98/16503 | | 4/1998 |
| WO | WO 98/23608 | | 6/1998 |
| WO | WO 98/43962 | | 10/1998 |
| WO | WO 98/50342 | | 11/1998 |
| WO | WO 99/37621 | | 7/1999 |
| WO | WO 99/42443 | | 8/1999 |
| WO | WO 99/59992 | A1 | 11/1999 |
| WO | WO 01/16137 | | 3/2001 |
| WO | WO 01/90077 | | 11/2001 |
| WO | WO 02/060867 | | 8/2002 |
| WO | WO 02/074298 | | 9/2002 |
| WO | WO 03/037321 | | 5/2003 |
| WO | WO 2004/022561 | | 3/2004 |
| WO | WO 2004/039784 | | 5/2004 |
| WO | WO 2004/073619 | | 9/2004 |
| WO | WO 2004/098582 | | 11/2004 |
| WO | WO 2004/106290 | A1 | 12/2004 |
| WO | WO 2005/060963 | A1 | 7/2005 |
| WO | WO 2005/080367 | | 9/2005 |
| WO | WO 2005/085189 | A2 | 9/2005 |
| WO | WO 2005/105712 | A1 | 11/2005 |
| WO | WO 2005/118528 | | 12/2005 |
| WO | WO 2006/134467 | A1 | 12/2006 |
| WO | WO 2007/008541 | A2 | 1/2007 |
| WO | WO 2007/026962 | A1 | 3/2007 |
| WO | WO 2008/114022 | | 9/2008 |
| WO | WO 2010/032009 | A1 | 3/2010 |
| WO | WO 2010/032010 | A1 | 3/2010 |

OTHER PUBLICATIONS

Argus et al., 1958, "Distribution studies with sulphur 35-labelled disulfonamides in tumor-bearing and tumor-free mice", Brit. J. Cancer, vol. 12, pp. 636-644.
Armour K.J., et al., 2001, "Inhibition of bone resorption in vitro and prevention of ovariectomy-induced bone loss in vivo by flurbiprofen nitroxybutylester (HCT1026)," Arthritis and Rheumatism, vol. 44, No. 9, pp. 2185-2192.
Augstein, J., et al., 1965, "Some cardiovascular effects of a series of aryloxyalkylamines 1", J. Med. Chem., vol. 8, pp. 356-367.
Baud et al., 1999, "Signaling by proinflammatory cytokines: oligomerization of TRAF2 and TRAF6 is sufficient for JNK and IKK activation and target gene induction via an amino-terminal effector domain", Genes Dev., vol. 13, pp. 1297-1308.
Baud et al., 2009, "Is NFκB a good target for cancer therapy? Hopes and pitfalls", Nat. Rev. Drug Disc., vol. 8, pp. 33-40.
Brennan et al., 1989, "Inhibitory effect of TNF alpha antibodies on synovial cell interleukin-1 production in rheumatoid arthritis", Lancet, vol. 2, pp. 244-247.

Brennan et al., 1992, "Enhanced expression of tumor necrosis factor receptor mRNA and protein in mononuclear cells isolated from rheumatoid arthritis synovial joints", Eur. J. Immunol., vol. 22, pp. 1907-1912.
Brennan et al., 1996, "Cytokines in autoimmunity", Curr. Opin. Immunol., vol. 8, pp. 872-877.
Chemcats record for Enamine Screening Library, Enamine, Kiev, Ukraine, publication date Jan. 17, 2008, CAS Registry No. 950020-41-4 (2 pages).
Chemcats record for LaboTest Stock Catalog, LaboTest, Niederschoena, Germany, publication date Jul. 24, 2007, CAS Registry No. 331653-75-9 (2 pages).
Chemcats record for Ryan Scientific Screening Library, Ryan Scientific, Inc., Mt. Pleasant, SC, USA, publication date Jan. 25, 2008, CAS Registry No. 302603-86-7 (2 pages).
Chemcats record for Scientific Exchange Product List, Scientific Exchange, Inc., Centre Ossipee, NH, USA, publication date Jan. 30, 2008, CAS Registry No. 312756-83-5 (2 pages).
Chemcats records for Nanosyn Compound Library, Nanosyn Combinatorial Synthesis Inc., Menlo Park, CA, USA, publication date Apr. 17, 2007, CAS Registry Nos. 313495-94-2, 313521-07-2 (3 pages).
Chemcats records for Spectrum Info Catalog, Spectrum Info Ltd., Kiev, Ukraine, publication date Sep. 5, 2007: CAS Registry No. 885269-21-6, 885269-32-9, 885269-42-1, 885269-85-2, 885269-88-5, 885269-91-0 (7 pages).
Corey EJ, Shibata S, Bakshi RK, 1988, "An effcicient and catalytically enantioselective route to (S)-(-)-Phenyloxirane," J. Org. Chem., vol. 53, pp. 2861-2863.
Coxon, F.P., et al., 2000, "Protein geranylgeranylation is required for osteoclast formation, function, and survival: inhibition by bisphosphonates and GGTI-298," J.Bone Miner.Res., vol. 15, pp. 1467-1476.
Degenhardt, C.R., et al., 1986, "Synthesis of Ethenylidenebis(phosphonic acid) and its Tetraalkyl Esters," J. Org. Chem., vol. 51, pp. 3488-3490.
Eberhard, A., et al., 1965, "Hydrolysis of Phostonates," J. Amer. Chem. Soc., vol. 87, pp. 253-260.
Elliott et al., 1994, "Randomised double-blind comparison of chimeric monoclonal antibody to tumour necrosis factor alpha (cA2) versus placebo in rheumatoid arthritis", Lancet, vol. 344, pp. 1105-1110.
Feldmann et al., 1994, "TNF alpha as a therapeutic target in rheumatoid arthritis," Circ. Shock, vol. 43, pp. 179-184.
Feldmann et al., 1996, "Rheumatoid arthritis", Cell, vol. 85, pp. 307-310.
Feldmann et al., 2001, "The role of TNF alpha and IL-1 in rheumatoid arthritis," Curr. Dir. Autoimmun., vol. 3, pp. 188-199.
Firestein et al., 1999, "Signal transduction and transcription factors in rheumatic disease", Arthritis Rheum., vol. 42, pp. 609-621.
Firestein, 1996, "Invasive fibroblast-like synoviocytes in rheumatoid arthritis. Passive responders or transformed aggressors?", Arthritis Rheum., vol. 39, pp. 1781-1790.
Firestein, 2005 "Immunologic mechanisms in the pathogenesis of rheumatoid arthritis", J. Clin. Rheumatol., vol. 11. pp. S39-S44.
Gottlieb, 2005, "Psoriasis: Emerging Therapeutic Strategies", Nat. Rev. Drug Disc., vol. 4, pp. 19-34.
Greig et al., 2006, "Development and characterization of biphenylsulfonamides as novel inhibitors of bone resorption", J. Med. Chem., vol. 49: pp. 7487-7492.
Ha-Duong, N-T, et al, 2001, "Synthesis of sulfaphenazole derivatives and their use as inhibitors and tools for comparing the active sites of human liver cytochromes P450 of the 2C subfamily", J. Med. Chem., vol. 44, pp. 3622-3631.
Herczegh, P., et al, 2002, "Osteoadsorptive Bisphosphonate Derivatives of Fluoroquinolone Antibacterials," J. Med. Chem., vol. 45, pp. 2338-2341.
Hughes, D.E., et al., 1997, "Apoptosis in bone physiology and disease," J. Clin. Pathol.: Molecular Pathology, vol. 50, pp. 132-137.
International Preliminary Report on Patentability (IPRP) for PCT/GB2005/002043 issued Dec. 4, 2006.
International Preliminary Report on Patentability (IPRP) for PCT/GB2008/000989 issued Sep. 22, 2009.

(56) References Cited

OTHER PUBLICATIONS

International Preliminary Report on Patentability (IPRP) for PCT/GB2009/002221 issued Mar. 22, 2011.
International Preliminary Report on Patentability (IPRP) for PCT/GB2009/002223 issued Mar. 22, 2011.
International Search Report (ISR) and Written Opinion of International Searching Authority (WOISA) for PCT/GB2005/002043 mailed Nov. 16, 2005.
International Search Report (ISR) and Written Opinion of International Searching Authority (WOISA) for PCT/GB2008/000989 mailed Jul. 22, 2008.
International Search Report (ISR) and Written Opinion of International Searching Authority (WOISA) for PCT/GB2009/002221 mailed Jan. 18, 2010.
International Search Report (ISR) and Written Opinion of International Searching Authority (WOISA) for PCT/GB2009/002223 mailed Feb. 9, 2010.
Jimi et al., 2004, "Selective inhibition of NF-kappa B blocks osteoclastogenesis and prevents inflammatory bone destruction in vivo", Nat. Med., vol. 10, pp. 617-624.
Joosten et al., 1996, "Anticytokine treatment of established type II collagen-induced arthritis in DBA/1 mice. A comparative study using anti-TNF alpha, anti-IL-1 alpha/beta, and IL-1Ra," Arthritis Rheum., vol. 39, pp. 797-809.
Klareskog et al., 2006, "A long-term, open-label trial of the safety and efficacy of etanercept (Enbrel) in patients with rheumatoid arthritis not treated with other disease-modifying antirheumatic drugs", Ann. Rheum. Dis., vol. 65, pp. 1578-1584.
Klareskog et al., 2006, "Mechanisms of disease: Genetic susceptibility and environmental triggers in the development of rheumatoid arthritis," Nat. Clin. Pract. Rheumatol., vol. 2, pp. 425-433.
Kong, Y.Y., et al., 1999, "OPGL is a key regulator of osteoclastogenesis, lymphocyte development and lymph-node organogenesis," Nature, vol. 397, pp. 315-323.
Korzenik et al., 2006, "Evolving knowledge and therpy of inflammatory bowel disease," Nat. Rev. Drug Disc., vol. 5, pp. 197-209.
Li et al., 2008, "A tumor necrosis factor-[alpha]-mediated pathway promoting autosomal dominant polycystic kidney disease", Nature Medicine, vol. 14(8), pp. 863-868.
Liu, 2005, "Molecular mechanism of TNF signaling and beyond," Cell Res., vol. 15(1), pp. 24-27.
Luckman et al.. 1998, "Heterocycle-containing bisphosphonates cause apoptosis and inhibit bone resorption by preventing protein prenylation: evidence from structure-activity relationships in J774 macrophages," J. Bone Miner. Res., vol. 13, pp. 1668-1678.
MacPherson, H; et al., 1999, "Expression and functional role of nitric oxide synthase isoforms in human osteoblast-like cells," Bone, vol. 24, pp. 179-185.
Mantovani, 2009, "Inflaming metastasis", Nature, vol. 457, pp. 36-37.
McInnes et al., 2005, "Targeting cytokines beyond tumor necrosis factor-alpha and interleukin-1 in rheumatoid arthritis", Curr. Pain Headache Rep., vol. 9, pp. 405-411.
Mohan et al., 1993, "Structure-Activity Relationship Studies with Symmetric Naphthalenesulfonic Acid Derivatives. Synthesis and Influence of Spacer and Naphthalenesulfonic Acid Moiety on Anti-HIV-1 Activity", J. Med. Chem., vol. 36, pp. 1996-2003.
Mount et al., 2005, "Rheumatoid arthritis market", Nat. Rev. Drug Disc., vol. 2, pp. 11-12.
Mundy, G.R., 1996, "Chapter 1: Bone Remodeling", in Bone Remodeling and its disorders (2nd edition), London, (Ed. Martin Dunitz), pp. 1-11.
Nociari et al., 1998, "A Novel one-step, highly sensitive fluorimetric assay to evaluate cell-mediated cytotoxicity", Journal of Immunological Methods, vol. 213, pp. 157-167.
Nyormoi, O., et al., 2003, "An MMP-2/MMP-9 inhibitor, 5a, enhances apoptosis induced by ligands of the TNF receptor superfamily in cancer cells", Cell Death and Differentiation, vol. 10, pp. 558-569.
O'Brien et al., 2000, "Structure-activity relationships and pharmacokinetic analysis for a series of potent, systemically available biphenylsulfonamide matrix metalloproteinase inhibitors". J. Med. Chem. vol. 43: pp. 156-166.
Peyman, A., et al., 2001, "αvβ3 antagonists based on a central thiophene scaffold", Bio. & Med. Chem. Letters, Vo. 11, pp. 2011-2015.
Philchenkov et al., 2004, "Caspases and cancer: mechanisms of inactivation and new treatment modalities", Exp. Oncol., vol. 26(2), pp. 82-97.
Raisz, L.G., 1988, "Local and systemic factors in the pathogenesis of osteoporosis," N. Engl. J. Med., vol. 318, pp. 818-828.
Ralston, S.H., 1997, "Science, Medicine and the Future: Osteoporosis," Br. Med. J., vol. 315, pp. 469-472.
Ramachandran PV, Gong B, Brown HC, 1995, "Chiral synthesis via organoboranes", J. Org. Chem., vol. 60, pp. 41-46.
Rodan, G.A., et al., 1997, "The missing bone," Cell, vol. 89, pp. 677-680.
Roodman, 2006, "Regulation of osteoclast differentiation", Ann. N. Y. Acad. Sci. , vol. 1068, pp. 100-109.
Smolen et al., 2003, "Therapeutic Strategies for Rheumatoid Arthritis", Nat. Rev. Drug Disc. , vol. 2, pp. 473-488.
Takahashi, N.; et al., 1988, "Osteoblastic cells are involved in osteoclast formation," Endocrinology, vol. 123, pp. 2600-2602.
Takasuka, M., et al., 1991, "FTIR spectral study of intramolecular hydrogen bonding in thromboxane A2 receptor antagonist S-145 and related compounds. 3. Conformation and activity of S-145 analogues", J. Med. Chem., vol. 34, pp. 1885-1891.
Tanaka et al., 2003, Signal transduction pathways regulating osteoclast differentiation and function, J. Bone Miner. Metab., vol. 21, pp. 123-133.
UK Search Report for GB 0412553.0 dated Sep. 30, 2004.
UK Search Report for GB 0817207.4 dated Jan. 7, 2009.
UK Search Report for GB 0817208.2 dated Jan. 8, 2009.
UK Search Report for GB 705400.0 dated Jul. 6, 2007.
van den Berg et al., 1999, "Pathogenesis of joint damage in rheumatoid arthritis: evidence of a dominant role for interleukin-I", Baillieres Best Pract. Res. Clin. Rheumatol., vol. 13(4), pp. 577-597.
van den Berg, 2002, "Is there a rationale for combined TNF and IL-1 blocking in arthritis?", Clin. Exp. Rheumatol. , vol. 20, pp. S21-S25.
van't Hof, R.J., et a;., 1997, "Cytokine-induced nitric oxide inhibits bone resorption by inducing apoptosis of osteoclast progenitors and suppressing osteoclast activity," J. Bone & Miner. Res., vol. 12(11), pp. 1797-1804.
Weissmann, 2006, "The pathogenesis of rheumatoid arthritis," Bull. Hosp. Jt. Dis., vol. 64, pp. 12-15.
Yasuda, H., et al, 1998, "Identity of osteoclastogenesis inhibitory factor (OCIF) and osteoprotegerin (OPG): a mechanism by which OPG/OCIF inhibits osteoclastogenesis in vitro", Endocrinology, vol. 139(3), pp. 1329-1337.
Ziff, 1990, "Rheumatoid arthritis—it's present and future", J. Rheumatol., vol. 17, pp. 127-133.

(a) TNFα alone

(b) TNFα + 10 µM ABD599

(c) TNFα + 10 µM ABD781

ARYL-PHENYL-SULFONAMIDO-CYCLOALKYL COMPOUNDS AND THEIR USE

RELATED APPLICATIONS

This application is a continuation of U.S. application Ser. No. 13/886,799, filed May 3, 2013, now U.S. Pat. No. 8,822,507. U.S. application Ser. No. 13/886,799 is a continuation of U.S. application Ser. No. 13/063,956, filed Mar. 15, 2011, U.S. Pat. No. 8,435,968. U.S. application Ser. No. 13/063,956 is a 35 U.S.C. §371 national phase application of PCT/GB2009/002221, filed Sep. 18, 2009 (WO 2010/032009), entitled "Aryl-Phenyl-Sulfonamido-Cycloalkyl Compounds and Their Use". PCT/GB2009/002221 is a non-provisional application of U.S. provisional patent application No. 61/098,271 filed Sep. 19, 2008 and United Kingdom patent application number 0817207.4 filed Sep. 19, 2008. The contents of each of these applications are incorporated herein by reference in their entirety.

TECHNICAL FIELD

The present invention pertains generally to the field of therapeutic compounds, and more specifically to certain aryl-phenyl-sulfonamido-cycloalkyl compounds (collectively referred to herein as "APSAC compounds"). The present invention also pertains to pharmaceutical compositions comprising such compounds, and the use of such compounds and compositions, both in vitro and in vivo, in treatment, for example, of inflammation and/or joint destruction and/or bone loss; of disorders mediated by excessive and/or inappropriate and/or prolonged activation of the immune system; of inflammatory and autoimmune disorders, for example, rheumatoid arthritis, psoriasis, psoriatic arthritis, chronic obstructive pulmonary disease (COPD), atherosclerosis, inflammatory bowel disease, ankylosing spondylitis, and the like; of disorders associated with bone loss, such as bone loss associated with excessive osteoclast activity in rheumatoid arthritis, osteoporosis, cancer-associated bone disease, Paget's disease and the like, etc.; and of cancer, such as a haematological malignancy, a solid tumour, etc.

BACKGROUND

A number of patents and publications are cited herein in order to more fully describe and disclose the invention and the state of the art to which the invention pertains. Each of these references is incorporated herein by reference in its entirety into the present disclosure, to the same extent as if each individual reference was specifically and individually indicated to be incorporated by reference.

Throughout this specification, including the claims which follow, unless the context requires otherwise, the word "comprise," and variations such as "comprises" and "comprising," will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Thus, for example, reference to "a pharmaceutical carrier" includes mixtures of two or more such carriers, and the like.

Ranges are often expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment.

This disclosure includes information that may be useful in understanding the present invention. It is not an admission that any of the information provided herein is prior art or relevant to the presently claimed invention, or that any publication specifically or implicitly referenced is prior art.

Rheumatoid Arthritis

Rheumatoid arthritis (RA) is a chronic inflammatory disease characterised by painful swelling, stiffness, loss of movement and the destruction of cartilage and bone. RA is characterised by an inflammation of the synovial lining of multiple joints and commonly affects the joints of the wrist and hands and may also affect the elbows, shoulders, hips, neck and knees; the ultimate hallmark of RA is joint destruction. RA is a common disease, estimated to affect up to 1% of adults in the developed world, with women more than twice as likely to be affected and over 30% of patients likely to become severely disabled within 20 years (see, e.g., Feldmann et al., 2006). RA is one of the most important causes of disability in the western world and is associated with a significant reduction in quality of life as well as increased mortality if left untreated. The disease can start at any age, with individuals aged between 40 and 70 most commonly affected.

The exact cause of RA remains unclear, but is highly complex and may involve the combination of a number of factors which lead to the development of autoantibodies, formation of immune complexes, production of pro-inflammatory cytokines, angiogenesis and eventual bone and cartilage loss (see, e.g., Klareskog et al, 2006; Ziff et al, 1990; Weissmann et al, 2006; Firestein et al, 2005). These factors include an abnormal immune response caused by reduced self tolerance or a biological trigger such as reaction to environmental factors, infectious agents, or hormonal stimulus (see, e.g., Klareskog et al, 2006); antibodies to the Fc fragment of IgG, known as rheumatoid factor, are present in 60-80% of adults with RA (see, e.g., Weissmann et al, 2006) but it is not known whether this factor is responsible for initiating the inflammatory cascade or is generated at a later stage and propagates the process (see, e.g., Weissmann et al, 2006); there is also a notable genetic predisposition to the disease, as shown by the presence of HLA-DR4 antibody in 70% of patients (see, e.g., Klareskog et al, 2006).

At the cellular level, development of RA usually commences with T-cells infiltrating the synovial membrane lining the affected joint; this then leads to the activation of macrophages, monocytes and synovial fibroblasts (see, e.g., Firestein, 1996) by way of cell-cell contact and release of various cytokines, including TNFα and IL-1 (see, e.g., Feldmann, 1996). Activation of these cells leads to the overproduction of a range of pro-inflammatory cytokines, of which the most important are TNFα, IL-1 and IL-6 (see, e.g., Brennan et al, 1996; McInnes et al, 2005). These pro-inflammatory cytokines are then instrumental in orchestrating several complex signal transduction cascades, including the NFκB, MAPK and Jak/STAT pathways (see, e.g., Firestein et al, 1999) which lead to the induction of genes coding for various products that propagate the inflammatory response and also promote tissue destruction. These products include tissue-degrading enzymes such as collagenases, matrix metalloproteases, cathepsins, and other pro-inflammatory factors such as selectins, integrins, leukotrienes, prostaglandins, chemokines, and other cytokines. Furthermore, TNFα and IL-1 also induce RANKL expression.

RANKL is an essential factor for the generation of osteoclasts (see, e.g., Tanaka et al, 2003; Roodman, 2006), and upregulated RANKL-production leads to increased osteoclast differentiation and ultimately bone destruction (see, e.g., Tanaka et al, 2003; Roodman, 2006). The inflammatory response leads to the accumulation of many leukocytes and immune factor populations within the affected joint and also to hyperplasia of the Type-A and Type-B synoviocytes (see, e.g., Firestein et al, 2005), leading to thickening and vascularisation of the synovium into a destructive and aggressive tissue known as a pannus. The pannus contains both osteoclasts, which destroy bone, and metalloproteases, which continue the destruction of cartilage.

Treatment of Rheumatoid Arthritis

Early therapies for RA focussed on controlling the symptoms of the disease, mainly by reduction of inflammation, rather than retarding disease progression. These drugs included NSAIDs such as aspirin, diclofenac and naproxen and, until recently, the COX-2 selective drugs Celebrex® and Vioxx® were also widely used. Inflammation was further controlled by glucocorticoids, and their combination with NSAIDs provided reasonably effective short-term control of the inflammation. More recently, a more aggressive approach to treating RA has been introduced starting at disease onset, using so-called disease-modifying anti-rheumatic drugs (DMARDs), which act to slow or even prevent disease progression. These include a number of older drugs, including gold salts; sulfasalazine; antimalarials such as hydroxychloroquine; D-penicillamine; immunosuppressants such as mycophenolic acid, azathioprine, cyclosporine A, tacrolimus and sirolimus; minocycline; leflunomide; and most importantly, methotrexate (see, e.g., Smolen et al, 2003).

Methotrexate is now the gold-standard therapy for clinical trial comparisons, and is generally used in combination with newer therapies. It is effective in most patients but, in common with all of the above agents, has significant gastrointestinal side effects, which lead to roughly 50% of patients eventually having to cease treatment with methotrexate (see, e.g., Mount et al, 2005). A further drawback of these older DMARDs is the length of time taken for the drug to start acting, ranging from weeks with methoxtrexate, to months with gold salts. Whilst full remissions only occur in about a quarter of patients, for those showing no effect it is not generally possible to stop therapy without suffering the risk of a more violent disease rebound (see, e.g., Smolen et al, 2003). In recent years, the treatment of RA has been revolutionised by the advent of biological agents which target specific inflammatory pathways. The first and most important of these are the anti-tumour necrosis factor (anti-TNF) agents (see, e.g., Elliott et al, 1994).

The Role of TNFα in RA

As discussed above, the TNF superfamily of receptors and ligands plays a key role in the causation of inflammation and associated local and systemic bone loss. TNFα production within the joint may in fact play the pivotal role in orchestrating the production of other factors which leads to the persistence of inflammation and tissue damage (see, e.g., Feldmann et al, 2001; Brennan et al, 1999; Brennan, 1992). The importance of TNFα in RA is highlighted by the finding that antibodies blocking TNFα can prevent inflammation in animal models of RA, and that anti-TNFα therapy is currently the most effective treatment for RA (see, e.g., Elliott et al, 1994; Feldmann et al, 1994; Joosten et al 1996, Klareskog et al, 2006). However, there is evidence that there are some TNFα-independent effects of IL-1 in RA, most notably bone destruction (see, e.g., van den Berg et al, 1999; van den Berg et al, 2002).

TNFα is a cytokine that effects many different functions, including the alteration of tissue remodelling, changes to the permeability of the epithelial cell barrier, activation of macrophages, up-regulation of adhesion molecules, recruitment of other immune response effectors and, most importantly in RA, it instigates the signalling cascade which leads to the activation of the transcription factors NFκB and AP-1 (see, e.g., Liu, 2005; Baud et al, 1999). Binding of TNFα and IL-1 to their respective receptors leads to the recruitment of downstream signal transducers called TRAFs. Further kinases are recruited by the TRAFs, and the resulting kinase complex activates the MAP-kinase pathway, ultimately leading to activation of AP-1, and the phosphorylation of IκB kinase. IκB is the inhibitor of NFκB, which acts by preventing translocation of NFκB to the nucleus. Phosphorylation of IκB by IκB kinase leads to degradation of IκB. Once IκB has been degraded, NFκB migrates to the nucleus, where it promotes transcription of anti-apoptotic genes, which promote survival of T and B-cells, thereby prolonging the immune response. This prolongation of the inflammatory response is central to the chronic nature of RA. The importance of NFκB activation is demonstrated by the fact that inhibition of NFκB activity by inhibitory peptides can prevent arthritis in animal models of RA (see, e.g., Jimi et al, 2004).

Anti-TNFα Therapy

Anti-TNFα therapy represents the market-leading therapies for RA, and is performed either with neutralising antibodies such as infliximab (Remicade® J&J and Schering Plough) and adalimumab (Humira®, Abbott) or decoy receptors such as etanercept (Enbrel® Amgen and Wyeth), both which represent validated and highly effective treatments for RA. Anti-TNFα biologicals are already licensed for RA, Crohn's disease, and psoriasis. A number of other inflammatory and autoimmune disorders are also being investigated as potential targets. Other approaches to blocking the action of TNFα include the pegylated anti-TNFα fragment certolizumab (Cimzia®, UCB); inhibition of proximal signalling intermediates such as MAP kinase; interference with the synthesis of TNFα via inhibition of TNFα converting enzyme (TACE); and inhibition of the metalloproteases responsible for cleaving TNFα from the cell surface (see, e.g., Smolen et al, 2003; Mount et al, 2005).

Other Inhibitors of NFκB Activation

As described above, the binding of IL-1 and RANKL to their receptors also initiates a signalling cascade, which eventually leads to the activation of NFκB and subsequent inflammatory response. The efficacy of inhibitors of these ligands has been validated by the use of the IL-1 receptor antagonist anakinra (Kineret® Amgen) for the treatment of RA, and the completion of clinical trials for the monoclonal antibody against RANKL AMG-162 (Denosumab® Amgen) for osteoporosis (it is also in clinical trials for RA and psoriasis).

Other Common Inflammatory Diseases Mediated by TNF α

There are several other common inflammatory diseases in which TNFα has been shown to play a major role and in which TNFα inhibitors have found therapeutic use. These include inflammatory bowel disease (IBD) and psoriasis.

IBD is an inflammatory disorder of the gut affecting about 0.25% of the population in the western world, of which the two main forms are: ulcerative colitis (UC), in which the lining of the colon becomes inflamed and ulcerated; and Crohn's disease (CD), which can occur anywhere within the gastrointestinal tract, but most often the ileum, and commonly involves inflammation of the entire gut wall. Common symptoms of IBD are bloody diarrhoea and abdominal pain.

Psoriasis is an inflammatory response of the skin affecting 1-3% of the population in the western world. The disease is characterised by raised, red, scaly plaques on the skin, which may be itchy and also cause significant psychological distress by their unsightly nature. A further complication of psoriasis is the development of psoriatic arthritis, an inflammatory arthritis of the joints, in up to 40% of patients, which develops on average 10 years after the first symptoms of skin disease are seen (see, e.g., Gottlieb, 2005).

As with RA, the aetiology of IBD and psoriasis are unknown and may involve a complex combination of infectious agents, environmental, and genetic factors, generating an inappropriate and prolonged inflammatory response.

Treatment of IBD and psoriasis has followed a similar pattern to that of RA, with the past use of immunoregulatory agents such as NSAIDs, methotrexate, cyclosporine, steroids, and antimetabolites such as 6-mercaptopurine for IBD (see, e.g., Korzenik et al, 2006) and methotrexate and cyclosporine for psoriasis (see, e.g., Gottlieb, 2005). The treatment of both has been revolutionised by the advent of biological agents, in particular those which block TNFα signalling. Etanercept is licensed for the treatment of psoriasis and psoriatic arthritis; both infliximab and adalimumab are licensed for psoriatic arthritis, IBD, and psoriasis.

Cancer

There is growing evidence that activation of NFκB can play a major role in the promotion and progression of both haematological malignancies, such as myeloma and lymphomas, and solid tumours, such as breast, prostate and lung cancer (see, e.g., Baud and Karin, 2009). There is also rising awareness of the role and importance of inflammation in cancer and in the development of resistance to radiotherapy and to chemotherapeutic agents, and it has been suggested that inflammation is in fact one of the basic hallmarks of cancer (see, e.g., Mantovani, 2009). Improving the efficacy of anti-cancer treatments by prevention of NFκB activation is therefore a promising strategy to augment existing therapeutic regimes and is currently under investigation, most notably for the treatment of multiple myeloma.

Defects in the normal apoptotic pathways are also implicated in the development and progression of tumour cell growth. Apoptosis (programmed cell death) plays a key role in the removal of abnormal cells; defects in the signalling cascades, which would normally lead to its induction, play a key role in oncogenesis. Radiotherapy and many chemotherapeutic agents act by causing cellular damage, which would normally induce apoptosis; defects in the pathway will therefore also reduce the effectiveness of such agents. The most important effector molecules in the signalling pathway leading to apoptosis are known as the caspases, which may be triggered by a number of stimuli, including TNFα binding to its receptor. Mutations in the genes which encode for the caspases have been found in a number of tumour types, including gastric, breast, renal cell and cervical cancers as well as commonly in T-cell lymphoblastic lymphoma and basal cell ameloblastomas (see, e.g., Philchenkov et al., 2004). Compounds which activate caspases, and thus sensitise cells to apoptosis, would be highly effective as cancer therapies either as single agents or in enhancing the effectiveness of existing cancer chemotherapy and radiotherapy.

Common Bone Diseases

Osteoporosis is a common disease characterised by reduced bone density, deterioration of bone tissue, and an increased risk of fracture. Many factors contribute to the pathogenesis of osteoporosis including poor diet, lack of exercise, smoking, and excessive alcohol intake. Osteoporosis may also arise in association with inflammatory diseases such as rheumatoid arthritis, endocrine diseases such as thyrotoxicosis, and with certain drug treatments such as treatment with glucocorticoids. However one of the most important factors in the pathogenesis of osteoporosis is heredity.

Paget's disease of bone is a common condition of unknown cause, characterised by increased bone turnover and disorganised bone remodelling, with areas of increased osteoclastic and osteoblast activity. Although Pagetic bone is often denser than normal, the abnormal architecture causes the bone to be mechanically weak, resulting in bone deformity and increased susceptibility to pathological fracture.

Many types of cancer affect bone. Cancer-associated bone disease can be manifest by the occurrence of hypercalcaemia or the development of osteolytic and/or osteosclerotic metastases. Increased osteoclastic bone resorption plays a key role in the pathogenesis of both conditions. Whilst almost any cancer can be complicated by bone metastases, the most common sources are multiple myeloma, breast carcinoma, and prostate carcinoma. The most common tumours associated with hypercalcaemia are multiple myeloma, breast carcinoma, and lung carcinoma.

RANKL signalling has been shown to play a major role in osteoclast over-activity and a consequent increase in bone loss (see, e.g., Tanaka et al, 2003; Roodman, 2006). The use of drugs which affect this pathway has been validated by the completion of clinical trials of the monoclonal antibody against RANKL AMG-162 (Denosumab® Amgen) for the treatment of osteoporosis/multiple myeloma.

As described previously, bone loss also plays a major role in the pathophysiology of rheumatoid arthritis and drugs which prevent activation of the signalling pathways described (e.g. TNFα blockers) are also able to prevent this bone loss.

Agents that Prevent Inflammation and/or Bone Loss

The inventors have identified a new class of compounds which, for example, prevent inflammation and/or bone loss, and thus may be used in the treatment of diseases with an inflammatory or autoimmune component, including, for example, rheumatoid arthritis, inflammatory bowel disease, psoriasis, and psoriatic arthritis; diseases which involve bone loss, including, for example, bone loss associated with rheumatoid arthritis, osteoporosis, Paget's disease of bone, and multiple myeloma; as well as cancer associated with activation of NFκB, with aberrant NFκB signaling, or with inflammation, including haematological malignancies such as multiple myeloma, leukaemia, T-cell lymphoblastic lymphoma, and other lymphoma (e.g., non-Hodgkin Lymphoma), and solid tumours such as cancer of the bladder, breast cancer (female and/or male), colon cancer, kidney cancer, lung cancer, pancreatic cancer, prostate cancer, brain cancer, skin cancer, thyroid cancer, and melanoma; and cancer associated with the inactivation or impairment of caspase-mediated cell death, such as gastric cancer, breast cancer, renal cancer, cervical cancer, and basal cell ameloblastomas.

Without wishing to be bound by any particular theory, the inventors believe that this action may be via a mechanism that involves blocking TNFα and/or IL-1 and/or RANKL-signalling.

Biphenyl Sulfonamides

Greig et al., 2004 and Greig et al., 2006 describe a class of biphenyl alkyl sulfonamides as anti-resorptive agents for the treatment of bone diseases, including, for example, 2',4'-difluoro-biphenyl-4-sulfonic acid (5-hydroxy-pentyl)-amide (ABD248) and 2',4'-difluoro-biphenyl-4-sulfonic acid (4-hydroxy-butyl)-amide (ABD256) (shown below).

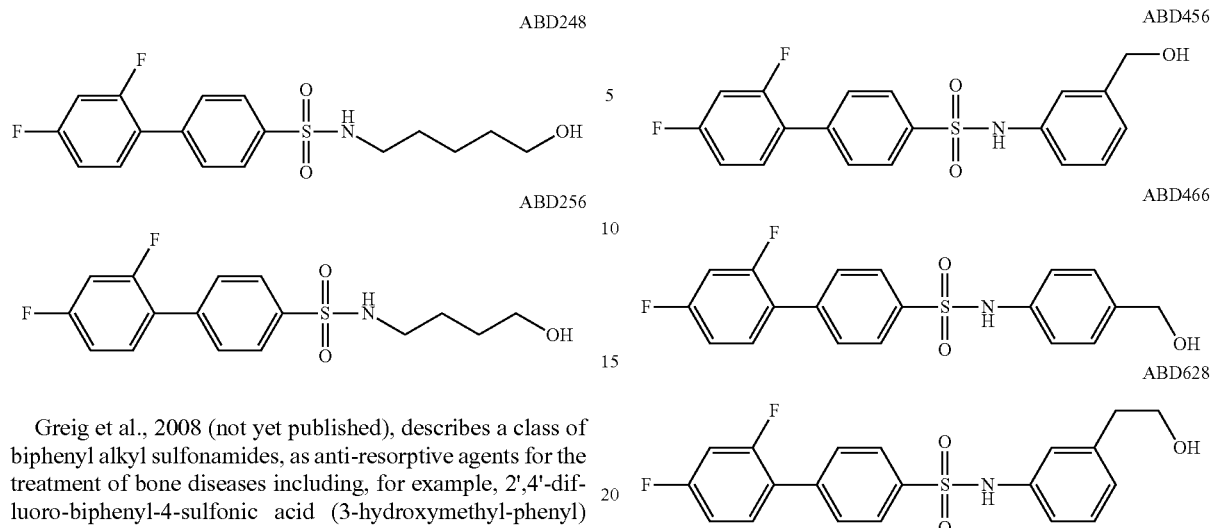

Greig et al., 2008 (not yet published), describes a class of biphenyl alkyl sulfonamides, as anti-resorptive agents for the treatment of bone diseases including, for example, 2',4'-difluoro-biphenyl-4-sulfonic acid (3-hydroxymethyl-phenyl)amide (ABD456), 2',4'-difluoro-biphenyl-4-sulfonic acid (4-hydroxymethyl-phenyl)amide (ABD466), and 2',4'-difluoro-biphenyl-4-sulfonic acid [3-(2-hydroxy-ethyl)-phenyl]-amide (ABD628), shown below.

It appears that compounds of the following formulae may be known:

| No. | Structure | Registry No. |
|---|---|---|
| 1 | 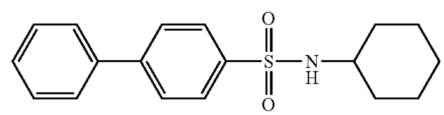 | 297742-90-6 |
| 2 | 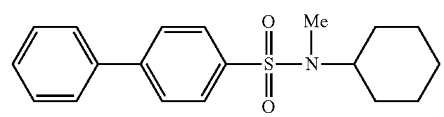 [SMILES: CN(C1CCCCC1)S(=O)(=O)c1ccc(-c2ccccc2)cc1] | 496015-30-6 |
| 3 | 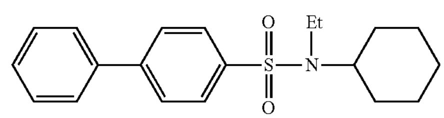 [SMILES: CCN(C1CCCCC1)S(=O)(=O)c1ccc(-c2ccccc2)cc1] | 496015-31-7 |
| 4 | 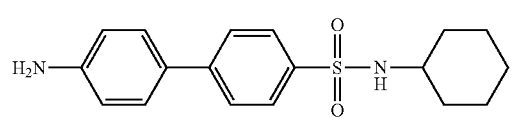 | 855253-65-5 |
| 5 | 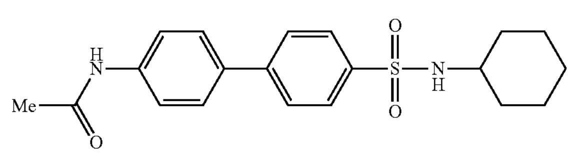 | 857624-18-1 |
| 6 | 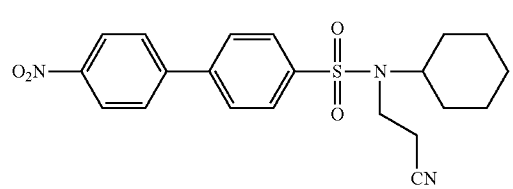 [SMILES: N#CCCN(C1CCCCC1)S(=O)(=O)c1ccc(-c2ccc([N+](=O)[O-])cc2)cc1] | 301354-93-8 |
| 7 | 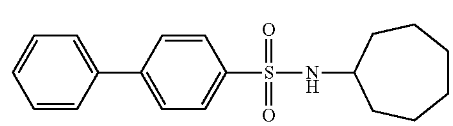 [SMILES: O=S(=O)(NC1CCCCCC1)c1ccc(-c2ccccc2)cc1] | 667901-42-0 |

-continued

| No. | Structure | Registry No. |
|---|---|---|
| 8 | biphenyl-SO2-N(cyclopentyl)(allyl) | 1022412-74-3 |
| 9 | 4'-Br-biphenyl-SO2-NH-C(cyclopentyl)-COOH | 326499-72-3 |
| 10 | 4'-Br-biphenyl-SO2-NH-C(cyclopentyl)-COOMe | 326500-04-3 |
| 11 | 4'-Br-biphenyl-SO2-NH-C(cyclopentyl)-COCl | 326500-05-4 |
| 12 | 4'-Br-biphenyl-SO2-NH-C(cyclohexyl)-COOH | 326499-76-7 |
| 13 | 4'-Br-biphenyl-SO2-NH-C(cyclohexyl)-CONHOH | 326499-74-5 |
| 14 | 4'-Br-biphenyl-SO2-NH-C(cyclopentyl)-CONHOH | 326499-73-4 |
| 15 | 4'-F-biphenyl-SO2-N(CH2CH2COOH)-C(cyclopentyl)-CONHOH | 220441-06-5 |
| 16 | 4'-F-biphenyl-SO2-N(CH2CH2COOMe)-C(cyclopentyl)-COOH | 220441-14-5 |
| 17 | 4'-F-biphenyl-SO2-N(CH2CH2COOMe)-C(cyclopentyl)-CONHOH | 220441-05-4 |

| No. | Structure | Registry No. |
|---|---|---|
| 18 | 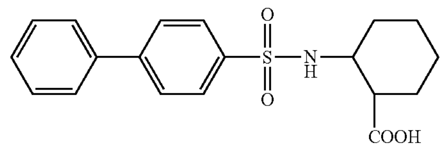 [SMILES: O=C(O)C1CCCCC1NS(=O)(=O)c1ccc(-c2ccccc2)cc1] | 866043-75-6<br>866043-74-5 |
| 19 | 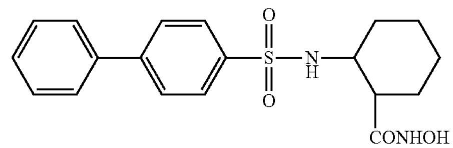 | 866043-71-2<br>866043-66-5<br>866043-65-4 |
| 20 | 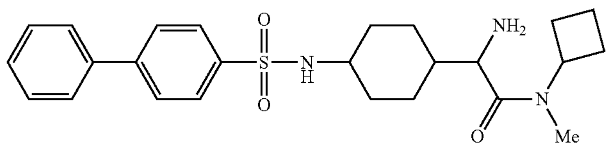 [SMILES: CN(C(=O)C(N)C1CCC(NS(=O)(=O)c2ccc(-c3ccccc3)cc2)CC1)C1CCC1] | 848632-03-1<br>848494-84-8 |

The present inventors have identified a new a class of aryl sulfonamides, as defined herein, that have surprising and unexpected properties.

The present inventors have identified a new a class of aryl sulfonamides, as defined herein, that have, inter alia, one or more surprising and unexpected properties.

Without wishing to be bound to any particular theory, the inventors believe that the new compounds have been protected against the major route of metabolism acting upon the previous biphenyl aryl sulfonamides (specifically, oxidation of the terminal alcohol to give a carboxylic acid) by the replacement of the aryl ring with a carbocyclic group; this may also be further combined with replacement of the alcohol by an amine. In addition to the resulting substantial improvement in metabolic stability, these replacement groups have also been selected to provide a further substantial enhancement in the aqueous solubility of the compounds. If a drug is to show oral activity, it must first be solvated, to permit absorption from the gastrointestinal tract. Second, the drug must be sufficiently resistant to first-pass metabolism by metabolic enzymes contained within the liver so as to be able to enter the circulation and permit sufficient quantities to reach the biological target. Third, the drug must be sufficiently potent against the biological target to give the desired therapeutic effect.

The optimization of pharmacokinetic properties (action of the body on the drug) of a drug is a developmental barrier of equal challenge as compared to the optimization of pharmacodynamic properties (action of the drug on the body). By improving both solubility and stability, with little or no loss of potency against the biological target, the new compounds disclosed herein show substantial improvements in their properties as oral therapeutic agents, as compared to previous compounds identified above. The new compounds combine the characteristics required of orally active agents for the treatment of inflammatory diseases and/or for the treatment of bone loss.

SUMMARY OF THE INVENTION

One aspect of the invention pertains to certain aryl-phenyl-sulfonamido-cycloalkyl compounds (for convenience, collectively referred to herein as "APSAC compounds"), as described herein.

Another aspect of the invention pertains to a composition (e.g., a pharmaceutical composition) comprising an APSAC compound, as described herein, and a pharmaceutically acceptable carrier or diluent.

Another aspect of the invention pertains to method of preparing a composition (e.g., a pharmaceutical composition) comprising the step of admixing an APSAC compound, as described herein, and a pharmaceutically acceptable carrier or diluent.

Another aspect of the invention pertains to a method of inhibiting an inflammatory response, in vitro or in vivo, comprising contacting an immune system component with an effective amount of an APSAC compound, as described herein.

Another aspect of the invention pertains to a method of inhibiting cellular and/or molecular pathways leading to joint destruction, in vitro or in vivo, comprising contacting cells associated with an immune response with a therapeutically-effective amount of an APSAC compound, as described herein.

Another aspect of the invention pertains to a method of inhibiting osteoclast survival, formation, and/or activity, in vitro or in vivo, comprising contacting an osteoclast with an effective amount of an APSAC compound, as described herein.

Another aspect of the invention pertains to a method of inhibiting bone resorption, in vitro or in vivo, comprising contacting cells in the bone microenvironment with a therapeutically-effective amount of an APSAC compound, as described herein.

Another aspect of the present invention pertains to a method of treatment comprising administering to a subject in need of treatment a therapeutically-effective amount of an APSAC compound, as described herein, preferably in the form of a pharmaceutical composition.

Another aspect of the present invention pertains to an APSAC compound as described herein for use in a method of treatment of the human or animal body by therapy.

Another aspect of the present invention pertains to use of an APSAC compound, as described herein, in the manufacture of a medicament for use in treatment.

In one embodiment, the treatment is treatment of inflammation and/or joint destruction and/or bone loss.

In one embodiment, the treatment is treatment of disorders mediated by excessive and/or inappropriate and/or prolonged activation of the immune system.

In one embodiment, the treatment is treatment of inflammatory and autoimmune disorders, for example, rheumatoid arthritis, psoriasis, psoriatic arthritis, chronic obstructive pulmonary disease (COPD), atherosclerosis, inflammatory bowel disease, ankylosing spondylitis, and the like.

In one embodiment, the treatment is treatment of inflammatory and autoimmune disorders, for example, rheumatoid arthritis, psoriasis, psoriatic arthritis, inflammatory bowel disease, ankylosing spondylitis, and the like.

In one embodiment, the treatment is treatment of disorders associated with bone loss, such as bone loss associated with excessive osteoclast activation in rheumatoid arthritis, osteoporosis, cancer-associated bone disease, Paget's disease and the like.

In one embodiment, the treatment is treatment of a haematological malignancy, e.g., multiple myeloma, leukaemia, or lymphoma (e.g., non-Hodgkin Lymphoma), e.g., a haematological malignancy, multiple myeloma, leukaemia, or lymphoma (e.g., non-Hodgkin Lymphoma) associated with activation of NFκB, with aberrant NFκB signalling, or with inflammation, e.g., alone, or in combination with, and to augment the efficacy of, radiotherapy or chemotherapy.

In one embodiment, the treatment is treatment of a solid tumour cancer, e.g., cancer of the bladder, breast cancer (female and/or male), colon cancer, kidney cancer, lung cancer, pancreatic cancer, prostate cancer, brain cancer, skin cancer, thyroid cancer, or melanoma, e.g., a solid tumour cancer, cancer of the bladder, breast cancer (female and/or male), colon cancer, kidney cancer, lung cancer, pancreatic cancer, prostate cancer, brain cancer, skin cancer, thyroid cancer, and melanoma associated with activation of NFκB, with aberrant NFκB signalling, or with inflammation, e.g., alone, or in combination with, and to augment the efficacy of, radiotherapy or chemotherapy.

In one embodiment, the treatment is treatment of a haematological malignancy, e.g., T-cell lymphoblastic lymphoma, mantle cell lymphoma, or acute lymphoblastic leukemia, e.g., a haematological malignancy, T-cell lymphoblastic lymphoma, mantle cell lymphoma, or acute lymphoblastic leukemia associated with inactivation or impairment of caspase induction or with aberrant caspase signalling, e.g., alone or in combination with, and to augment the efficacy of, radiotherapy or chemotherapy.

In one embodiment, the treatment is treatment of a solid tumour cancer, e.g., renal cell carcinoma, breast cancer (female and/or male), gastric cancer, prostate cancer, colon cancer, or basal cell ameloblastoma, e.g., a solid tumour cancer, e.g., renal cell carcinoma, breast cancer (female and/or male), gastric cancer, prostate cancer, colon cancer, or basal cell ameloblastoma associated with inactivation or impairment of caspase induction or with aberrant caspase signalling, e.g., alone, or in combination with, and to augment the efficacy of, radiotherapy or chemotherapy.

In one embodiment, the treatment is part of treatment by combination therapy, e.g., in combination with, and to augment the efficacy of, radiotherapy or chemotherapy.

Another aspect of the present invention pertains to a kit comprising (a) an APSAC compound, as described herein, preferably provided as a pharmaceutical composition and in a suitable container and/or with suitable packaging; and (b) instructions for use, for example, written instructions on how to administer the compound.

Another aspect of the present invention pertains to an APSAC compound obtainable by a method of synthesis as described herein, or a method comprising a method of synthesis as described herein.

Another aspect of the present invention pertains to an APSAC compound obtained by a method of synthesis as described herein, or a method comprising a method of synthesis as described herein.

Another aspect of the present invention pertains to novel intermediates, as described herein, which are suitable for use in the methods of synthesis described herein.

Another aspect of the present invention pertains to the use of such novel intermediates, as described herein, in the methods of synthesis described herein.

As will be appreciated by one of skill in the art, features and preferred embodiments of one aspect of the invention will also pertain to other aspect of the invention.

DETAILED DESCRIPTION OF THE INVENTION

Compounds

Figure 1:
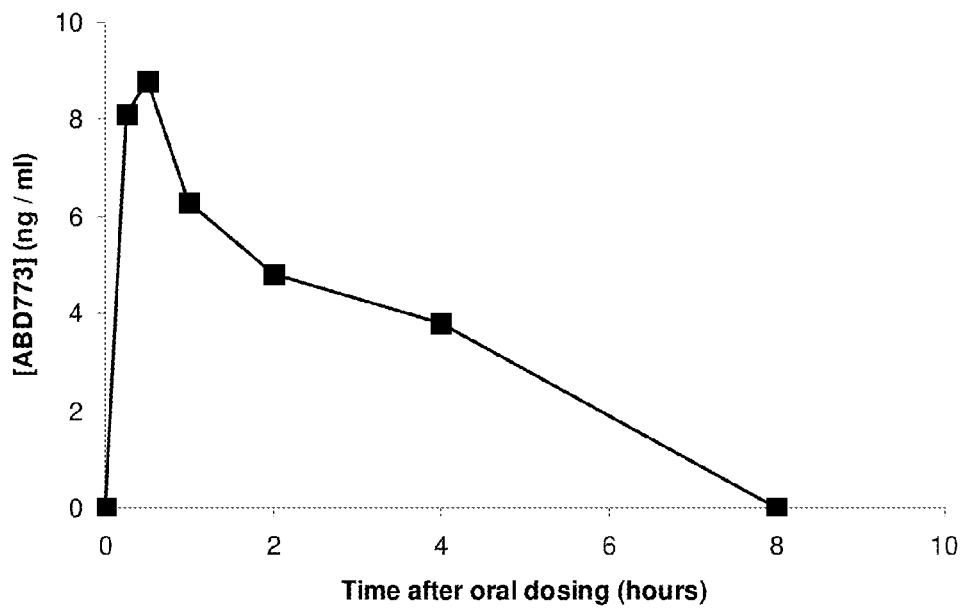
FIG. 1 is a graph showing mean plasma concentration (ng/mL) of the APSAC compound ABD773 (■) after oral administration (1 mg/kg) to a rat model.
Figure 2:
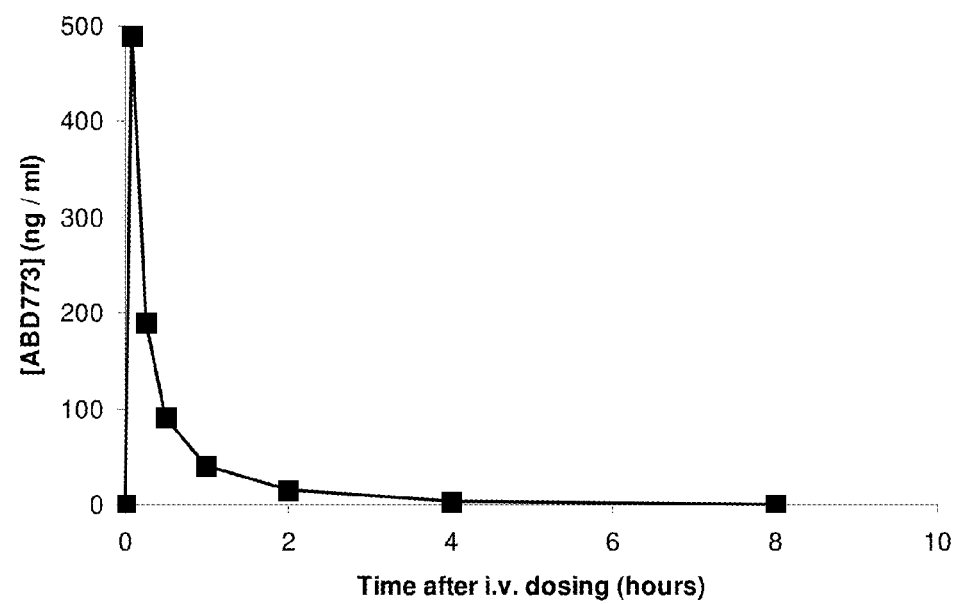
FIG. 2 is a graph showing mean plasma concentration (ng/mL) of the APSAC compound ABD773 (■) after intravenous administration (1 mg/kg) to a rat model.
Figure 3:
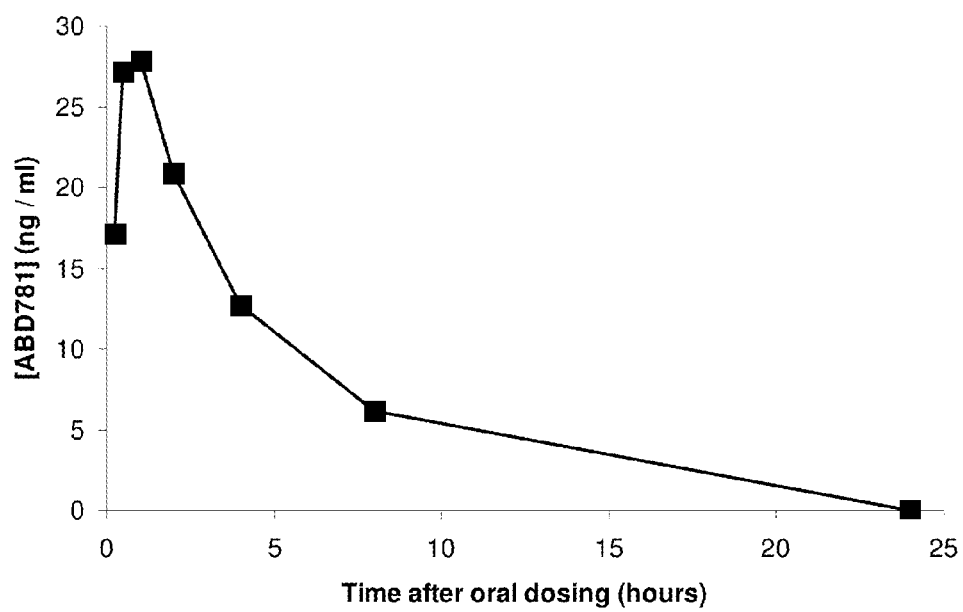
FIG. 3 is a graph showing mean plasma concentration (ng/mL) of the APSAC compound ABD781 (■) after oral administration (1 mg/kg) to a rat model.
Figure 4:
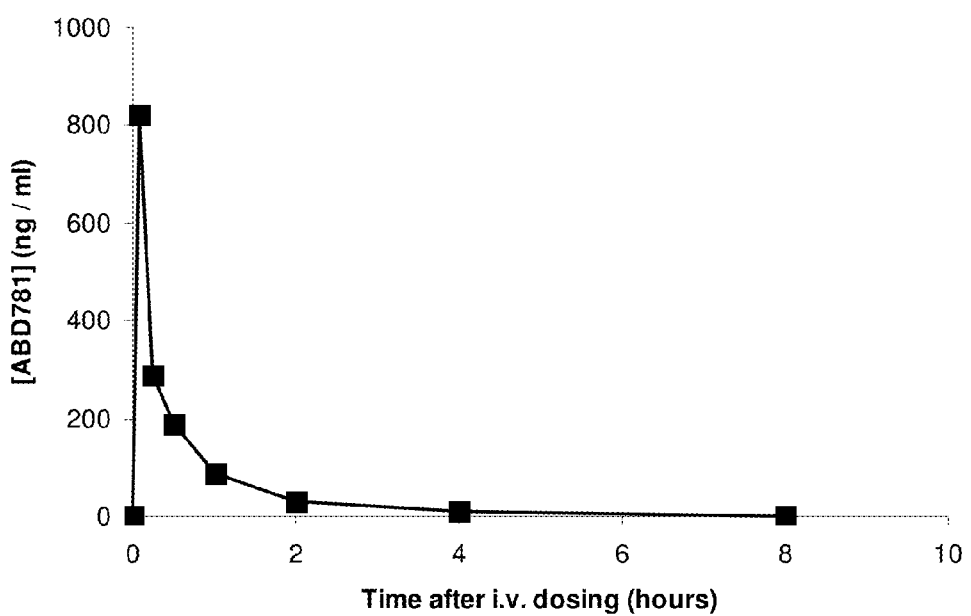
FIG. 4 is a graph showing mean plasma concentration (ng/mL) of the APSAC compound ABD781 (■) after intravenous administration (1 mg/kg) to a rat model.

The compounds of the present invention are structurally related to 1-(aryl)-phenyl-4-sulfonic acid cyclohexyl amide:

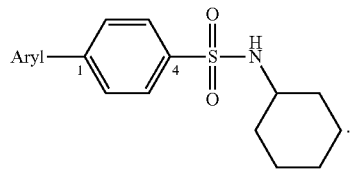

One aspect of the present invention pertains to compounds of the following formula, and pharmaceutically acceptable salts, hydrates, and solvates thereof (collectively referred to herein as "aryl-phenyl-sulfonamido-cycloalkyl" or "APSAC" compounds"):

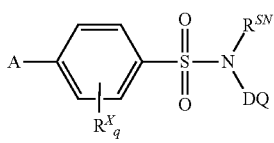

wherein:
-A is independently:

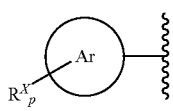

—Ar is independently phenyl, pyridinyl, or pyrimidinyl; and
p is independently an integer from 0 to 3;
and wherein:
q is independently an integer from 0 to 3;
and wherein:
—$R^{SN}$ is independently —H or saturated aliphatic $C_{1-4}$alkyl;
and wherein:
-DQ is independently -$D^1$-$Q^1$ or -$D^2$=O;
-$D^1$- is independently cyclopentane-di-yl, cyclohexane-di-yl, cycloheptane-di-yl, bicyclo[3.1.1]heptane-di-yl, or bicyclo[3.2.1]octane-di-yl, and is optionally substituted with one or more groups —$R^D$;
-$D^2$= is independently cyclopentane-yl-ylidene, cyclohexane-yl-ylidene, cycloheptane-yl-ylidene, bicyclo[3.1.1]heptane-yl-ylidene, or bicyclo[3.2.1]octane-yl-ylidene, and is optionally substituted with one or more groups —$R^D$;
each —$R^D$ is independently selected from —F, —Cl, —Br, —I, —$R^{DD}$, —$CF_3$, —OH, —$OR^{DD}$, —$NH_2$, —$NHR^{DD}$, and —$NR^{DD}_2$; and
each —$R^{DD}$ is independently saturated aliphatic $C_{1-4}$alkyl;
and wherein -$Q^1$ is independently selected from:

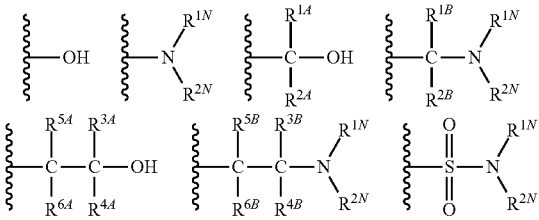

wherein:
each —$R^{1N}$ is independently —H, —$R^{CN}$, or —$R^{CF}$;
each —$R^{2N}$ is independently —H, —$R^{CN}$, or —$R^{CF}$;
each —$R^{CN}$ is independently saturated aliphatic $C_{1-4}$alkyl;
each —$R^{CF}$ is independently saturated aliphatic $C_{1-4}$fluoroalkyl;
or:
—$NR^{1N}R^{2N}$ is independently azetidino, pyrrolidino, imidazolidino, pyrazolidino, piperidino, piperazino, morpholino, thiomorpholino, azepino, or diazepino, each optionally substituted with one or more groups independently selected from saturated aliphatic $C_{1-4}$alkyl;
—$R^{1A}$ is independently —H, —$R^C$, or —$R^F$; and
—$R^{2A}$ is independently —H, —$R^C$, or —$R^F$;

or —$R^{1A}$ and —$R^{2A}$ together form a saturated aliphatic $C_{2-4}$alkylene group;
—$R^{1B}$ is independently —H, —$R^C$, or —$R^F$; and
—$R^{2B}$ is independently —H, —$R^C$, or —$R^F$;
or —$R^{1B}$ and —$R^{2B}$ together form a saturated aliphatic $C_{2-4}$alkylene group;
or —$R^{1B}$ and —$R^{2B}$ together form =O;
—$R^{3A}$ is independently —H, —$R^C$, or —$R^F$; and
—$R^{4A}$ is independently —H, —$R^C$, or —$R^F$;
or —$R^{3A}$ and —$R^{4A}$ together form a saturated aliphatic $C_{2-4}$alkylene group;
—$R^{5A}$ is independently —H, —$R^C$, —$R^F$, or —$R^J$; and
—$R^{6A}$ is independently —H, —$R^C$, or —$R^F$;
or —$R^{5A}$ and —$R^{6A}$ together form a saturated aliphatic $C_{2-4}$alkylene group;
—$R^{3B}$ is independently —H, —$R^C$, or —$R^F$; and
—$R^{4B}$ is independently —H, —$R^C$, or —$R^F$;
or —$R^{3B}$ and —$R^{4B}$ together form a saturated aliphatic $C_{2-4}$alkylene group;
—$R^{5B}$ is independently —H, —$R^C$, —$R^F$, —OH, or —$OR^O$; and
—$R^{6B}$ is independently —H, —$R^C$, or —$R^F$;
or —$R^{5B}$ and —$R^{6B}$ together form a saturated aliphatic $C_{2-4}$alkylene group;
each —$R^C$ is independently saturated aliphatic $C_{1-4}$alkyl;
each —$R^F$ is independently saturated aliphatic $C_{1-4}$fluoroalkyl;
—$R^O$ is independently saturated aliphatic $C_{1-4}$alkyl;
—$R^J$ is independently —$NH_2$, —$NHR^{JN1}$, —$NR^{JN1}_2$, or —$NR^{JN2}R^{JN3}$;
each —$R^{JN1}$ is independently saturated aliphatic $C_{1-4}$alkyl; and
—$NR^{JN2}R^{JN3}$ is independently azetidino, pyrrolidino, imidazolidino, pyrazolidino, piperidino, piperazino, morpholino, thiomorpholino, azepino, or diazepino, each optionally substituted with one or more groups independently selected from saturated aliphatic $C_{1-4}$alkyl;
and wherein each —$R^X$ is independently:
—F, —Cl, —Br, —I,
—$R^{XX}$,
—OH, —$OR^{XX}$,
—SH, —$SR^{XX}$,
—$CF_3$, —$OCF_3$, —$SCF_3$,
—$NH_2$, —$NHR^{XX}$, —$NR^{XX}_2$, —$NR^{YY}R^{ZZ}$,
—C(=O)$R^{XX}$, —OC(=O)$R^{XX}$,
—C(=O)OH, —C(=O)$OR^{XX}$,
—C(=O)$NH_2$, —C(=O)$NHR^{XX}$, —C(=O)$NR^{XX}_2$, —C(=O)$NR^{YY}R^{ZZ}$,
—OC(=O)$NH_2$, —OC(=O)$NHR^{XX}$, —OC(=O)$NR^{XX}_2$, —OC(=O)$NR^{YY}R^{ZZ}$,
—NHC(=O)$R^{XX}$, —$NR^{XX}$C(=O)$R^{XX}$,
—NHC(=O)$OR^{XX}$, —$NR^{XX}$C(=O)$OR^{XX}$,
—NHC(=O)$NH_2$, —NHC(=O)$NHR^{XX}$, —NHC(=O)$NR^{XX}_2$, —NHC(=O)$NR^{YY}R^{ZZ}$,
—$NR^{XX}$C(=O)$NH_2$, —$NR^{XX}$C(=O)$NHR^{XX}$, —$NR^{XX}$C(=O)$NR^{XX}_2$, —$NR^{XX}$C(=O)$NR^{YY}R^{ZZ}$, —CN,
—$NO_2$,
—S(=O)$_2NH_2$, —S(=O)$_2NHR^{XX}$, —S(=O)$_2NR^{XX}_2$, —S(=O)$_2NR^{YY}R^{ZZ}$,
—S(=O)$R^{XX}$, —S(=O)$_2R^{XX}$, —OS(=O)$_2R^{XX}$, —S(=O)$_2$OH, or —S(=O)$_2OR^{XX}$;
wherein:
each —$R^{XX}$ is independently saturated aliphatic $C_{1-6}$alkyl, phenyl, or benzyl, wherein said phenyl and benzyl are optionally substituted with one or more groups selected from: —F, —Cl, —Br, —I, —$CF_3$, —$OCF_3$, —$R^{XXX}$, —OH, —OR$^{XXX}$, or —SR$^{XXX}$, wherein each —R$^{XXX}$ is independently saturated aliphatic C$_{1-4}$alkyl; and each —NR$^{YY}$R$^{ZZ}$ is independently azetidino, pyrrolidino, imidazolidino, pyrazolidino, piperidino, piperazino, morpholino, thiomorpholino, azepino, or diazepino, each optionally substituted with one or more groups independently selected from saturated aliphatic C$_{1-4}$alkyl.

The Group -A

In one embodiment, -A is independently:

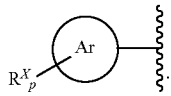

In one embodiment, —Ar is independently phenyl, pyridinyl, or pyrimidinyl.
In one embodiment, —Ar is independently phenyl.
In one embodiment, —Ar is independently pyridinyl.
In one embodiment, —Ar is independently pyridin-2-yl.
In one embodiment, —Ar is independently pyridin-3-yl.
In one embodiment, —Ar is independently pyridin-4-yl.

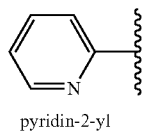 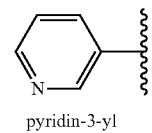 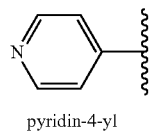

pyridin-2-yl     pyridin-3-yl     pyridin-4-yl

In one embodiment, —Ar is independently pyrimidinyl.
In one embodiment, —Ar is independently pyrimidin-2-yl.
In one embodiment, —Ar is independently pyrimidin-4-yl.
In one embodiment, —Ar is independently pyrimidin-5-yl.

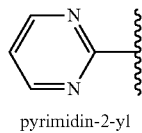 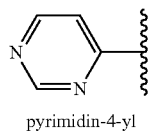 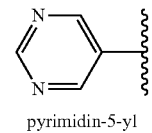

pyrimidin-2-yl     pyrimidin-4-yl     pyrimidin-5-yl

Substituents on —Ar

In one embodiment, p is independently an integer from 0 to 3.
In one embodiment, p is independently an integer from 1 to 3.
In one embodiment, p is independently 0.
In one embodiment, p is independently 1.
In one embodiment, p is independently 2.
In one embodiment, p is independently 3.

The Group -A: Phenyl and Pyridinyl

In one embodiment, -A is independently:

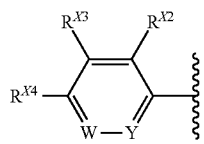

wherein:
=W— is —CH= or —CR$^W$= and —Y= is —CH= or —CR$^Y$=; or

=W— is —CH= or —CR$^W$= and —Y= is —N=; or
=W— is —N= and —Y= is —CH= or —CR$^Y$=;
—R$^W$ is independently saturated aliphatic C$_{1-4}$alkyl;
—R$^Y$ is independently saturated aliphatic C$_{1-4}$alkyl;
—R$^{X2}$ is independently —H or —R$^{X2S}$;
—R$^{X3}$ is independently —H or —R$^{X3S}$;
—R$^{X4}$ is independently —H or —R$^{X4S}$;
—R$^{X2S}$ is independently —R$^X$;
—R$^{X3S}$ is independently —R$^X$; and
—R$^{X4S}$ is independently —R$^X$.

In one embodiment, -A is independently:

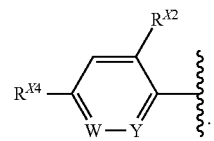

In one embodiment, -A is independently:

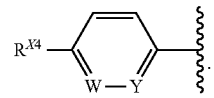

In one embodiment, -A is independently:

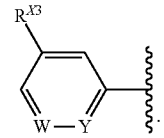

The Group -A: Phenyl and Pyridinyl: The Groups =W— and —Y=

In one embodiment, =W— is —CH= or —CR$^W$= and —Y= is —CH= or —CR$^Y$=.

In one embodiment, =W— is —CH= and —Y= is —CH=, as in, for example:

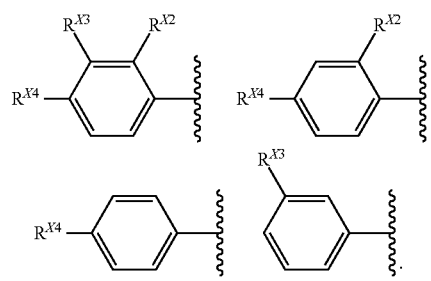

In one embodiment, =W— is —CH= or —CR$^W$= and —Y= is —N=.

In one embodiment, =W— is —CH= and —Y= is —N=, as in, for example:

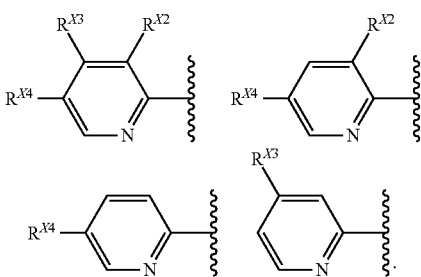

In one embodiment, =W— is —N= and —Y= is —CH= or —CR$^Y$=.

In one embodiment, =W— is —N= and —Y= is —CH=, as in, for example:

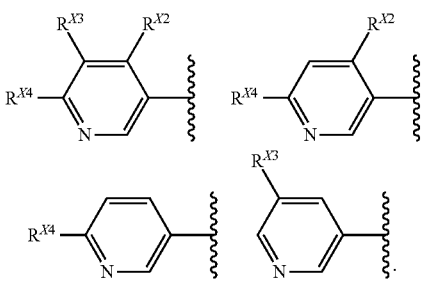

In one embodiment, —R$^W$, if present, is independently saturated aliphatic C$_{1-4}$alkyl.

In one embodiment, —R$^W$, if present, is independently -Me.

In one embodiment, —R$^Y$, if present, is independently saturated aliphatic C$_{1-4}$alkyl.

In one embodiment, —R$^Y$, if present, is independently -Me.

The Group -A: Phenyl: R$^{X2}$ and R$^{X4}$

In one embodiment, -A is independently:

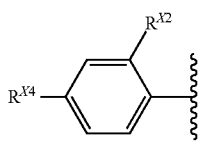

wherein:
—R$^{X2}$ is independently —H or —R$^{X2S}$;
—R$^{X4}$ is independently —H or —R$^{X4S}$;
—R$^{X2S}$ is independently —R$^X$; and
—R$^{X4S}$ is independently —R$^X$.

The Group —R$^{X2}$

In one embodiment, —R$^{X2}$, if present, is independently —H or —R$^{X2S}$.

In one embodiment, —R$^{X2}$, if present, is independently —R$^{X2S}$.

In one embodiment, —R$^{X2}$, if present, is independently —H.

The Group —R$^{X3}$

In one embodiment, —R$^{X3}$, if present, is independently —H or —R$^{X3S}$.

In one embodiment, —R$^{X3}$, if present, is independently —R$^{X3S}$.

In one embodiment, —R$^{X3}$, if present, is independently —H.

The Group —R$^{X4}$

In one embodiment, —R$^{X4}$, if present, is independently —H or —R$^{X4S}$.

In one embodiment, —R$^{X4}$, if present, is independently —R$^{X4S}$.

In one embodiment, —R$^{X4}$, if present, is independently —H.

Leading Phenylene Group

For the avoidance of doubt, the leading phenylene group is the phenylene group that links the group -A, on the left, with the group —S(=O)$_2$N(R$^S$N)(DQ), on the right.

And so, in one embodiment, the leading phenylene group is:

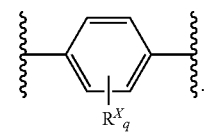

In one embodiment, q is independently an integer from 0 to 3.

In one embodiment, q is independently an integer from 1 to 3.

In one embodiment, q is independently 0.
In one embodiment, q is independently 1.
In one embodiment, q is independently 2.
In one embodiment, the leading phenylene group is:

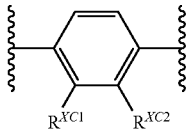

wherein:
—R$^{XC1}$ is independently —H or —R$^X$; and
—R$^{XC2}$ is independently —H or —R$^X$.
In one embodiment:
—R$^{XC1}$ is independently —H or —R$^X$; and
—R$^{XC2}$ is independently —H;
or:
—R$^{XC1}$ is independently —H; and
—R$^{XC2}$ is independently —H or —R$^X$;
or:
—R$^{XC1}$ is independently —H; and
—R$^{XC2}$ is independently —H.
In one embodiment:
—R$^{XC1}$ is independently —H; and
—R$^{XC2}$ is independently —H or —R$^X$.
In one embodiment:
—R$^{XC1}$ is independently —H or —R$^X$; and
—R$^{XC2}$ is independently —H.
In one embodiment:
—R$^{XC1}$ is independently —H; and
—R$^{XC2}$ is independently —H.
The Group —R$^X$ In one embodiment, each —R$^X$, if present, is independently:
—F, —Cl, —Br, —I,
—R$^{XX}$,
—OH, —OR$^{XX}$, —SH, —SR$^{XX}$,
—CF$_3$, —OCF$_3$, —SCF$_3$,
—NH$_2$, —NHR$^{XX}$, —NR$^{XX}$$_2$, —NR$^{YY}$R$^{ZZ}$,
—C(=O)R$^{XX}$, —OC(=O)R$^{XX}$,
—C(=O)OH, —C(=O)OR$^{XX}$,
—C(=O)NH$_2$, —C(=O)NHR$^{XX}$, —C(=O)NR$^{XX}$$_2$, —C(=O)NR$^{YY}$R$^{ZZ}$,
—OC(=O)NH$_2$, —OC(=O)NHR$^{XX}$, —OC(=O)NR$^{XX}$$_2$, —OC(=O)NR$^{YY}$R$^{ZZ}$,
—NHC(=O)R$^{XX}$, —NR$^{XX}$C(=O)R$^{XX}$,
—NHC(=O)OR$^{XX}$, —NR$^{XX}$C(=O)OR$^{XX}$,
—NHC(=O)NH$_2$, —NHC(=O)NHR$^{XX}$, —NHC(=O)NR$^{XX}$$_2$, —NHC(=O)NR$^{YY}$R$^{ZZ}$,
—NR$^{XX}$C(=O)NH$_2$, —NR$^{XX}$C(=O)NHR$^{XX}$, —NR$^{XX}$C(=O)NR$^{XX}$$_2$, —NR$^{XX}$C(=O)NR$^{YY}$R$^{ZZ}$,
—CN,
—NO$_2$,
—S(=O)$_2$NH$_2$, —S(=O)$_2$NHR$^{XX}$, —S(=O)$_2$NR$^{XX}$$_2$, —S(=O)$_2$NR$^{YY}$R$^{ZZ}$,
—S(=O)R$^{XX}$, —S(=O)$_2$R$^{XX}$, —OS(=O)$_2$R$^{XX}$, —S(=O)$_2$OH, or —S(=O)$_2$OR$^{XX}$;
wherein:
each —R$^{XX}$ is independently saturated aliphatic C$_{1-6}$alkyl, phenyl, or benzyl, wherein said phenyl and benzyl are optionally substituted with one or more groups selected from: —F, —Cl, —Br, —I, —CF$_3$, —OCF$_3$, —R$^{XXX}$, —OH, —OR$^{XXX}$, or —SR$^{XXX}$, wherein each —R$^{XXX}$ is independently saturated aliphatic C$_{1-4}$alkyl; and
each —NR$^{YY}$R$^{ZZ}$ is independently azetidino, pyrrolidino, imidazolidino, pyrazolidino, piperidino, piperazino, morpholino, thiomorpholino, azepino, or diazepino, each optionally substituted with one or more groups independently selected from saturated aliphatic C$_{1-4}$alkyl.
In one embodiment, each —R$^X$, if present, is independently:
—F, —Cl, —Br, —I,
—R$^{XX}$,
—OH, —OR$^{XX}$,
—SH, —SR$^{XX}$,
—CF$_3$, —OCF$_3$, —SCF$_3$,
—NH$_2$, —NHR$^{XX}$, —NR$^{XX}$$_2$, —NR$^{YY}$R$^{ZZ}$,
—C(=O)R$^{XX}$, —OC(=O)R$^{XX}$,
—C(=O)OH, —C(=O)OR$^{XX}$,
—C(=O)NH$_2$, —C(=O)NHR$^{XX}$, —C(=O)NR$^{XX}$$_2$, —C(=O)NR$^{YY}$R$^{ZZ}$,
—CN,
—NO$_2$,
—S(=O)$_2$NH$_2$, —S(=O)$_2$NHR$^{XX}$, —S(=O)$_2$NR$^{XX}$$_2$, or —S(=O)$_2$NR$^{YY}$R$^{ZZ}$.
In one embodiment, each —R$^X$, if present, is independently —F, —Cl, —Br, —I, —R$^{XX}$, —OH, —OR$^{XX}$, —SR$^{XX}$, —CF$_3$, —OCF$_3$, —SCF$_3$, —C(=O)R$^{XX}$, —CN, or —NO$_2$.
In one embodiment, each —R$^X$, if present, is independently —F, —Cl, —Br, —I, —R$^{XX}$, —OH, —OR$^{XX}$, —SR$^{XX}$, —CF$_3$, —OCF$_3$, —SCF$_3$, —CN, or —NO$_2$.
In one embodiment, each —R$^X$, if present, is independently —F, —Cl, —Br, —I, —R$^{XX}$, —OH, —OR$^{XX}$, —SR$^{XX}$, —CF$_3$, —OCF$_3$, —CN, or —NO$_2$.
In one embodiment, each —R$^X$, if present, is independently —F, —Cl, —Br, —I, —R$^{XX}$, —OR$^{XX}$, —SR$^{XX}$, —CF$_3$, or —OCF$_3$.
In one embodiment, each —R$^{XX}$, if present, is independently saturated aliphatic C$_{1-6}$alkyl, phenyl, or benzyl.
In one embodiment, each —R$^{XX}$, if present, is independently saturated aliphatic C$_{1-6}$alkyl.

In one embodiment, each —R$^{XX}$, if present, is independently saturated aliphatic C$_{1-4}$alkyl.
In one embodiment, —NR$^{YY}$R$^{ZZ}$ if present, is independently pyrrolidino, imidazolidino, pyrazolidino, piperidino, piperazino, or morpholino, each optionally substituted with one or more groups independently selected from saturated aliphatic C$_{1-4}$alkyl.
In one embodiment, —NR$^{YY}$R$^{ZZ}$ if present, is independently pyrrolidino, piperidino, piperazino, or morpholino, each optionally substituted with one or more groups independently selected from saturated aliphatic C$_{1-4}$alkyl.

Substituents on the Leading Phenylene Group

In one embodiment, the leading phenylene group is:

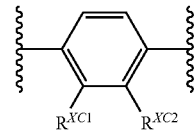

wherein:
—R$^{XC1}$ is independently —H or —R$^{XCC}$; and
—R$^{XC2}$ is independently —H or —R$^{XCC}$;
wherein each —R$^{XCC}$ is independently:
—F, —Cl, —R$^{XCCC}$, —OR$^{XCCC}$, —CF$_3$, —OCF$_3$;
wherein each —R$^{XCCC}$ is independently saturated aliphatic C$_{1-4}$alkyl.
In one embodiment:
—R$^{XC1}$ is independently —H or —R$^{XCC}$; and
—R$^{XC2}$ is independently —H;
or:
—R$^{XC1}$ is independently —H; and
—R$^{XC2}$ is independently —H or —R$^{XCC}$;
or:
—R$^{XC1}$ is independently —H; and
—R$^{XC2}$ is independently —H.
In one embodiment:
—R$^{XC1}$ is independently —H; and
—R$^{XC2}$ is independently —H or —R$^{XCC}$.
In one embodiment:
—R$^{XC1}$ is independently —H or —R$^{XCC}$; and
—R$^{XC2}$ is independently —H.
In one embodiment:
—R$^{XC1}$ is independently —H; and
—R$^{XC2}$ is independently —H.
In one embodiment, each —R$^{XCC}$, if present, is independently —F, —Cl, or —R$^{XCCC}$.
In one embodiment, each —R$^{XCC}$, if present, is independently —R$^{XCCC}$.
In one embodiment, each —R$^{XCCC}$, if present, is independently -Me, -Et, -nPr, or -iPr.
In one embodiment, each —R$^{XCCC}$, if present, is independently -Me or -Et.

The Group —R$^{X2S}$

In one embodiment, —R$^{X2S}$, if present, is independently —R$^X$.
In one embodiment, —R$^{X2S}$, if present, is independently —F, —Cl, —Br, —I, —R$^{XA}$, —OR$^{XA}$, —SR$^{XA}$, —CF$_3$, or —OCF$_3$, wherein each —R$^{XA}$ is independently saturated aliphatic C$_{1-4}$alkyl.
In one embodiment, —R$^{X2S}$, if present, is independently —F, —Cl, —Br, —I, —R$^{XA}$, —OR$^{XA}$, —CF$_3$, or —OCF$_3$.
In one embodiment, —R$^{X2S}$, if present, is independently —F, —Cl, —Br, —I, —CF$_3$, or —OCF$_3$.

In one embodiment, —$R^{X2S}$, if present, is independently —F, —Cl, or —$CF_3$.

In one embodiment, —$R^{X2S}$, if present, is independently —F or —Cl.

In one embodiment, —$R^{X2S}$, if present, is independently —F.

In one embodiment, —$R^{X2S}$, if present, is independently —Cl.

The Group —$R^{X3S}$

In one embodiment, —$R^{X3S}$, if present, is independently —$R^X$.

In one embodiment, —$R^{X3S}$, if present, is independently —F, —Cl, —Br, —I, —$R^{XA}$, —$OR^{XA}$, —$SR^{XA}$, —$CF_3$, or —$OCF_3$, wherein each —$R^{XA}$ is independently saturated aliphatic $C_{1-4}$alkyl.

In one embodiment, —$R^{X3S}$, if present, is independently —F, —Cl, —Br, —I, —$R^{XA}$, —$OR^{XA}$, —$CF_3$, or —$OCF_3$.

In one embodiment, —$R^{X3S}$, if present, is independently —F, —Cl, —Br, —I, —$CF_3$, or —$OCF_3$.

In one embodiment, —$R^{X3S}$, if present, is independently —F, —Cl, or —$CF_3$.

In one embodiment, —$R^{X3S}$, if present, is independently —F or —Cl.

In one embodiment, —$R^{X3S}$, if present, is independently —F.

In one embodiment, —$R^{X3S}$, if present, is independently —Cl.

The Group —$R^{X4S}$

In one embodiment, —$R^{X4S}$, if present, is independently —$R^X$.

In one embodiment, —$R^{X4S}$, if present, is independently —F, —Cl, —Br, —I, —$R^{XA}$, —$OR^{XA}$, —$SR^{XA}$, —$CF_3$, or —$OCF_3$, wherein each —$R^{XA}$ is independently saturated aliphatic $C_{1-4}$alkyl.

In one embodiment, —$R^{X4S}$, if present, is independently —F, —Cl, —Br, —I, —$R^{XA}$, —$OR^{XA}$, —$CF_3$, or —$OCF_3$.

In one embodiment, —$R^{X4S}$, if present, is independently —F, —Cl, —Br, —I, —$CF_3$, or —$OCF_3$.

In one embodiment, —$R^{X4S}$, if present, is independently —F, —Cl, or —$CF_3$.

In one embodiment, —$R^{X4S}$, if present, is independently —F or —Cl.

In one embodiment, —$R^{X4S}$, if present, is independently —F.

In one embodiment, —$R^{X4S}$, if present, is independently —Cl.

In one embodiment, —$R^{X2S}$ and —$R^{X4S}$, if present, are each independently —F.

In one embodiment, —$R^{X2S}$ and —$R^{X4S}$, if present, are each independently —Cl.

The Group —$R^{XA}$

In one embodiment, each —$R^{XA}$, if present, is independently saturated aliphatic $C_{1-4}$alkyl.

In one embodiment, each —$R^{XA}$, if present, is independently -Me or -Et.

In one embodiment, each —$R^{XA}$, if present, is independently -Me.

The Group -DQ

In embodiment, -DQ is independently -$D^1$-$Q^1$ or -$D^2$=O.

In embodiment, -DQ is independently -$D^1$-$Q^1$.

In embodiment, -DQ is independently -$D^2$=O.

The Group -$D^1$-

In one embodiment, -$D^1$-, if present, is independently cyclopentane-di-yl, cyclohexane-di-yl, cycloheptane-di-yl, bicyclo[3.1.1]heptane-di-yl, or bicyclo[3.2.1]octane-di-yl, and is optionally substituted with one or more groups —$R^D$.

In one embodiment, -$D^1$-, if present, is independently cyclopentane-di-yl, cyclohexane-di-yl, or cycloheptane-di-yl, and is optionally substituted with one or more groups —$R^D$.

In one embodiment, -$D^1$-, if present, is independently cyclopentane-di-yl, cyclohexane-di-yl, cycloheptane-di-yl, bicyclo[3.1.1]heptane-di-yl, or bicyclo[3.2.1]octane-di-yl.

In one embodiment, -$D^1$-, if present, is independently cyclopentane-di-yl, cyclohexane-di-yl, or cycloheptane-di-yl.

In one embodiment, -$D^1$-, if present, is independently cyclopentane-di-yl or cyclohexane-di-yl.

In one embodiment, -$D^1$-, if present, is independently cyclopentane-di-yl.

In one embodiment, -$D^1$-, if present, is independently cyclopentane-1,2-di-yl.

In one embodiment, -$D^1$-, if present, is independently cyclopentane-1,3-di-yl.

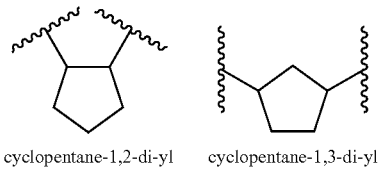 [SMILES: *C1CCCC1* ; *C1CCC(*)C1]

cyclopentane-1,2-di-yl    cyclopentane-1,3-di-yl

In one embodiment, -$D^1$-, if present, is independently cyclohexane-di-yl.

In one embodiment, -$D^1$-, if present, is independently cyclohexane-1,2-di-yl.

In one embodiment, -$D^1$-, if present, is independently cyclohexane-1,3-di-yl.

In one embodiment, -$D^1$-, if present, is independently cyclohexane-1,4-di-yl.

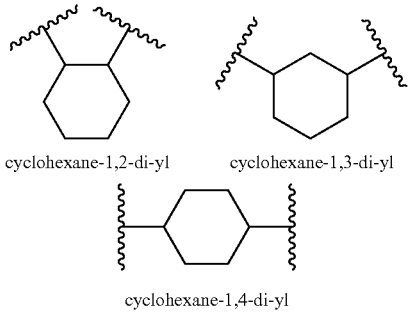

cyclohexane-1,2-di-yl    cyclohexane-1,3-di-yl cyclohexane-1,4-di-yl

In one embodiment, -$D^1$-, if present, is independently cycloheptane-di-yl.

In one embodiment, -$D^1$-, if present, is independently cycloheptane-1,2-di-yl.

In one embodiment, -$D^1$-, if present, is independently cycloheptane-1,3-di-yl.

In one embodiment, -$D^1$-, if present, is independently cycloheptane-1,4-di-yl.

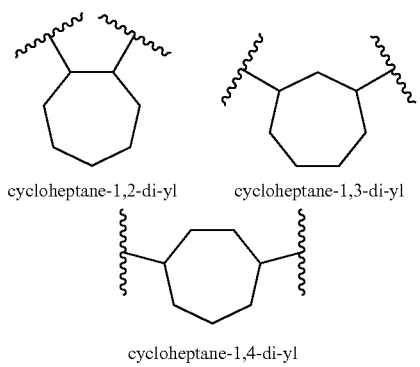

cycloheptane-1,2-di-yl    cycloheptane-1,3-di-yl cycloheptane-1,4-di-yl

In one embodiment, -D$^1$-, if present, is independently cyclopentane-1,2-di-yl, cyclopentane-1,3-di-yl, cyclohexane-1,3-di-yl, cyclohexane-1,4-di-yl, or cycloheptane-1,4-di-yl.

In one embodiment, -D$^1$-, if present, is independently cyclopentane-1,2-di-yl, cyclopentane-1,3-di-yl, or cyclohexane-1,4-di-yl.

In one embodiment, -D$^1$-, if present, is independently bicyclo[3.2.1]octane-di-yl.

In one embodiment, -D$^1$-, if present, is independently bicyclo[3.2.1]octane-3,8-di-yl.

In one embodiment, -D$^1$-, if present, is independently bicyclo[3.2.1]octane-8,3-di-yl.

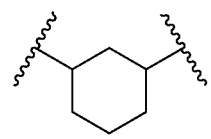 [SMILES: *C1CCCC(*)C1]

bicyclo[3.2.1]octane-3,8-di-yl    bicyclo[3.2.1]octane-8,3-di-yl

In one embodiment, -D$^1$-, if present, is independently bicyclo[3.1.1]heptane-di-yl.

In one embodiment, -D$^1$-, if present, is independently bicyclo[3.1.1]heptane-3,6-di-yl.

In one embodiment, -D$^1$-, if present, is independently bicyclo[3.1.1]heptane-6,3-di-yl.

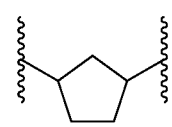

bicyclo[3.1.1]heptane-3,6-di-yl    bicyclo[3.1.1]heptane-6,3-di-yl

For the avoidance of doubt, where no conformation is indicated, all possible conformations are encompassed.

For example, the group described as:

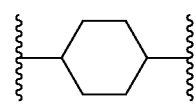

encompasses (at least) the following well known conformations:

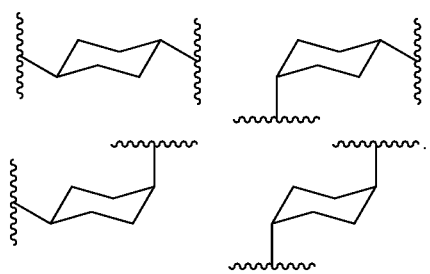

Similarly, the group described as:

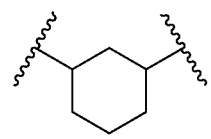 [SMILES: *C1CCCC(*)C1]

encompasses (at least) the following well known conformations:

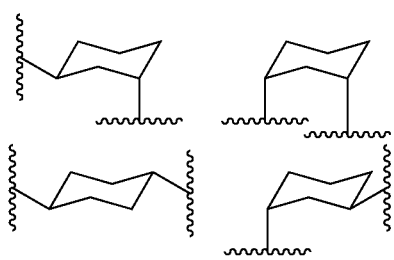

Similarly, the group described as:

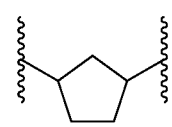

encompasses (at least) the following well known conformations:

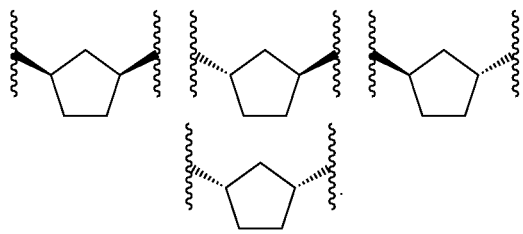

Similarly, the group described as:

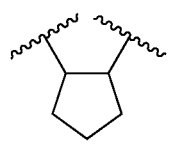 [SMILES: *C1CCCC1*]

encompasses (at least) the following well known conformations:

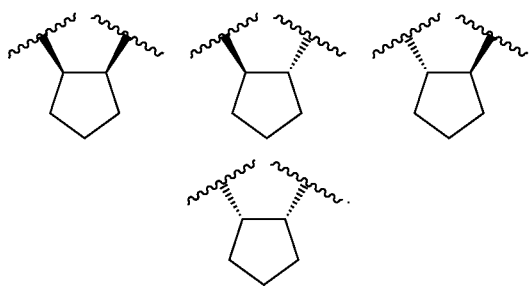

For example, the group described as:

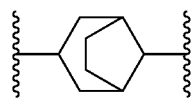

encompasses (at least) the following well known conformations:

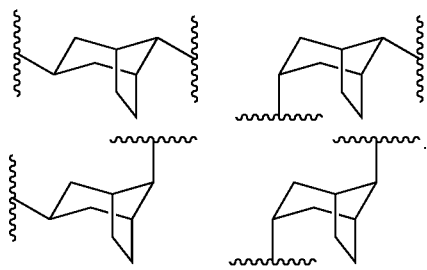

The Group -D²=

In one embodiment, -D²=, if present, is independently cyclopentane-yl-ylidene, cyclohexane-yl-ylidene, cycloheptane-yl-ylidene, bicyclo[3.1.1]heptane-yl-ylidene, or bicyclo[3.2.1]octane-yl-ylidene, and is optionally substituted with one or more groups —R$^D$.

In one embodiment, -D²=, if present, is independently cyclopentane-yl-ylidene, cyclohexane-yl-ylidene, cycloheptane-yl-ylidene, bicyclo[3.1.1]heptane-yl-ylidene, or bicyclo[3.2.1]octane-yl-ylidene.

In one embodiment, -D²=, if present, is independently cyclopentane-yl-ylidene, cyclohexane-yl-ylidene, or cycloheptane-yl-ylidene, and is optionally substituted with one or more groups —R$^D$.

In one embodiment, -D²=, if present, is independently cyclopentane-yl-ylidene, cyclohexane-yl-ylidene, or cycloheptane-yl-ylidene.

In one embodiment, -D²=, if present, is independently cyclopentane-yl-ylidene or cyclohexane-yl-ylidene.

In one embodiment, -D²=, if present, is independently cyclopentane-yl-ylidene.

In one embodiment, -D²=, if present, is independently cyclopentane-1-yl-2-ylidine.

In one embodiment, -D²=, if present, is independently cyclopentane-1-yl-3-ylidene.

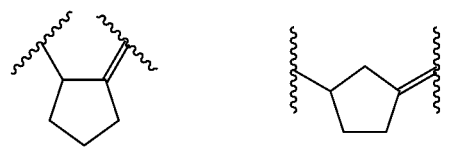

cyclopentane-1-yl-2-ylidene    cyclopentane-1-yl-3-ylidene

In one embodiment, -D²=, if present, is independently cyclohexane-yl-ylidene.

In one embodiment, -D²=, if present, is independently cyclohexane-1-yl-2-ylidine.

In one embodiment, -D²=, if present, is independently cyclohexane-1-yl-3-ylidine.

In one embodiment, -D²=, if present, is independently cyclohexane-1-yl-4-ylidine.

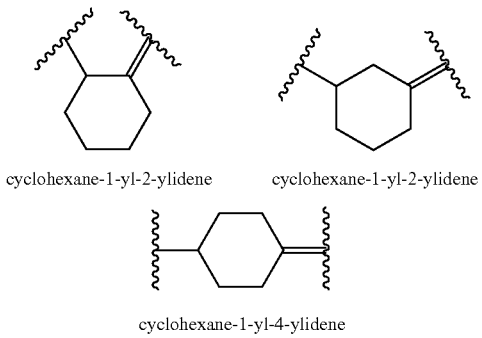

cyclohexane-1-yl-2-ylidene    cyclohexane-1-yl-2-ylidene cyclohexane-1-yl-4-ylidene In one embodiment, -D²=, if present, is independently cycloheptane-yl-ylidene.

In one embodiment, -D²=, if present, is independently cycloheptane-1-yl-2-ylidine.

In one embodiment, -D²=, if present, is independently cycloheptane-1-yl-3-ylidine.

In one embodiment, -D²=, if present, is independently cycloheptane-1-yl-4-ylidine.

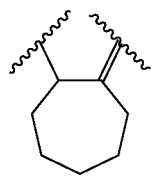 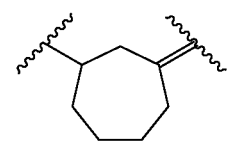

cycloheptane-1-yl-2-ylidene    cycloheptane-1-yl-3-ylidene

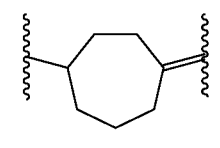

cycloheptane-1-yl-4-ylidene

In one embodiment, -D²=, if present, is independently cyclohexane-1-yl-4-ylidine, and -D²=O is:

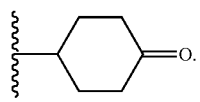

In one embodiment, -D²=, if present, is independently bicyclo[3.2.1]octane-yl-ylidene.
In one embodiment, -D²=, if present, is independently bicyclo[3.2.1]octane-3-yl-8-ylidene.
In one embodiment, -D²=, if present, is independently bicyclo[3.2.1]octane-8-yl-3-ylidene.

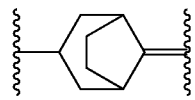 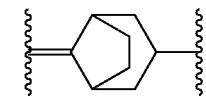

bicyclo[3.2.1]octane-3-yl-8-ylidene   bicyclo[3.2.1]octane-8-yl-3-ylidene

In one embodiment, -D²=, if present, is independently bicyclo[3.1.1]heptane-yl-ylidene.
In one embodiment, -D²=, if present, is independently bicyclo[3.1.1]heptane-3-yl-6-ylidene.
In one embodiment, -D²=, if present, is independently bicyclo[3.1.1]heptane-6-yl-3-ylidene.

 

bicyclo[3.1.1]heptane-3-yl-6-ylidene   bicyclo[3.1.1]heptane-6-yl-3-ylidene

Again, for the avoidance of doubt, where no conformation is indicated, all possible conformations are encompassed.

The Groups —$R^D$

In one embodiment, each —$R^D$, if present, is independently selected from —F, —Cl, —Br, —I, —$R^{DD}$, —$CF_3$, —OH, —$OR^{DD}$, —$NH_2$, —$NHR^{DD}$, and —$NR^{DD}{}_2$, wherein each —$R^{DD}$ is independently saturated aliphatic $C_{1-4}$alkyl.

In one embodiment, each —$R^{DD}$, if present, is independently -Me or -Et.

In one embodiment, each —$R^{DD}$, if present, is independently -Me.

For example, in one embodiment, -D¹-, if present, is independently 4-methyl-cyclohexane-1,4-di-yl.

4-methyl-cyclohexane-1,4-di-yl

The Group -Q¹

In one embodiment, -Q¹, if present, is independently selected from:

 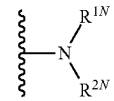 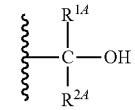 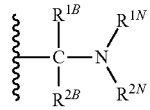

In one embodiment, -Q¹, if present, is independently selected from:

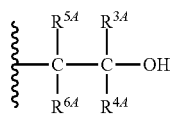 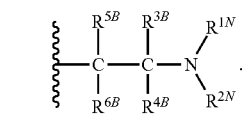

In one embodiment, -Q¹, if present, is independently:

 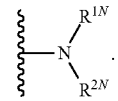

In one embodiment, -Q¹, if present, is independently:

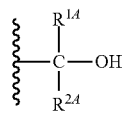 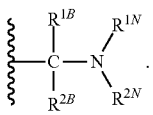

In one embodiment, -Q¹, if present, is independently selected from:

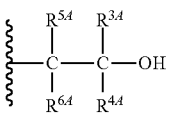 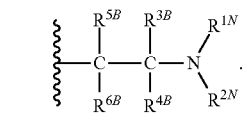

In one embodiment, -Q¹, if present, is independently selected from:

 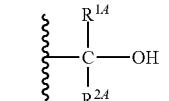 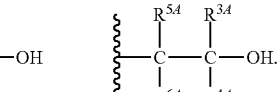

In one embodiment, -Q¹, if present, is independently selected from:

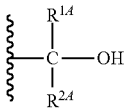 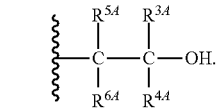

In one embodiment, -Q¹, if present, is independently:

In one embodiment, -Q¹, if present, is independently:

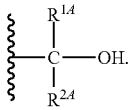

In one embodiment, -$Q^1$, if present, is independently:

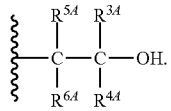

In one embodiment, -$Q^1$, if present, is independently selected from:

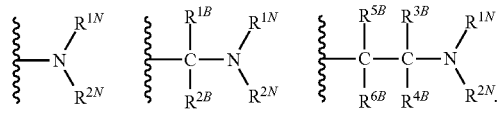

In one embodiment, -$Q^1$, if present, is independently selected from:

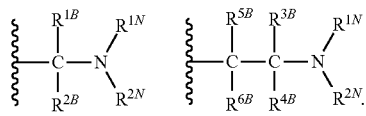

In one embodiment, -$Q^1$, if present, is independently:

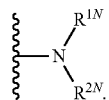

In one embodiment, -$Q^1$, if present, is independently:

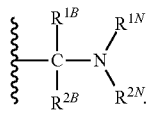

In one embodiment, -$Q^1$, if present, is independently:

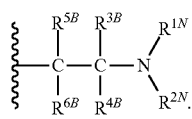

For the avoidance of doubt, where no stereochemistry is indicated, all possible conformations are encompassed.

For example, the group described as —CH(Me)OH or as any of the following:

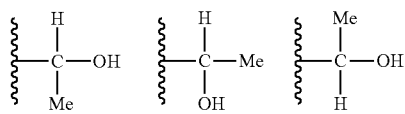

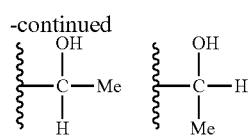

encompasses both stereoisomers:

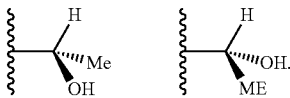

The Groups —$R^{1N}$ and —$R^{2N}$

In one embodiment:
each —$R^{1N}$, if present, is independently —H, —$R^{CN}$, or —$R^{CF}$;
each —$R^{2N}$, if present, is independently —H, —$R^{CN}$, or —$R^{CF}$;
each —$R^{CN}$, if present, is independently saturated aliphatic $C_{1-4}$alkyl; and each —$R^{CF}$, if present, is independently saturated aliphatic $C_{1-4}$fluoroalkyl;
or:
—$NR^{1N}R^{2N}$, if present, is independently azetidino, pyrrolidino, imidazolidino, pyrazolidino, piperidino, piperazino, morpholino, thiomorpholino, azepino, or diazepino, each optionally substituted with one or more groups independently selected from saturated aliphatic $C_{1-4}$alkyl.

In one embodiment:
each —$R^{1N}$, if present, is independently —H or —$R^{CN}$;
each —$R^{2N}$, if present, is independently —H or —$R^{CN}$; and
each —$R^{CN}$, if present, is independently saturated aliphatic $C_{1-4}$alkyl;
or:
—$NR^{1N}R^{2N}$, if present, is independently azetidino, pyrrolidino, imidazolidino, pyrazolidino, piperidino, piperazino, morpholino, thiomorpholino, azepino, or diazepino, each optionally substituted with one or more groups independently selected from saturated aliphatic $C_{1-4}$alkyl.

In one embodiment:
each —$R^{1N}$, if present, is independently —H, —$R^{CN}$, or —$R^{CF}$; and
each —$R^{2N}$, if present, is independently —H, —$R^{CN}$, or —$R^{CF}$.

In one embodiment:
each —$R^{1N}$, if present, is independently —H or —$R^{CN}$; and
each —$R^{2N}$, if present, is independently —H or —$R^{CN}$.

In one embodiment:
each —$R^{1N}$, if present, is independently —H, —$R^{CN}$, or —$R^{CF}$; and
each —$R^{2N}$, if present, is independently —H.

In one embodiment:
each —$R^{1N}$, if present, is independently —H or —$R^{CN}$; and
each —$R^{2N}$, if present, is independently —H.

In one embodiment:
each —$R^{1N}$, if present, is independently —$R^{CN}$ or —$R^{CF}$; and
each —$R^{2N}$, if present, is independently —H.

In one embodiment:
each —$R^{1N}$, if present, is independently —$R^{CN}$; and
each —$R^{2N}$, if present, is independently —H.

In one embodiment:
each —$R^{1N}$, if present, is independently —$R^{CF}$; and
each —$R^{2N}$, if present, is independently —H.

In one embodiment:
each —$R^{1N}$, if present, is independently —$R^{CN}$; and
each —$R^{2N}$, if present, is independently —$R^{CN}$.

In one embodiment:
each —$R^{1N}$, if present, is independently —H; and
each —$R^{2N}$, if present, is independently —H.

In one embodiment —$NR^{1N}R^{2N}$, if present, is independently azetidino, pyrrolidino, imidazolidino, pyrazolidino, piperidino, piperazino, morpholino, thiomorpholino, azepino, or diazepino, each optionally substituted with one or more groups independently selected from saturated aliphatic $C_{1-4}$alkyl.

In one embodiment, —$NR^{1N}R^{2N}$, if present, is independently pyrrolidino, piperidino, piperazino, or morpholino, each optionally substituted with one or more groups independently selected from saturated aliphatic $C_{1-4}$alkyl.

In one embodiment, —$NR^{1N}R^{2N}$, if present, is independently piperidino, piperazino, or morpholino, each optionally substituted with one or more groups independently selected from saturated aliphatic $C_{1-4}$alkyl.

In one embodiment —$NR^{1N}R^{2N}$, if present, is independently pyrrolidino or morpholino.

In one embodiment —$NR^{1N}R^{2N}$, if present, is independently morpholino.

In one embodiment, each —$R^{CN}$, if present, is independently -Me or -Et.

In one embodiment, each —$R^{CN}$, if present, is independently -Me.

In one embodiment, each —$R^{CF}$, if present, is independently —$CF_3$, —$CH_2CF_3$, or —$CH_2CH_2F$.

In one embodiment, each —$R^{CF}$, if present, is independently —$CF_3$.

In one embodiment, —$NR^{1N}R^{2N}$, if present, is independently —$NH_2$, —NHMe, —$NMe_2$, —NHEt, —$NEt_2$, —NMeEt, —NH(iPr), —$NH(CH_2CF_3)$, pyrrolidino, or morpholino.

In one embodiment, —$NR^{1N}R^{2N}$, if present, is independently —$NH_2$, —NHMe, —$NMe_2$, or morpholino.

The Groups —$R^{1A}$ and —$R^{2A}$

In one embodiment:
—$R^{1A}$, if present, is independently —H, —$R^C$, or —$R^F$; and
—$R^{2A}$, if present, is independently —H, —$R^C$, or —$R^F$;
or —$R^{1A}$ and —$R^{2A}$, if present, together form a saturated aliphatic $C_{2-4}$alkylene group.

In one embodiment:
—$R^{1A}$, if present, is independently —H, —$R^C$, or —$R^F$; and
—$R^{2A}$, if present, is independently —H, —$R^C$, or —$R^F$.

In one embodiment:
—$R^{1A}$, if present, is independently —H or —$R^C$; and
—$R^{2A}$, if present, is independently —H or —$R^C$.

In one embodiment:
—$R^{1A}$, if present, is independently —H or —$R^C$; and
—$R^{2A}$, if present, is independently —H.

In one embodiment:
—$R^{1A}$, if present, is independently —$R^C$; and
—$R^{2A}$, if present, is independently —H.

In one embodiment:
—$R^{1A}$, if present, is independently —$R^C$; and
—$R^{2A}$, if present, is independently —$R^C$.

In one embodiment:
—$R^{1A}$, if present, is independently —H; and
—$R^{2A}$, if present, is independently —H.

In one embodiment, —$R^{1A}$ and —$R^{2A}$, if present, together form a saturated aliphatic $C_{2-4}$alkylene group.

In one embodiment, —$R^{1A}$ and —$R^{2A}$, if present, together form —$CH_2CH_2$—, —$CH_2CH_2CH_2$—, or —$CH_2CH_2CH_2CH_2$—.

In one embodiment, —$R^{1A}$ and —$R^{2A}$, if present, together form —$CH_2CH_2$—.

The Groups —$R^{1B}$ and —$R^{2B}$

In one embodiment:
—$R^{1B}$ is independently —H, —$R^C$, or —$R^F$; and
—$R^{2B}$ is independently —H, —$R^C$, or —$R^F$;
or —$R^{1B}$ and —$R^{2B}$ together form a saturated aliphatic $C_{2-4}$alkylene group;
or —$R^{1B}$ and —$R^{2B}$ together form =O.

In one embodiment:
—$R^{1B}$, if present, is independently —H, —$R^C$, or —$R^F$; and
—$R^{2B}$, if present, is independently —H, —$R^C$, or —$R^F$;
or —$R^{1B}$ and —$R^{2B}$, if present, together form a saturated aliphatic $C_{2-4}$alkylene group.

In one embodiment:
—$R^{1B}$, if present, is independently —H, —$R^C$, or —$R^F$; and
—$R^{2B}$, if present, is independently —H, —$R^C$, or —$R^F$.

In one embodiment:
—$R^{1B}$, if present, is independently —H or —$R^C$; and
—$R^{2B}$, if present, is independently —H or —$R^C$.

In one embodiment:
—$R^{1B}$, if present, is independently —H or —$R^C$; and
—$R^{2B}$, if present, is independently —H.

In one embodiment:
—$R^{1B}$, if present, is independently —$R^C$; and
—$R^{2B}$, if present, is independently —H.

In one embodiment:
—$R^{1B}$, if present, is independently —$R^C$; and
—$R^{2B}$, if present, is independently —$R^C$.

In one embodiment:
—$R^{1B}$, if present, is independently —H; and
—$R^{2B}$, if present, is independently —H.

In one embodiment, —$R^{1B}$ and —$R^{2B}$, if present, together form a saturated aliphatic $C_{2-4}$alkylene group.

In one embodiment, —$R^{1B}$ and —$R^{2B}$, if present, together form —$CH_2CH_2$—, —$CH_2CH_2CH_2$—, or —$CH_2CH_2CH_2CH_2$—.

In one embodiment, —$R^{1B}$ and —$R^{2B}$, if present, together form —$CH_2CH_2$—.

In one embodiment, —$R^{1B}$ and —$R^{2B}$, if present, together form =O.

The Groups —$R^{3A}$ and —$R^{4A}$

In one embodiment:
—$R^{3A}$, if present, is independently —H, —$R^C$, or —$R^F$; and
—$R^{4A}$, if present, is independently —H, —$R^C$, or —$R^F$;
or —$R^{3A}$ and —$R^{4A}$, if present, together form a saturated aliphatic $C_{2-4}$alkylene group.

In one embodiment:
—$R^{3A}$, if present, is independently —H, —$R^C$, or —$R^F$; and
—$R^{4A}$, if present, is independently —H, —$R^C$, or —$R^F$.

In one embodiment:
—$R^{3A}$, if present, is independently —H or —$R^C$; and
—$R^{4A}$, if present, is independently —H or —$R^C$.

In one embodiment:
—$R^{3A}$, if present, is independently —H or —$R^C$; and
—$R^{4A}$, if present, is independently —H.
In one embodiment:
—$R^{3A}$, if present, is independently —$R^C$; and
—$R^{4A}$, if present, is independently —H.
In one embodiment:
—$R^{3A}$, if present, is independently —$R^C$; and
—$R^{4A}$, if present, is independently —$R^C$.
In one embodiment:
—$R^{3A}$, if present, is independently —H; and
—$R^{4A}$, if present, is independently —H.
In one embodiment, —$R^{3A}$ and —$R^{4A}$, if present, together form a saturated aliphatic $C_{2-4}$alkylene group.
In one embodiment, —$R^{3A}$ and —$R^{4A}$, if present, together form —$CH_2CH_2$—, —$CH_2CH_2CH_2$—, or —$CH_2CH_2CH_2CH_2$—.
In one embodiment, —$R^{3A}$ and —$R^{4A}$, if present, together form —$CH_2CH_2$—.

The Groups —$R^{5A}$ and —$R^{6A}$

In one embodiment:
—$R^{5A}$, if present, is independently —H, —$R^C$, —$R^F$, or —$R^J$; and
—$R^{6A}$, if present, is independently —H, —$R^C$, or —$R^F$; or —$R^{5A}$ and —$R^{6A}$, if present, together form a saturated aliphatic $C_{2-4}$alkylene group.
In one embodiment:
—$R^{5A}$, if present, is independently —H, —$R^C$, or —$R^J$; and
—$R^{6A}$, if present, is independently —H or —$R^C$.
In one embodiment:
—$R^{5A}$, if present, is independently —$R^J$; and
—$R^{6A}$, if present, is independently —H or —$R^C$.
In one embodiment:
—$R^{5A}$, if present, is independently —$R^J$; and
—$R^{6A}$, if present, is independently —H.
In one embodiment:
—$R^{5A}$, if present, is independently —$R^J$; and
—$R^{6A}$, if present, is independently —$R^C$.
In one embodiment:
—$R^{5A}$, if present, is independently —H or —$R^C$; and
—$R^{6A}$, if present, is independently —H or —$R^C$.
In one embodiment:
—$R^{5A}$, if present, is independently —H or —$R^C$; and
—$R^{6A}$, if present, is independently —H.
In one embodiment:
—$R^{5A}$, if present, is independently —$R^C$; and
—$R^{6A}$, if present, is independently —H.
In one embodiment:
—$R^{5A}$, if present, is independently —$R^C$; and
—$R^{6A}$, if present, is independently —$R^C$.
In one embodiment:
—$R^{5A}$, if present, is independently —H; and
—$R^{6A}$, if present, is independently —H.
In one embodiment, —$R^{5A}$ and —$R^{6A}$, if present, together form a saturated aliphatic $C_{2-4}$alkylene group.
In one embodiment, —$R^{5A}$ and —$R^{6A}$, if present, together form —$CH_2CH_2$—, —$CH_2CH_2CH_2$—, or —$CH_2CH_2CH_2CH_2$—.
In one embodiment, —$R^{5A}$ and —$R^{6A}$, if present, together form —$CH_2CH_2$—.

The Groups —$R^{3B}$ and —$R^{4B}$

In one embodiment:
—$R^{3B}$, if present, is independently —H, —$R^C$, or —$R^F$; and
—$R^{4B}$, if present, is independently —H, —$R^C$, or —$R^F$; or —$R^{3B}$ and —$R^{4B}$, if present, together form a saturated aliphatic $C_{2-4}$alkylene group.
In one embodiment:
—$R^{3B}$, if present, is independently —H, —$R^C$, or —$R^F$; and
—$R^{4B}$, if present, is independently —H, —$R^C$, or —$R^F$.
In one embodiment:
—$R^{3B}$, if present, is independently —H or —$R^C$; and
—$R^{4B}$, if present, is independently —H or —$R^C$.
In one embodiment:
—$R^{3B}$, if present, is independently —H or —$R^C$; and
—$R^{4B}$, if present, is independently —H.
In one embodiment:
—$R^{3B}$, if present, is independently —$R^C$; and
—$R^{4B}$, if present, is independently —H.
In one embodiment:
—$R^{3B}$, if present, is independently —$R^C$; and
—$R^{4B}$, if present, is independently —$R^C$.
In one embodiment:
—$R^{3B}$, if present, is independently —H; and
—$R^{4B}$, if present, is independently —H.
In one embodiment, —$R^{3B}$ and —$R^{4B}$, if present, together form a saturated aliphatic $C_{2-4}$alkylene group.
In one embodiment, —$R^{3B}$ and —$R^{4B}$, if present, together form —$CH_2CH_2$—, —$CH_2CH_2CH_2$—, or —$CH_2CH_2CH_2CH_2$—.
In one embodiment, —$R^{3B}$ and —$R^{4B}$, if present, together form —$CH_2CH_2$—.

The Groups —$R^{5B}$ and —$R^{6B}$

In one embodiment:
—$R^{5B}$, if present, is independently —H, —$R^C$, —$R^F$, —OH, or —$OR^C$; and
—$R^{6B}$, if present, is independently —H, —$R^C$, or —$R^F$; or —$R^{5B}$ and —$R^{6B}$, if present, together form a saturated aliphatic $C_{2-4}$alkylene group.
In one embodiment:
—$R^{5B}$, if present, is independently —H, —$R^C$, —$R^F$, —OH, or —$OR^C$; and
—$R^{6B}$, if present, is independently —H, —$R^C$, or —$R^F$.
In one embodiment:
—$R^{5B}$, if present, is independently —H, —$R^C$, —OH, or —$OR^C$; and
—$R^{6B}$, if present, is independently —H or —$R^C$.
In one embodiment:
—$R^{5B}$, if present, is independently —OH or —$OR^C$; and
—$R^{6B}$, if present, is independently —H or —$R^C$.
In one embodiment:
—$R^{5B}$, if present, is independently —OH or —$OR^C$; and
—$R^{6B}$, if present, is independently —H.
In one embodiment:
—$R^{5B}$, if present, is independently —OH; and
—$R^{6B}$, if present, is independently —H.
In one embodiment:
—$R^{5B}$, if present, is independently —H or —$R^C$; and
—$R^{6B}$, if present, is independently —H or —$R^C$.
In one embodiment:
—$R^{5B}$, if present, is independently —H or —$R^C$; and
—$R^{6B}$, if present, is independently —H.
In one embodiment:
—$R^{5B}$, if present, is independently —H; and
—$R^{6B}$, if present, is independently —$R^C$.
In one embodiment:
—$R^{5B}$, if present, is independently —$R^C$; and
—$R^{6B}$, if present, is independently —$R^C$.
In one embodiment:
—$R^{5B}$, if present, is independently —H; and
—$R^{6B}$, if present, is independently —H.

In one embodiment, —R$^{5B}$ and —R$^{6B}$, if present, together form a saturated aliphatic C$_{2-4}$alkylene group.

In one embodiment, —R$^{5B}$ and —R$^{6B}$, if present, together form —CH$_2$CH$_2$—, —CH$_2$CH$_2$CH$_2$—, or —CH$_2$CH$_2$CH$_2$CH$_2$—.

In one embodiment, —R$^{5B}$ and —R$^{6B}$, if present, together form —CH$_2$CH$_2$—.

The Group —R$^O$

In one embodiment, —R$^O$, if present, is independently saturated aliphatic C$_{1-4}$alkyl.

In one embodiment, —R$^O$, if present, is independently -Me or -Et.

In one embodiment, —R$^O$, if present, is independently -Me.

The Group —R$^C$

In one embodiment, each —R$^C$, if present, is independently saturated aliphatic C$_{1-4}$alkyl.

In one embodiment, each —R$^C$, if present, is independently -Me or -Et.

In one embodiment, each —R$^C$, if present, is independently -Me.

The Group —R$^F$

In one embodiment, each —R$^F$, if present, is independently saturated aliphatic C$_{1-4}$fluoroalkyl.

In one embodiment, each —R$^F$, if present, is independently —CF$_3$, —CH$_2$CF$_3$, or —CH$_2$CH$_2$F.

In one embodiment, each —R$^F$, if present, is independently —CF$_3$.

The Group —R$^J$

In one embodiment, —R$^J$, if present, is independently —NH$_2$, —NHR$^{JN1}$, —NR$^{JN1}$$_2$, or —NR$^{JN2}$R$^{JN3}$.

In one embodiment, —R$^J$, if present, is independently —NH$_2$, —NHR$^{JN1}$, or —NR$^{JN1}$$_2$.

In one embodiment, —R$^J$, if present, is independently —NH$_2$.

In one embodiment, —R$^J$, if present, is independently —NHR$^{JN1}$.

In one embodiment, —R$^J$, if present, is independently —NR$^{JN1}$$_2$.

In one embodiment, —R$^J$, if present, is independently —NR$^{JN2}$R$^{JN3}$.

In one embodiment, each —R$^{JN1}$, if present, is independently saturated aliphatic C$_{1-4}$alkyl.

In one embodiment, each —R$^{JN1}$, if present, is independently -Me, -Et, or -iPr.

In one embodiment, each —R$^{JN1}$, if present, is independently -Me or -Et.

In one embodiment, each —R$^{JN1}$, if present, is independently -Me.

In one embodiment, —NR$^{JN2}$R$^{JN3}$, if present, is independently azetidino, pyrrolidino, imidazolidino, pyrazolidino, piperidino, piperazino, morpholino, thiomorpholino, azepino, or diazepino, each optionally substituted with one or more groups independently selected from saturated aliphatic C$_{1-4}$alkyl.

In one embodiment, —NR$^{JN2}$R$^{JN3}$, if present, is independently piperidino, piperazino, or morpholino, each optionally substituted with one or more groups independently selected from saturated aliphatic C$_{1-4}$alkyl.

In one embodiment, —NR$^{JN2}$R$^{JN3}$, if present, is independently morpholino.

In one embodiment, —R$^J$, if present, is independently —NH$_2$, —NHMe, —NMe$_2$, —NHEt, —NEt$_2$, —NH(nPr), —N(nPr)$_2$, —NH(iPr), —N(iPr)$_2$, piperidino, piperazino, or morpholino.

In one embodiment, —R$^J$, if present, is independently —NH$_2$, —NHMe, —NMe$_2$, or morpholino.

In one embodiment, —R$^J$, if present, is independently —NH$_2$, —NHMe, or —NMe$_2$.

The Group -Q$^1$: Some Preferred Embodiments

In one embodiment, -Q$^1$, if present, is independently —OH, —CH$_2$OH, —CH(Me)OH, —C(Me)$_2$OH, —NH$_2$, —NHMe, —NMe$_2$, —NHEt, —NEt$_2$, —NMeEt, —NH(iPr), pyrrolidino, morpholino, —NHCH$_2$CF$_3$, —CH$_2$NH$_2$, —CH$_2$NHMe, —CH$_2$NMe$_2$, —CH$_2$NHEt, —CH$_2$NEt$_2$, —CH(NHMe)CH$_2$OH, —C(=O)NH$_2$, —C(=O)NHMe, —C(=O)NMe$_2$, —C(=O)NHEt, or —C(=O)NEt$_2$.

In one embodiment, -Q$^1$, if present, is independently —OH, —CH$_2$OH, —CH(Me)OH, —C(Me)$_2$OH, —NH$_2$, —NHMe, —NMe$_2$, —NHEt, —NEt$_2$, or —CH(NHMe)CH$_2$OH.

In one embodiment, -Q$^1$, if present, is independently —OH, —CH$_2$OH, —CH(Me)OH, or —C(Me)$_2$OH.

In one embodiment, -Q$^1$, if present, is independently —OH.

In one embodiment, -Q$^1$, if present, is independently —CH$_2$OH, —CH(Me)OH, or —C(Me)$_2$OH.

In one embodiment, -Q$^1$, if present, is independently —CH$_2$OH.

In one embodiment, -Q$^1$, if present, is independently —NH$_2$, —NHMe, —NMe$_2$, —NHEt, —NEt$_2$, —NMeEt, —NH(iPr), pyrrolidino, morpholino, —NHCH$_2$CF$_3$, —CH$_2$NH$_2$, —CH$_2$NHMe, —CH$_2$NMe$_2$, —CH$_2$NHEt, —CH$_2$NEt$_2$, —CH(NHMe)CH$_2$OH, —C(=O)NH$_2$, —C(=O)NHMe, —C(=O)NMe$_2$, —C(=O)NHEt, or —C(=O)NEt$_2$.

In one embodiment, -Q$^1$, if present, is independently —NH$_2$, —NHMe, —NMe$_2$, —NHEt, —NEt$_2$, —NMeEt, —NH(iPr), pyrrolidino, morpholino, —NHCH$_2$CF$_3$, —CH$_2$NH$_2$, —CH$_2$NHMe, —CH$_2$NMe$_2$, —CH$_2$NHEt, —CH$_2$NEt$_2$, or —CH(NHMe)CH$_2$OH.

In one embodiment, -Q$^1$, if present, is independently —NH$_2$, —NHMe, —NMe$_2$, —NHEt, or —NEt$_2$.

The Group —R$^{SN}$

In one embodiment, —R$^{SN}$ is independently —H or saturated aliphatic C$_{1-4}$alkyl.

In one embodiment, —R$^{SN}$ is independently —H, -Me, or -Et.

In one embodiment, —R$^{SN}$ is independently —H.

Some Preferred Combinations

In one preferred embodiment:

-A is independently:

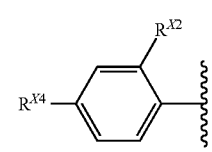

-DQ is independently -D$^1$-Q$^1$;

-D$^1$- is independently cyclopentane-di-yl or cyclohexane-di-yl.

In one preferred embodiment:

-A is independently:

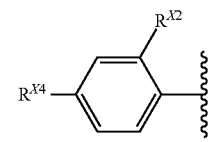

-DQ is independently -D$^1$-Q$^1$;

-D$^1$- is independently cyclopentane-di-yl or cyclohexane-di-yl; and

-Q¹ is independently —OH, —CH₂OH, —CH(Me)OH, —C(Me)₂OH, —NH₂, —NHMe, —NMe₂, —NHEt, —NEt₂, or —CH(NHMe)CH₂OH.

In one preferred embodiment:
-A is independently:

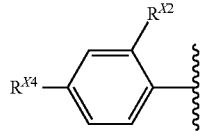

-DQ is independently -D¹-Q¹;
-D¹- is independently cyclopentane-di-yl or cyclohexane-di-yl; and
-Q¹ is independently —OH.

In one preferred embodiment:
-A is independently:

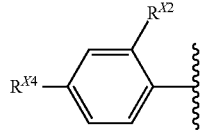

-DQ is independently -D¹-Q¹;
-D¹- is independently cyclohexane-di-yl; and
-Q¹ is independently —OH.

In one preferred embodiment:
-A is independently:

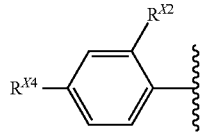

-DQ is independently -D¹-Q¹;
-D¹- is independently cyclopentane-di-yl or cyclohexane-di-yl; and
-Q¹ is independently —CH₂OH, —CH(Me)OH, or —C(Me)₂OH.

In one preferred embodiment:
-A is independently:

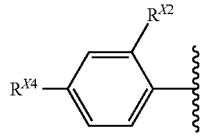

-DQ is independently -D¹-Q¹;
-D¹- is independently cyclopentane-di-yl or cyclohexane-di-yl; and
-Q¹ is independently —CH₂OH.

In one preferred embodiment:
-A is independently:

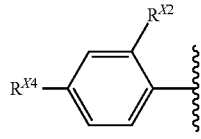

-DQ is independently -D¹-Q¹;
-D¹- is independently cyclopentane-di-yl or cyclohexane-di-yl; and
-Q¹ is independently —NH₂, —NHMe, —NMe₂, —NHEt, —NEt₂.

In one preferred embodiment:
-A is independently:

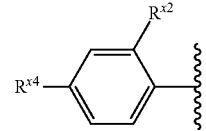

-DQ is independently -D¹-Q¹;
-D¹- is independently cyclopentane-di-yl or cyclohexane-di-yl; and
-Q¹ is independently —CH(NHMe)CH₂OH.

In other preferred embodiments, additionally:
—R$^{X2}$ is independently —F or —Cl; and
—R$^{X4}$ is independently —F or —Cl.

In other preferred embodiments, additionally:
—R$^{X2}$ is independently —F or —Cl;
—R$^{X4}$ is independently —F or —Cl; and
—R$^{SN}$ is independently —H or -Me.

In other preferred embodiments, additionally:
—R$^{X2}$ is independently —F;
—R$^{X4}$ is independently —F; and
—R$^{SN}$ is independently —H.

In other preferred embodiments, additionally, —R$^J$, if present, is independently —NH₂, —NHMe, —NMe₂, —NHEt, —NEt₂, —NH(nPr), —N(nPr)₂, —NH(iPr), —N(iPr)₂, piperidino, piperazino, or morpholino.

In other preferred embodiments, additionally, —R$^J$, if present, is independently —NH₂, —NHMe, —NMe₂, or morpholino.

In other preferred embodiments, additionally, —R$^J$, if present, is independently —NH₂, —NHMe, or —NMe₂.

Molecular Weight

In one embodiment, the APSAC compound has a molecular weight of from 317 to 1200.

In one embodiment, the bottom of range is 325, 350, 375, 400, 425, 450, 500.

In one embodiment, the top of range is 1100, 1000, 900, 800, 700, or 600.

In one embodiment, the range is from 350 to 700.

Combinations

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the chemical groups represented by the variables (e.g., -A, —Ar, p, —R$^X$, q, —R$^{SN}$, -D$^Q$, -D¹-, -Q¹, -D²=, —R$^D$, —R$^{DD}$, —R$^{1A}$, —R$^{2A}$, —R$^{3A}$, —R$^{4A}$, —R$^{5A}$, —R$^{6A}$, —R$^{1B}$, —R$^{2B}$, —R$^{3B}$, —R$^{4B}$, —R$^{5B}$, —R$^{6B}$, —R$^{1N}$, —R$^{2N}$, —R$^{CN}$, —R$^{CF}$, —NR$^{1N}$R$^{2N}$, —R$^C$, —R$^F$, —R$^J$, —R$^O$, —R$^{JN1}$, —NR$^{JN2}$R$^{JN3}$, —R$^{XX}$, —NR$^{YY}$R$^{ZZ}$, —R$^{XXX}$, =W—, =Y=, —R$^W$, —R$^Y$, —R$^{X2}$, —R$^{X3}$, —R$^{X4}$, —R$^{X2S}$, —R$^{X3S}$, —R$^{X4S}$, —R$^{X4}$, etc.) are specifically embraced by the present invention and are disclosed herein just as if each and every combination was individually and explicitly disclosed, to the extent that such combinations embrace compounds that are stable compounds (i.e., compounds that can be isolated, characterised, and tested for biological activity). In addition, all sub-combinations of the chemical groups listed in the embodiments describing such variables are also specifically embraced by the present invention and are disclosed herein just as if each and every such sub-combination of chemical groups was individually and explicitly disclosed herein.

Specific Embodiments

In one embodiment, the compounds are selected from compounds of the following formulae and pharmaceutically acceptable salts, hydrates, and solvates thereof:

| Compound No. | Structure |
|---|---|
| ABD599 | 2',4'-difluoro-biphenyl-4-sulfonic acid (4-hydroxy-cyclohexyl)-amide |
| ABD655 | 4'-chloro-2'-fluoro-biphenyl-4-sulfonic acid (4-hydroxy-cyclohexyl)-amide |
| ABD665 | 2-fluoro-4'-trifluoromethoxy-biphenyl-4-sulfonic acid (4-hydroxy-cyclohexyl)-amide |
| ABD679 | 2',5'-difluoro-biphenyl-4-sulfonic acid (4-hydroxy-cyclohexyl)-amide |
| ABD682 | 2'-chloro-biphenyl-4-sulfonic acid (4-hydroxy-cyclohexyl)-amide |
| ABD683 | 3'-trifluoromethyl-biphenyl-4-sulfonic acid (4-hydroxy-cyclohexyl)-amide |
| ABD684 | 4'-methyl-3-trifluoromethoxy-biphenyl-4-sulfonic acid (4-hydroxy-cyclohexyl)-amide |
| ABD698 | 2',4'-difluoro-3-trifluoromethoxy-biphenyl-4-sulfonic acid (4-hydroxy-cyclohexyl)-amide |
| ABD699 | 2',4'-difluoro-3-methyl-biphenyl-4-sulfonic acid (4-hydroxy-cyclohexyl)-amide |

-continued

| Compound No. | Structure |
|---|---|
| ABD702 | 4'-fluoro-2-methyl-biphenyl-4-sulfonic acid (4-hydroxy-cyclohexyl)-amide |
| ABD703 | 4'-cyano-2-methyl-biphenyl-4-sulfonic acid (4-hydroxy-cyclohexyl)-amide |
| ABD704 | 3-chloro-4'-methyl-biphenyl-4-sulfonic acid (4-hydroxy-cyclohexyl)-amide |
| ABD705 | 3-chloro-2',4'-difluoro-biphenyl-4-sulfonic acid (4-hydroxy-cyclohexyl)-amide |
| ABD706 | 4'-ethoxy-2-fluoro-biphenyl-4-sulfonic acid (4-hydroxy-cyclohexyl)-amide |
| ABD710 | 2-fluoro-4'-methoxy-biphenyl-4-sulfonic acid (4-hydroxy-cyclohexyl)-amide |
| ABD712 | 4'-chloro-3'-trifluoromethyl-biphenyl-4-sulfonic acid (4-hydroxy-cyclohexyl)-amide |
| ABD714 | 2-fluoro-4'-trifluoromethyl-biphenyl-4-sulfonic acid (4-hydroxy-cyclohexyl)-amide |
| ABD716 | 4'-acetyl-3-chloro-biphenyl-4-sulfonic acid (4-hydroxy-cyclohexyl)-amide |
| ABD730 | 3-ethyl-2',4'-difluoro-biphenyl-4-sulfonic acid (4-hydroxy-cyclohexyl)-amide |

-continued

| Compound No. | Structure |
|---|---|
| ABD732 | 4'-cyano-3-chloro-biphenyl-4-sulfonic acid (4-hydroxy-cyclohexyl)-amide |
| ABD735 | 2',4'-difluoro-2-methyl-biphenyl-4-sulfonic acid (4-hydroxy-cyclohexyl)-amide |
| ABD742 | 4'-trifluoromethoxy-2-methyl-biphenyl-4-sulfonic acid (4-hydroxy-cyclohexyl)-amide |
| ABD756 | 2',4'-dichloro-3-trifluoromethoxy-biphenyl-4-sulfonic acid (4-hydroxy-cyclohexyl)-amide |
| ABD777 | 2',4'-difluoro-biphenyl-4-sulfonic acid (4-hydroxy-cyclohexyl)-amide |
| ABD827 | 2',4'-difluoro-biphenyl-4-sulfonic acid (3-hydroxy-cycloheptyl)-amide |
| ABD828 | 2',4'-difluoro-biphenyl-4-sulfonic acid (4-hydroxy-cycloheptyl)-amide |
| ABD836 | 3,5-dichloro-pyridine-biphenyl-sulfonic acid (4-hydroxy-cyclohexyl)-amide |
| ABD837 | 5-chloro-pyrimidine-biphenyl-sulfonic acid (4-hydroxy-cyclohexyl)-amide |
| ABD839 | 2',4'-difluoro-biphenyl-4-sulfonic acid (3-hydroxy-cyclohexyl)-amide |

| Compound No. | Structure |
|---|---|
| ABD845 | 2,4-difluoro-biphenyl-4'-sulfonamide linked to (1S,3R)-3-hydroxycyclopentyl |
| ABD861 | 5-(pyrimidin-5-yl)-benzenesulfonamide linked to trans-4-hydroxycyclohexyl |

In one embodiment, the compounds are selected from compounds of the following formulae and pharmaceutically acceptable salts, hydrates, and solvates thereof:

| Compound No. | Structure |
|---|---|
| ABD769 | 2',4'-difluoro-biphenyl-4-sulfonamide linked to (1R,2S)-2-(hydroxymethyl)cyclopentyl |
| ABD770 | 2',4'-difluoro-biphenyl-4-sulfonamide linked to (1S,2R)-2-(hydroxymethyl)cyclopentyl |
| ABD771 | 2',4'-difluoro-biphenyl-4-sulfonamide linked to (1S,2S)-2-(hydroxymethyl)cyclopentyl |
| ABD772 | 2',4'-difluoro-biphenyl-4-sulfonamide linked to (1R,2R)-2-(hydroxymethyl)cyclopentyl |
| ABD773 | 2',4'-difluoro-biphenyl-4-sulfonamide linked to (1S,3R)-3-(hydroxymethyl)cyclopentyl |
| ABD774 | 2',4'-difluoro-biphenyl-4-sulfonamide linked to (1R,3S)-3-(hydroxymethyl)cyclopentyl |

-continued
| Compound No. | Structure |
|---|---|
| ABD775 | 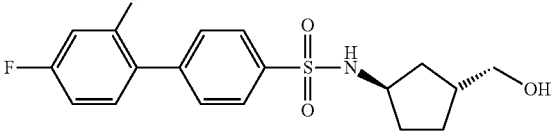 |
| ABD776 | 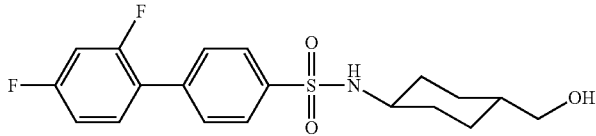 [SMILES: O=S(=O)(NC1CCC(CO)CC1)c1ccc(-c2ccc(F)cc2F)cc1] |
| ABD781 | 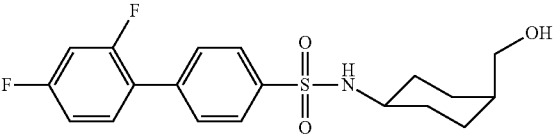 |
| ABD794 | 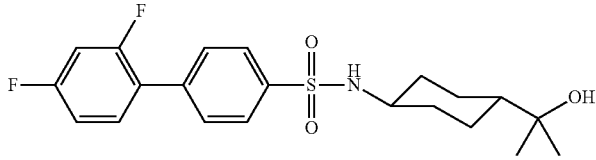 [SMILES: CC(C)(O)C1CCC(NS(=O)(=O)c2ccc(-c3ccc(F)cc3F)cc2)CC1] |
| ABD795 | 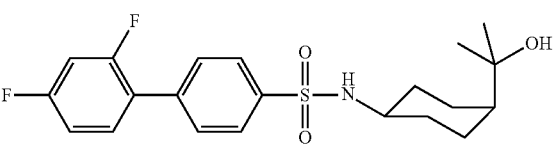 [SMILES: CC(C)(O)C1CCC(NS(=O)(=O)c2ccc(-c3ccc(F)cc3F)cc2)CC1] |
| ABD796 | 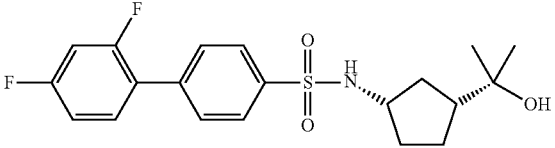 |
| ABD797 | 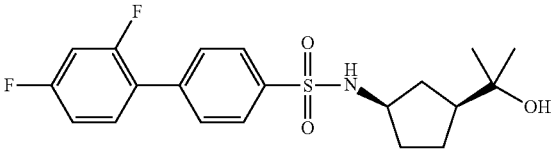 [SMILES: CC(C)(O)[C@H]1CC[C@@H](NS(=O)(=O)c2ccc(-c3ccc(F)cc3F)cc2)C1] |
| ABD813 | 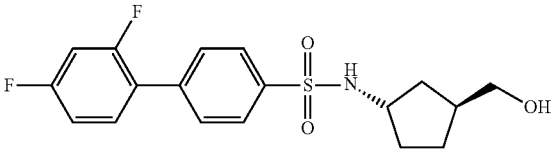 |
| ABD814 | 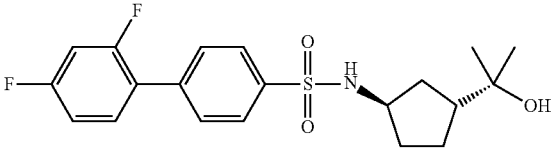 |

| Compound No. | Structure |
|---|---|
| ABD815 | ![structure: 2,4-difluorobiphenyl sulfonamide linked to cyclopentyl-C(CH3)2OH] |
| ABD840 | ![structure: 3,5-dichloropyridyl-phenyl sulfonamide linked to cyclopentyl-CH2OH] |
| ABD841 | ![structure: 3,5-dichloropyridyl-phenyl sulfonamide linked to cyclohexyl-CH2OH] |
| ABD846 | ![structure: 2,4-difluorobiphenyl sulfonamide linked to cyclohexyl-OH] |
| ABD863 | ![structure: 3,5-dichloropyridyl-phenyl sulfonamide linked to cyclohexyl-CH2OH] |

In one embodiment, the compounds are selected from compounds of the following formulae and pharmaceutically acceptable salts, hydrates, and solvates thereof:

| Compound No | Structure |
|---|---|
| ABD787 | ![structure: 2,4-difluorobiphenyl sulfonamide linked to cyclohexyl-NH2] |
| ABD798 | ![structure: 2,4-difluorobiphenyl sulfonamide linked to cyclohexyl-N(CH3)2] |
| ABD799 | ![structure: 2,4-difluorobiphenyl sulfonamide linked to cyclohexyl-N(CH3)2] |

-continued

| Compound No | Structure |
|---|---|
| ABD812 | 2',4'-difluorobiphenyl-4-sulfonamide with N-(4-aminocyclohexyl) group |
| ABD816 | 2',4'-difluorobiphenyl-4-sulfonamide with N-(4-(methylamino)cyclohexyl) group |
| ABD817 | 2',4'-difluorobiphenyl-4-sulfonamide with N-(4-(ethylamino)cyclohexyl) group |
| ABD818 | 2',4'-difluorobiphenyl-4-sulfonamide with N-(4-(isopropylamino)cyclohexyl) group |
| ABD819 | 2',4'-difluorobiphenyl-4-sulfonamide with N-(4-(diethylamino)cyclohexyl) group |
| ABD820 | 2',4'-difluorobiphenyl-4-sulfonamide with N-(4-(pyrrolidin-1-yl)cyclohexyl) group |
| ABD821 | 2',4'-difluorobiphenyl-4-sulfonamide with N-(4-morpholinocyclohexyl) group |
| ABD822 | 2',4'-difluorobiphenyl-4-sulfonamide with N-(4-(ethyl(methyl)amino)cyclohexyl) group |
| ABD864 | 2',4'-difluorobiphenyl-4-sulfonamide with N-(3-((2,2,2-trifluoroethyl)amino)cyclohexyl) group |
| ABD865 | 2',4'-difluorobiphenyl-4-sulfonamide with N-(4-((2,2,2-trifluoroethyl)amino)cyclohexyl) group |

In one embodiment, the compounds are selected from compounds of the following formulae and pharmaceutically acceptable salts, hydrates, and solvates thereof:

| Compound No. | Structure |
| --- | --- |
| ABD823 | 2,4-difluorobiphenyl-4'-sulfonamide linked to cyclopentane with CH₂NHMe substituent (trans stereochemistry) |
| ABD824 | 2,4-difluorobiphenyl-4'-sulfonamide linked to cyclohexane with CH₂NHMe substituent |
| ABD825 | 2,4-difluorobiphenyl-4'-sulfonamide linked to cyclopentane with CH₂NMe₂ substituent (trans stereochemistry) |
| ABD826 | 2,4-difluorobiphenyl-4'-sulfonamide linked to cyclohexane with CH₂NMe₂ substituent |

In one embodiment, the compounds are selected from compounds of the following formulae and pharmaceutically acceptable salts, hydrates, and solvates thereof:

| Compound No. | Structure |
| --- | --- |
| ABD800 | 2,4-difluorobiphenyl-4'-sulfonamide linked to cyclohexane with CH(CH₂OH)(NHMe) substituent |
| ABD842 | 2,4-difluorobiphenyl-4'-sulfonamide linked to cyclopentane with CH(CH₂OH)(NHMe) substituent (trans stereochemistry) |
| ABD843 | 3,5-dichloropyridin-2-yl-phenyl sulfonamide linked to cyclopentane with CH(CH₂OH)(NHMe) substituent (trans stereochemistry) |
| ABD844 | 3,5-dichloropyridin-2-yl-phenyl sulfonamide linked to cyclohexane with CH(CH₂OH)(NHMe) substituent |

In one embodiment, the compounds are selected from a compound of the following formula and pharmaceutically acceptable salts, hydrates, and solvates thereof:

| Compound No. | Structure |
|---|---|
| ABD786 | 2',4'-difluoro-biphenyl-4-sulfonic acid (4-oxo-cyclohexyl)-amide |

In one embodiment, the compounds are selected from compounds of the following formulae and pharmaceutically acceptable salts, hydrates, and solvates thereof:

| Compound No. | Structure |
|---|---|
| ABD824a | 2',4'-difluoro-biphenyl-4-sulfonyl-NH-cyclohexyl-C(O)NHMe |
| ABD826a | 2',4'-difluoro-biphenyl-4-sulfonyl-NH-cyclohexyl-C(O)NMe₂ |
| ABD847 | 2',4'-difluoro-biphenyl-4-sulfonyl-NH-cyclopentyl(trans)-C(O)NMe₂ |
| ABD848 | 2',4'-difluoro-biphenyl-4-sulfonyl-NH-cyclohexyl-C(O)NH₂ |
| ABD849 | 2',4'-difluoro-biphenyl-4-sulfonyl-NH-cyclohexyl-C(O)NHEt |
| ABD868 | 2',4'-difluoro-biphenyl-4-sulfonyl-NH-cyclopentyl(trans)-C(O)NHMe |

In one embodiment, the compounds are selected from compounds of the following formulae and pharmaceutically acceptable salts, hydrates, and solvates thereof:

| Compound No. | Structure |
|---|---|
| ABD899 | 2',4'-difluoro-biphenyl-4-sulfonamide linked to 4-hydroxy-4-methylcyclohexyl (cis/trans unspecified, OH up, Me down) |
| ABD900 | 2',4'-difluoro-biphenyl-4-sulfonamide linked to 4-hydroxy-4-methylcyclohexyl (OH down, Me up) |
| ABD901 | 2',4'-difluoro-biphenyl-4-sulfonamide linked to 4-(hydroxymethyl)-4-methylcyclohexyl |
| ABD903 | 2',4'-difluoro-biphenyl-4-sulfonamide linked to 4-methyl-4-(dimethylamino)cyclohexyl |

In one embodiment, the compounds is selected from a compound of the following formula and pharmaceutically acceptable salts, hydrates, and solvates thereof:

| Compound No. | Structure |
|---|---|
| ABD902 | 2',4'-difluoro-biphenyl-4-sulfonamide linked to bicyclo[2.2.2]octyl bearing OH (stereochemistry indicated) |

Chirality

In some embodiments (for example, according to the choice for —$D^1$-; the choices for —$R^{1A}$ and —$R^{2A}$; the choices for —$R^{3A}$ and —$R^{4A}$; the choices for —$R^{5A}$ and —$R^{6A}$; the choices for —$R^{1B}$ and —$R^{2B}$; the choices for —$R^{3B}$ and —$R^{4B}$; the choices for —$R^{5B}$ and —$R^{6B}$), the compound may have one or more chiral centres.

The chiral centre, or each chiral centre, if more than one is present, is independently in the R-configuration or the S-configuration.

If no configuration is indicated, then both configurations are encompassed.

Substantially Purified Forms

One aspect of the present invention pertains to APSAC compounds, as described herein, in substantially purified form and/or in a form substantially free from contaminants.

In one embodiment, the substantially purified form is at least 50% by weight, e.g., at least 60% by weight, e.g., at least 70% by weight, e.g., at least 80% by weight, e.g., at least 90% by weight, e.g., at least 95% by weight, e.g., at least 97% by weight, e.g., at least 98% by weight, e.g., at least 99% by weight.

Unless specified, the substantially purified form refers to the compound in any stereoisomeric or enantiomeric form. For example, in one embodiment, the substantially purified form refers to a mixture of stereoisomers, i.e., purified with respect to other compounds. In one embodiment, the substantially purified form refers to one stereoisomer, e.g., optically pure stereoisomer. In one embodiment, the substantially purified form refers to a mixture of enantiomers. In one embodiment, the substantially purified form refers to an equimolar mixture of enantiomers (i.e., a racemic mixture, a racemate). In one embodiment, the substantially purified form refers to one enantiomer, e.g., optically pure enantiomer.

In one embodiment, the contaminants represent no more than 50% by weight, e.g., no more than 40% by weight, e.g., no more than 30% by weight, e.g., no more than 20% by weight, e.g., no more than 10% by weight, e.g., no more than 5% by weight, e.g., no more than 3% by weight, e.g., no more than 2% by weight, e.g., no more than 1% by weight.

Unless specified, the contaminants refer to other compounds, that is, other than stereoisomers or enantiomers. In one embodiment, the contaminants refer to other compounds and other stereoisomers. In one embodiment, the contaminants refer to other compounds and the other enantiomer.

In one embodiment, the substantially purified form is at least 60% optically pure (i.e., 60% of the compound, on a molar basis, is the desired stereoisomer or enantiomer, and 40% is the undesired stereoisomer or enantiomer), e.g., at least 70% optically pure, e.g., at least 80% optically pure, e.g., at least 90% optically pure, e.g., at least 95% optically pure, e.g., at least 97% optically pure, e.g., at least 98% optically pure, e.g., at least 99% optically pure.

Isomers

Certain compounds may exist in one or more particular geometric, optical, enantiomeric, diasteriomeric, epimeric, atropic, stereoisomeric, tautomeric, conformational, or anomeric forms, including but not limited to, cis- and trans-forms; E- and Z-forms; c-, t-, and r-forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

Note that, except as discussed below for tautomeric forms, specifically excluded from the term "isomers," as used herein, are structural (or constitutional) isomers (i.e., isomers which differ in the connections between atoms rather than merely by the position of atoms in space). For example, a reference to a methoxy group, —$OCH_3$, is not to be construed as a reference to its structural isomer, a hydroxymethyl group, —$CH_2OH$. Similarly, a reference to ortho-chlorophenyl is not to be construed as a reference to its structural isomer, meta-chlorophenyl. However, a reference to a class of structures may well include structurally isomeric forms falling within that class (e.g., $C_{1-7}$alkyl includes n-propyl and iso-propyl; butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, N-nitroso/hydroxyazo, and nitro/aci-nitro.

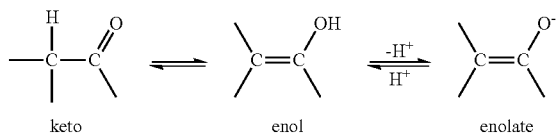

keto      enol      enolate

Note that specifically included in the term "isomer" are compounds with one or more isotopic substitutions. For example, H may be in any isotopic form, including $^1H$, $^2H$ (D), and $^3H$ (T); C may be in any isotopic form, including $^{12}C$, $^{13}C$, and $^{14}C$; O may be in any isotopic form, including $^{16}O$ and $^{18}O$; and the like.

Unless otherwise specified, a reference to a particular compound includes all such isomeric forms, including mixtures (e.g., racemic mixtures) thereof. Methods for the preparation (e.g., asymmetric synthesis) and separation (e.g., fractional crystallisation and chromatographic means) of such isomeric forms are either known in the art or are readily obtained by adapting the methods taught herein, or known methods, in a known manner.

Salts

It may be convenient or desirable to prepare, purify, and/or handle a corresponding salt of the compound, for example, a pharmaceutically-acceptable salt. Examples of pharmaceutically acceptable salts are discussed in Berge et al., 1977, "Pharmaceutically Acceptable Salts," *J. Pharm. Sci.*, Vol. 66, pp. 1-19.

For example, if the compound is anionic, or has a functional group which may be anionic (e.g., —COOH may be —COO⁻), then a salt may be formed with a suitable cation. Examples of suitable inorganic cations include, but are not limited to, alkali metal ions such as $Na^+$ and $K^+$, alkaline earth cations such as $Ca^{2+}$ and $Mg^{2+}$, and other cations such as $Al^{+3}$. Examples of suitable organic cations include, but are not limited to, ammonium ion (i.e., $NH_4^+$) and substituted ammonium ions (e.g., $NH_3R^+$, $NH_2R_2^+$, $NHR_3^+$, $NR_4^+$). Examples of some suitable substituted ammonium ions are those derived from: ethylamine, diethylamine, dicyclohexylamine, triethylamine, butylamine, ethylenediamine, ethanolamine, diethanolamine, piperizine, benzylamine, phenylbenzylamine, choline, meglumine, and tromethamine, as well as amino acids, such as lysine and arginine. An example of a common quaternary ammonium ion is $N(CH_3)_4^+$.

If the compound is cationic, or has a functional group which may be cationic (e.g., —$NH_2$ may be —$NH_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. Examples of suitable polymeric organic anions include, but are not limited to, those derived from the following polymeric acids: tannic acid, carboxymethyl cellulose.

Unless otherwise specified, a reference to a particular compound also includes salt forms thereof.

Solvates and Hydrates

It may be convenient or desirable to prepare, purify, and/or handle a corresponding solvate of the compound. The term "solvate" is used herein in the conventional sense to refer to a complex of solute (e.g., compound, salt of compound) and solvent. If the solvent is water, the solvate may be conveniently referred to as a hydrate, for example, a mono-hydrate, a di-hydrate, a tri-hydrate, etc.

Unless otherwise specified, a reference to a particular compound also includes solvate and hydrate forms thereof.

Chemical Synthesis

Methods for the chemical synthesis of APSAC compounds of the present invention are described herein. These and/or other well-known methods may be modified and/or adapted in known ways in order to facilitate the synthesis of additional APSAC compounds of the present invention.

In one approach, an appropriate biphenyl compound is prepared from a boronic acid and bromobenzene via a Suzuki coupling, for example, as described by O'Brien et al., 2000. The biphenyl is sulfonylated using chlorosulfonic acid to give the corresponding sulfonic acid. The acid is then reacted with thionyl chloride to give the corresponding aryl sulfonyl chloride. Finally the sulfonyl chloride is coupled with an amine to give the corresponding sulfonamide. An example of such a method is shown in the following scheme.

Scheme 1

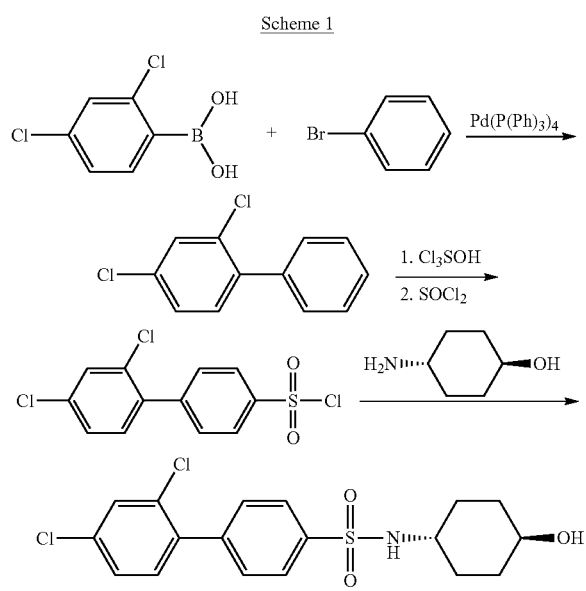

In another approach, the sulfonamide can be formed first, from a suitable bromobenzene sulfonyl chloride and amine, and the biphenyl compound then prepared by a similar Suzuki methodology. An example of such a method is shown in the following scheme.

Scheme 2

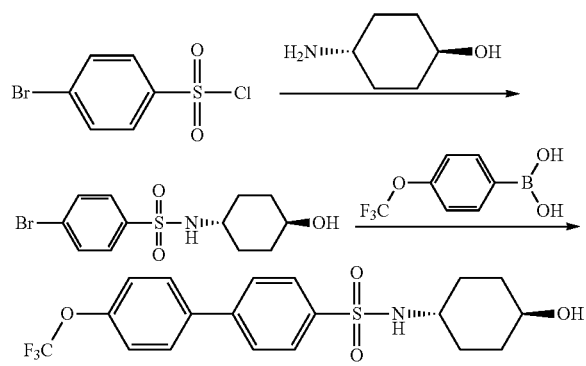

In another approach, the cyclohexanol can be replaced by a cyclohexane methyl alcohol, by coupling of the sulfonyl chloride with a carboxylic ester and subsequent reduction. For example the biphenyl sulfonyl chloride can be reacted with 4-amino-cyclohexanecarboxylic acid methyl ester in a solvent, such as DCM, in the presence of a suitable base, such as pyridine, and then reduced, for example, with lithium aluminium hydride in a solvent, such as THF, to give the desired alcohol. An example of such a method is shown in the following scheme.

Scheme 3

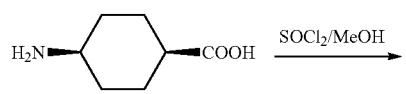

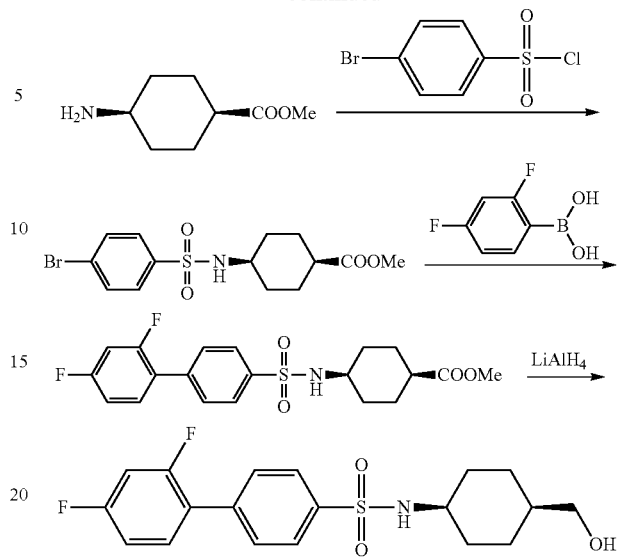

In another approach, the cyclohexane moiety can be replaced by other carbocycles to give a range of target compounds. For example, each of the four isomers of 3-amino-cyclopentane carboxylic acid and each of the four isomers of 3-amino-cyclopentane acetic acid are known and available and can be coupled with the required sulfonyl chloride and subsequently reduced, for example, with lithium aluminium hydride, to give the desired alcohol. Examples of such methods are shown in the following schemes.

Scheme 4

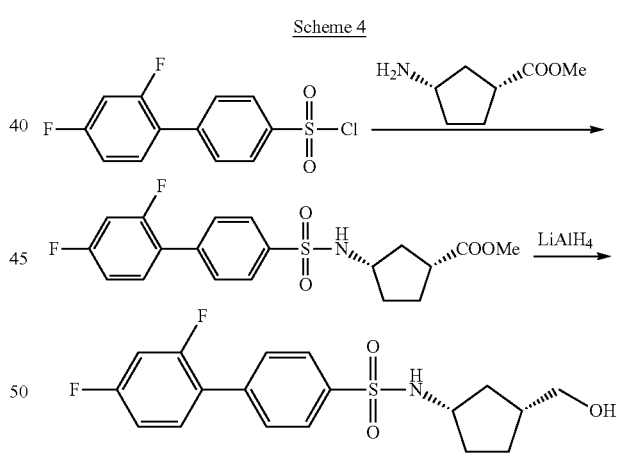

Scheme 5

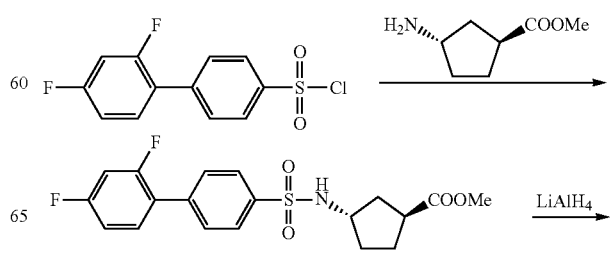

-continued

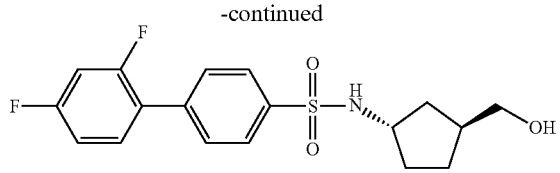

Scheme 6

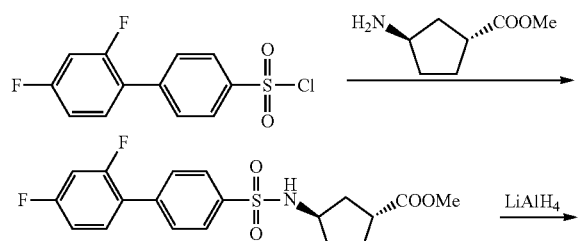

Scheme 7

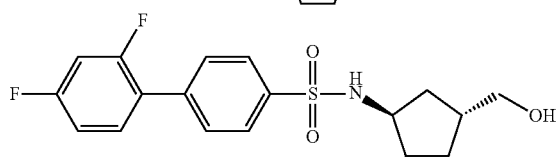

In another approach, the alcohol can be replaced by an amide by direct reaction of the sulfonyl chloride with the required aminocarboxylic acid, subsequent chlorination of the acid, and coupling with the required amine. For example, a biphenylsulfonyl chloride can be coupled with 4-aminocyclohexane carboxylic acid in a solvent, such as DCM, in the presence of a base, such as pyridine, the acid chlorinated by reflux in thionyl chloride, in a solvent such as DCM, and then coupled with methylamine in a solvent such as THF. An example of such a method is shown in the following scheme.

Scheme 8

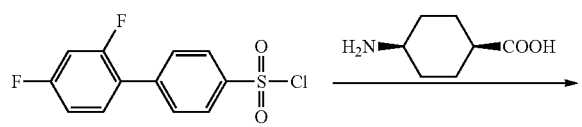

-continued

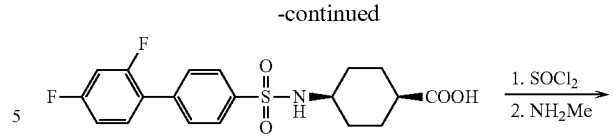

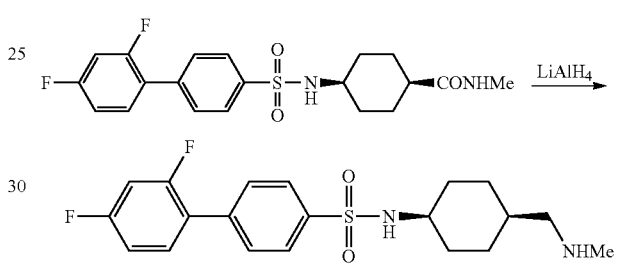

In another approach, the amide is reduced to the corresponding amine by reaction with a suitable reducing agent. For example, the amide can be reduced by lithium aluminium hydride in a solvent such as THF. An example of such a method is shown in the following scheme.

Scheme 9

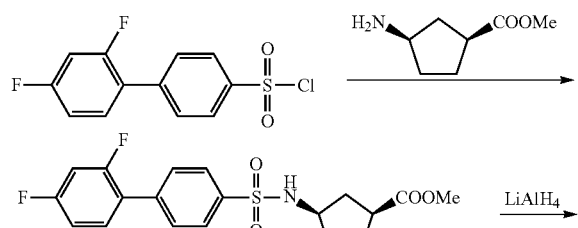

In another approach, the amino group can be introduced by direct reaction of a suitable amine with a sulfonyl chloride. For example a biphenyl sulfonyl chloride can be coupled with 1,4-diaminocyclohexane in a solvent, such as DCM, in the presence of a suitable base, such as pyridine. An example of such a method is shown in the following scheme.

Scheme 10

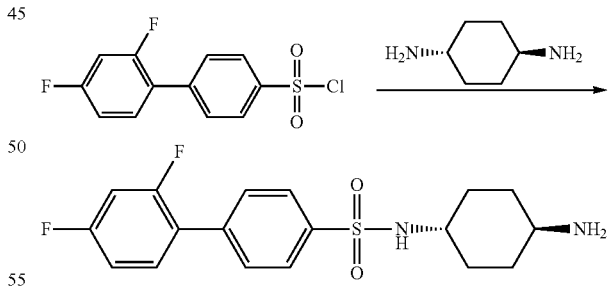

In another approach, amino substitutions may be made by nucleophilic attack of a suitable amine on a cyclohexanone. For example, the cyclohexanone can be prepared from the cyclohexanol derivative by use of Jones' oxidation (chromium trioxide/sulfuric acid), subsequent reaction with methylamine, and reduction in the presence of sodium cyanoborohydride or sodium triacetoxyborohydride in a solvent, such as methanol or THF. This methodology gives a mixture of products, which can be separated by HPLC. An example of such a method is shown in the following scheme.

Scheme 11

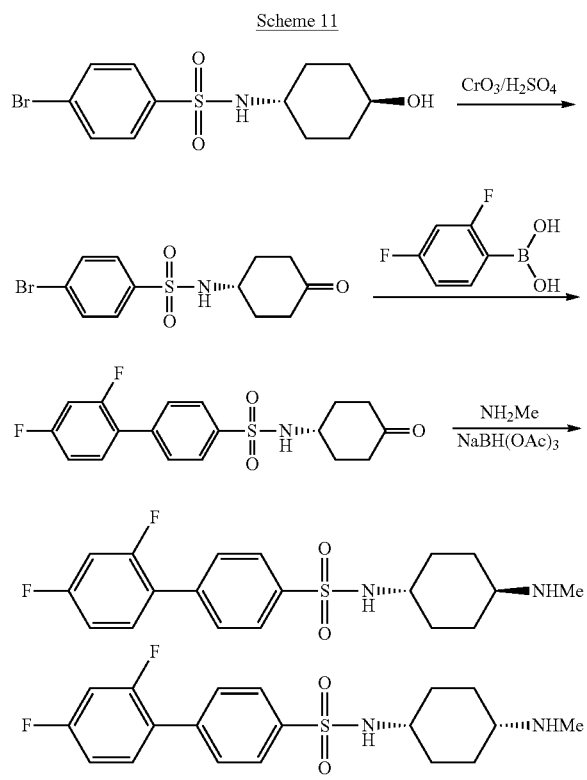

In another approach, where direct amination of the cyclohexanone gives multiple reactions, it is also possible to first react the ketone with 2,4-dimethoxybenzylamine, to give a protected intermediate. This intermediate then releases the desired amine on treatment with trifluoroacetic acid. An example of such a method is shown in the following scheme.

In another approach, further substituents can be added to the amine. For example the amine can be reacted with an acid chloride or anhydride, to give an amide, which may then be further reduced to give the secondary amine. For example, the amine can be acylated with trifluoroacetic anhydride in the presence of triethylamine and then reduced with borane in a solvent such as THF. The mixture of products may then be separated by preparative HPLC to give the cis- and trans-isomers. An example of such a method is shown in the following scheme.

Scheme 13

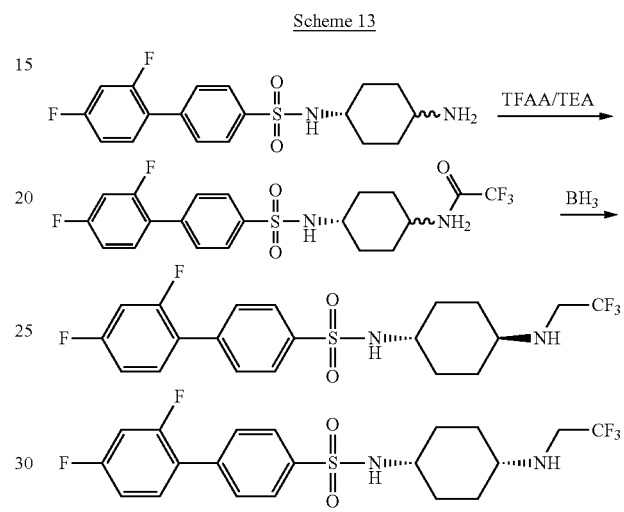

In another approach, the cyclohexanone intermediate can be used to prepare cis- or trans-isomers where the required starting material is unavailable. For example, the cyclohexanone derivative can be prepared from trans-4-aminocyclohexanol and reduced with LS-Selectride (lithium trisiamyl- Scheme 12

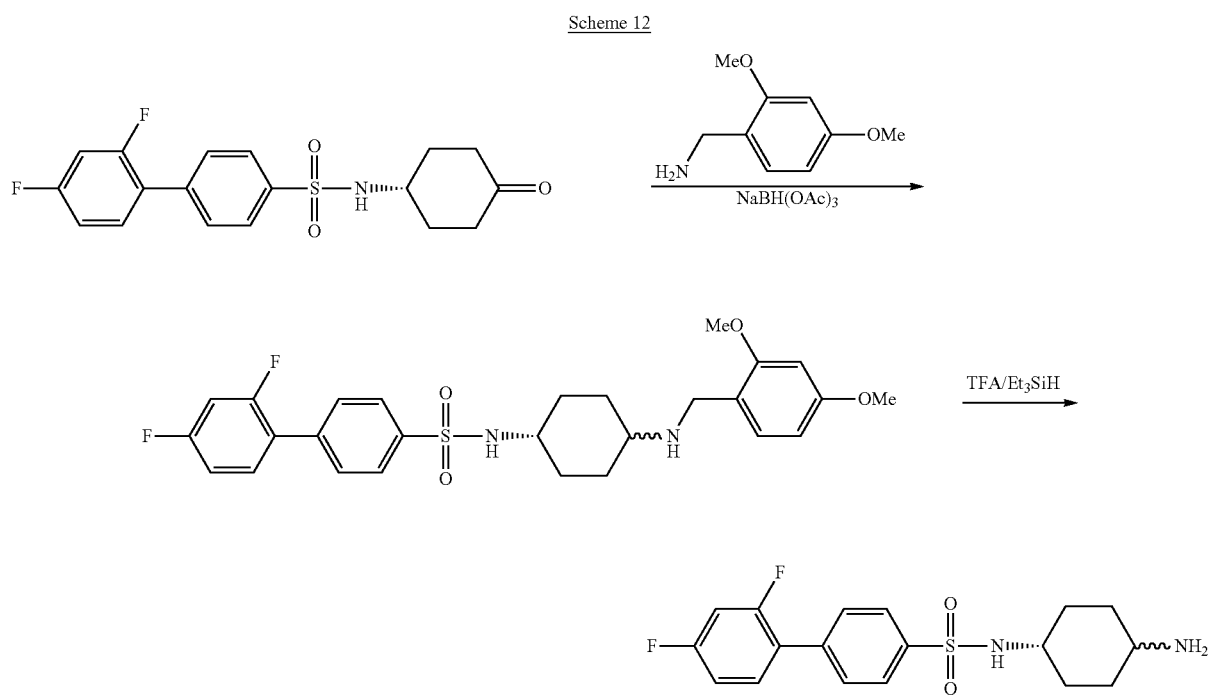

borohydride) in THF to give the cis-isomer as the final product. An example of such a method is shown in the following scheme.

Scheme 14

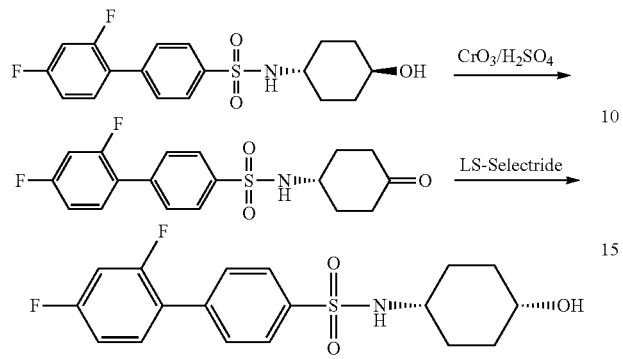

In another approach, the cyclohexanone intermediate can be reduced with a Grignard reagent to give the tertiary alcohol. For example, the cyclohexanone can be reacted with methyl magnesium bromide and the racemic mixture separated by preparative HPLC to give the cis- and trans-isomers. An example of such a method is shown in the following scheme.

Scheme 15

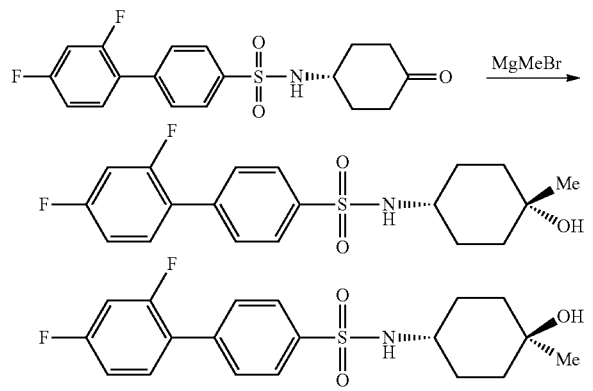

In another approach, the cis and trans-aminocyclohexanol isomers can be separated prior to coupling with the sulfonyl chloride. For example, trans-4-aminocyclohexanol can be amino-protected with a suitable protecting group, oxidised to the cyclohexanone, reacted with a suitable Grignard, and then separated, prior to deprotection and coupling. For example, the amine can be BOC protected, using di-tert-butyl dicarbonate, the alcohol oxidised using pyridinium chlorochromate, the cyclohexanone reacted with methylmagnesium chloride and the BOC protecting group removed with a reagent such as trifluoroacetic acid or ethanolic HCl, following separation of the isomers by column chromatography. An example of such a method is shown in the following scheme.

Scheme 16

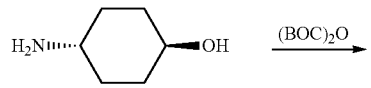

-continued

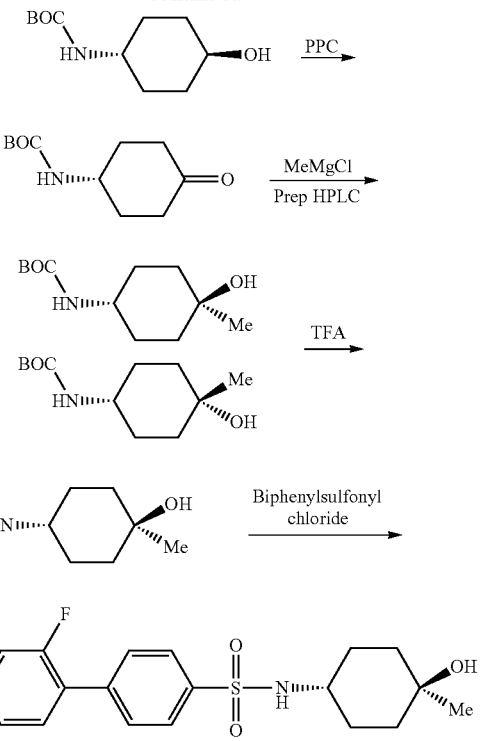

In another approach, further substituents may be added to a cyclohexane or cyclopentane methylalcohol derivative, by nucleophilic attack on the corresponding carboxylic ester. For example the ester can be reacted with a Grignard reagent such as methyl magnesium bromide in a solvent such as THF. An example of such a method is shown in the following scheme.

Scheme 17

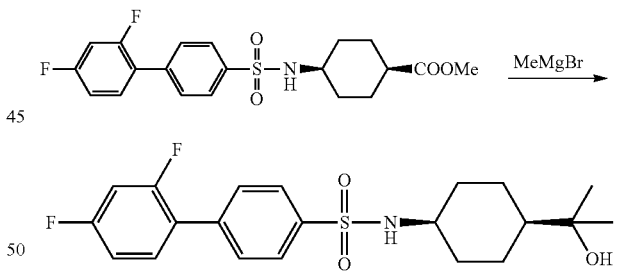

In another approach, the biphenyl sulfonamide group can be replaced by a heteroaryl-phenyl sulfonamide motif by preparation of any of the above derivatives as a bromophenyl sulfonamide derivative, preparation of the boronic acid or boronate, and subsequent Suzuki coupling with a substituted pyridyl bromide, at a suitable stage of the reaction pathway. For example, bromobenzene sulfonamide compounds can be prepared from the cyclohexanol, cyclohexane carboxylic acid, and cyclopentane carboxylic acid compounds described in the above schemes. These can then be reacted with bis (pinacolato)diboron to give the required borane, which can then be coupled with an appropriate heterocyclic bromide using Suzuki coupling. Examples of such methods are shown in the following schemes.

Scheme 18

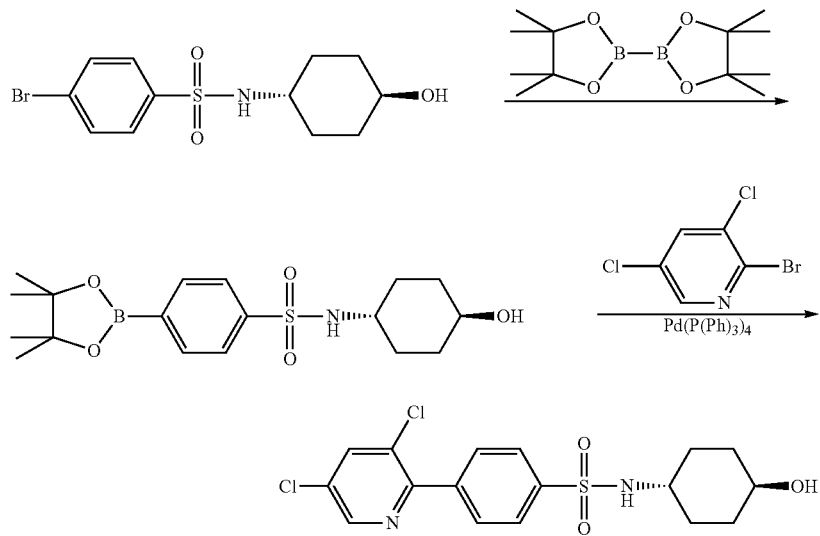

Scheme 19

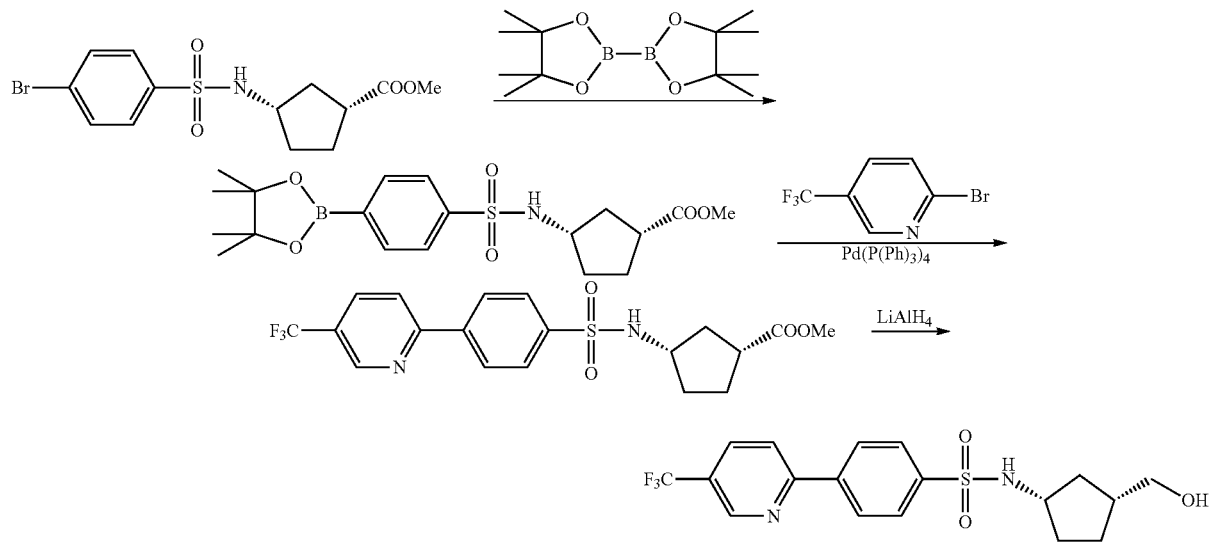

50

In another approach, all four 2-aminocyclopentane carboxylate isomers can be prepared by reductive amination of ethyl 2-oxocyclopentanecarboxylate and used to prepare the respective sulfonamide-cyclopentane methyl alcohol compound. For example, ethyl 2-oxocyclopentanecarboxylate can be reacted with ammonium acetate and then reduced with sodium triacetoxyborohydride to give the racemic mixture of 2-aminocarboxylates, which may be separated by HPLC, or further coupled with a biphenyl sulfonyl chloride, reduced with lithium aluminium hydride and then separated. An example is shown in the following scheme.

Scheme 20

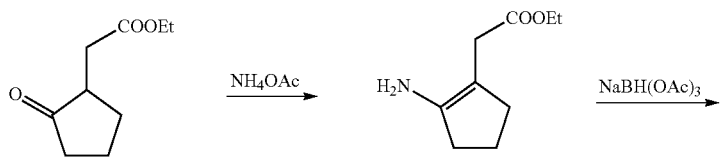

-continued

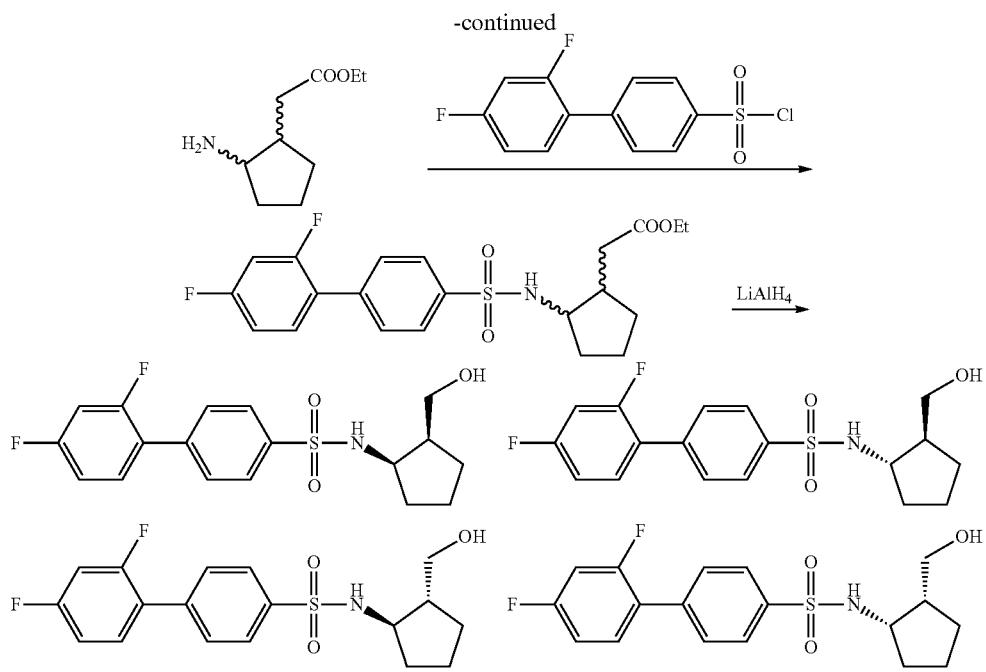

Compositions

One aspect of the present invention pertains to a composition (e.g., a pharmaceutical composition) comprising an APSAC compound, as described herein, and a pharmaceutically acceptable carrier, diluent, or excipient.

Another aspect of the present invention pertains to a method of preparing a composition (e.g., a pharmaceutical composition) comprising admixing an APSAC compound, as described herein, and a pharmaceutically acceptable carrier, diluent, or excipient.

Uses

The APSAC compounds described herein are believed to be anti-inflammatory agents, which may act by blockade or modification of pro-inflammatory signalling pathways (for example those mediated by TNFα signalling and NFκB or AP-1 activation) and thus may prevent inflammation or suppress autoimmune responses or offer protection against joint destruction and other effects of chronic inflammatory disease.

The APSAC compounds described herein are also believed to be anti-resorptive agents, which may act by blockade or modification of pathways that lead to excessive osteoclast activity (for example those mediated by RANKL, TNFα, and IL-1 signalling and NFκB activation) and thereby protect against the bone loss seen in osteoporosis and many chronic inflammatory conditions.

Thus, the APSAC compounds described herein are believed to be useful in the treatment of inflammation and/or joint destruction and/or bone loss.

Thus, the APSAC compounds described herein are believed to be useful in the treatment of disorders mediated by excessive and/or inappropriate and/or prolonged activation of the immune system.

Thus, the APSAC compounds described herein are believed to be useful in the treatment of, inflammatory and autoimmune disorders, for example, rheumatoid arthritis, psoriasis, psoriatic arthritis, chronic obstructive pulmonary disease (COPD), atherosclerosis, inflammatory bowel disease, ankylosing spondylitis, and the like.

Thus, the APSAC compounds described herein are believed to be useful in the treatment of disorders associated with bone loss, such as bone loss associated with excessive osteoclast activation in rheumatoid arthritis; osteoporosis; cancer-associated bone disease; Paget's disease; and the like.

Thus, the APSAC compounds described herein are believed to be useful in the treatment of haematological malignancies, e.g., multiple myeloma, leukaemia, or lymphoma (e.g., non-Hodgkin Lymphoma), e.g., haematological malignancies, multiple myeloma, leukaemia, or lymphoma (e.g., non-Hodgkin Lymphoma) associated with activation of NFκB, with aberrant NFκB signalling, or with inflammation.

Thus, the APSAC compounds described herein are believed to be useful in the treatment of solid tumour cancers, e.g., cancer of the bladder, breast cancer (female and/or male), colon cancer, kidney cancer, lung cancer, pancreatic cancer, prostate cancer, brain cancer, skin cancer, thyroid cancer, or melanoma, e.g., solid tumour cancers, cancer of the bladder, breast cancer (female and/or male), colon cancer, kidney cancer, lung cancer, pancreatic cancer, prostate cancer, brain cancer, skin cancer, thyroid cancer, and melanoma associated with activation of NFκB, with aberrant NFκB signalling, or with inflammation.

Thus, the APSAC compounds described herein are believed to be useful in the treatment of a haematological malignancy, e.g., T-cell lymphoblastic lymphoma, mantle cell lymphoma, or acute lymphoblastic leukemia, e.g., a haematological malignancy, T-cell lymphoblastic lymphoma, mantle cell lymphoma, or acute lymphoblastic leukemia associated with inactivation or impairment of caspase induction or with aberrant caspase signalling, e.g., alone, or in combination with, and to augment the efficacy of, radiotherapy or chemotherapy.

Thus, the APSAC compounds described herein are believed to be useful in the treatment of a solid tumour cancer, e.g., renal cell carcinoma, breast cancer (female and/or male), gastric cancer, prostate cancer, colon cancer or basal cell ameloblastoma, e.g., a solid tumour cancer, e.g., renal cell carcinoma, breast cancer (female and/or male), gastric cancer, prostate cancer, colon cancer, or basal cell ameloblastoma associated with inactivation or impairment of caspase induction or with aberrant caspase signalling, e.g., alone or in combination with, and to augment the efficacy of, radiotherapy or chemotherapy.

Use in Methods of Inhibition

One aspect of the invention pertains to a method of inhibiting an inflammatory response, in vitro or in vivo, comprising contacting an immune system component with an effective amount of an APSAC compound, as described herein.

One aspect of the invention pertains to a method of inhibiting cellular and/or molecular pathways leading to joint destruction, in vitro or in vivo, comprising contacting cells associated with an immune response with a therapeutically-effective amount of an APSAC compound, as described herein.

One aspect of the invention pertains to a method of inhibiting osteoclast survival, formation, and/or activity, in vitro or in vivo, comprising contacting an osteoclast with an effective amount of an APSAC compound, as described herein.

One aspect of the invention pertains to a method of inhibiting bone resorption, in vitro or in vivo, comprising contacting cells in the bone microenvironment with a therapeutically-effective amount of an APSAC compound, as described herein.

The term "immune system component," as used herein, relates to, but is not restricted to, cells such as macrophages, T-cells, B-cells, NK-cells, monocytes, neutrophils, dendritic cells, lymphocytes, leukocytes, granulocytes, antigen-presenting cells, and other cells of the haematopoietic lineage including osteoclasts.

The term "cells in the bone microenvironment," as used herein, pertains to cells such as osteoblasts, osteoclasts, osteocytes, and bone marrow stromal cells, which are located in close proximity to bone (e.g., within one hundred micrometers of the bone surface).

Use in Methods of Therapy

Another aspect of the present invention pertains to an APSAC compound, as described herein, for use in a method of treatment of the human or animal body by therapy.

Use in the Manufacture of Medicaments

Another aspect of the present invention pertains to use of an APSAC compound, as described herein, in the manufacture of a medicament for use in treatment.

In one embodiment, the medicament comprises the APSAC compound.

Methods of Treatment

Another aspect of the present invention pertains to a method of treatment comprising administering to a patient in need of treatment a therapeutically effective amount of an APSAC compound, as described herein, preferably in the form of a pharmaceutical composition.

Diseases and Disorders

In one embodiment, the treatment is treatment of an inflammatory disorder or an autoimmune disorder.

In one embodiment, the treatment is treatment of a disorder associated with inflammation and/or activation of the immune system.

In one embodiment, the treatment is treatment of a disorder mediated by excessive and/or inappropriate and/or prolonged activation of the immune system.

In one embodiment, the treatment is treatment of inflammation.

In one embodiment, the treatment is treatment of a disorder associated with inflammation or activation of the immune system.

In one embodiment, the treatment is treatment of rheumatoid arthritis.

In one embodiment, the treatment is treatment of psoriasis.

In one embodiment, the treatment is treatment of psoriatic arthritis.

In one embodiment, the treatment is treatment of chronic obstructive pulmonary disease (COPD).

In one embodiment, the treatment is treatment of atherosclerosis.

In one embodiment, the treatment is treatment of ankylosing spondylitis.

In one embodiment, the treatment is treatment of inflammatory bowel disease.

In one embodiment, the treatment is prevention of an immune response leading to organ or graft rejection following transplant.

In one embodiment, the treatment is treatment of a tumour which over expresses TNFα, IL-1, RANKL, or NFκB, or in which inhibition of TNFα, IL-1, RANKL, or NFκB facilitates or improves the action of cytotoxic tumouricidal agents.

In one embodiment, the treatment is treatment of a haematological malignancy, e.g., multiple myeloma, leukaemia, or lymphoma (e.g., non-Hodgkin Lymphoma), e.g., a haematological malignancy, multiple myeloma, leukaemia, or lymphoma (e.g., non-Hodgkin Lymphoma) associated with activation of NFκB, with aberrant NFκB signalling, or with inflammation, e.g., alone, or in combination with, and to augment the efficacy of, radiotherapy or chemotherapy.

In one embodiment, the treatment is treatment of a solid tumour cancer, e.g., cancer of the bladder, breast cancer (female and/or male), colon cancer, kidney cancer, lung cancer, pancreatic cancer, prostate cancer, brain cancer, skin cancer, thyroid cancer, or melanoma, e.g., a solid tumour cancer, cancer of the bladder, breast cancer (female and/or male), colon cancer, kidney cancer, lung cancer, pancreatic cancer, prostate cancer, brain cancer, skin cancer, thyroid cancer, and melanoma associated with activation of NFκB, with aberrant NFκB signalling, or with inflammation, e.g., alone, or in combination with, and to augment the efficacy of, radiotherapy or chemotherapy.

In one embodiment, the treatment is treatment of a haematological malignancy, e.g., T-cell lymphoblastic lymphoma, mantle cell lymphoma, or acute lymphoblastic leukemia, e.g., a haematological malignancy, T-cell lymphoblastic lymphoma, mantle cell lymphoma, or acute lymphoblastic leukemia associated with inactivation or impairment of caspase induction or with aberrant caspase signalling, e.g., alone or in combination with, and to augment the efficacy of, radiotherapy or chemotherapy.

In one embodiment, the treatment is treatment of a solid tumour cancer, e.g., renal cell carcinoma, breast cancer (female and/or male), gastric cancer, prostate cancer, colon cancer, or basal cell ameloblastoma, e.g., a solid tumour cancer, e.g., renal cell carcinoma, breast cancer (female and/or male), gastric cancer, prostate cancer, colon cancer, or basal cell ameloblastoma associated with inactivation or impairment of caspase induction or with aberrant caspase signalling, e.g., alone, or in combination with, and to augment the efficacy of, radiotherapy or chemotherapy.

In one embodiment, the treatment is part of treatment by combination therapy, e.g., in combination with, and to augment the efficacy of, radiotherapy or chemotherapy.

In one embodiment, the treatment is treatment of a disease or disorder selected from: diseases having an inflammatory or autoimmune component, including asthma, atherosclerosis, allergic diseases, such as atopy, allergic rhinitis, atopic dermatitis, anaphylaxis, allergic bronchopulmonary aspergillosis, and hypersensitivity pneumonitis (pigeon breeders disease, farmer's lung disease, humidifier lung disease, malt workers' lung disease); allergies, including flea allergy dermatitis in mammals such as domestic animals, e.g., dogs and cats, contact allergens including mosquito bites or other insect sting allergies, poison ivy, poison oak, poison sumac, or other skin allergens; autoimmune disorders, including, but not limited to, type I diabetes and associated complications, multiple sclerosis, arthritis, systemic lupus erythematosus, autoimmune (Hasimoto's) thyroiditis, autoimmune liver diseases such as hepatitis and primary biliary cirrhosis, hyperthyroidism (Graves' disease; thyrotoxicosis), insulin-resistant diabetes, autoimmune adrenal insufficiency (Addison's disease), autoimmune oophoritis, autoimmune orchitis, autoimmune hemolytic anemia, paroxysmal cold hemoglobinuria, Behcet's disease, autoimmune thrombocytopenia, autoimmune neutropenia, pernicious anemia, pure red cell anemia, autoimmune coagulopathies, myasthenia gravis, experimental allergic encephalomyelitis, autoimmune polyneuritis, pemphigus and other bullous diseases, rheumatic carditis, Goodpasture's syndrome, postcardiotomy syndrome, Sjogren's syndrome, polymyositis, dermatomyositis, and scleroderma; disease states resulting from inappropriate inflammation, either local or systemic, for example, irritable or inflammatory bowel syndrome (Mazzucchelli et al., 1996, *J. Pathol.*, Vol. 178, p. 201), skin diseases such as lichen planus, delayed type hypersensitivity, chronic pulmonary inflammation, e.g., pulmonary alveolitis and pulmonary granuloma, gingival inflammation or other periodontal disease, and osseous inflammation associated with lesions of endodontic origin (Volejnikova et al., 1997, *Am. J. Pathol.*, Vol. 150, p. 1711), hypersensitivity lung diseases such as hypersensitivity pneumonitis (Sugiyama et al., 1995, *Eur. Respir. J.*, Vol. 8, p. 1084), and inflammation related to histamine release from basophils (Dvorak et al., 1996, *J. Allergy Clin. Immunol.*, Vol. 98, p. 355), such as hay fever, histamine release from mast cells (Galli et al., 1989, *Ciba Foundation Symposium*, Vol. 147, p. 53), or mast cell tumours, types of type 1 hypersensitivity reactions (anaphylaxis, skin allergy, hives, gout, allergic rhinitis, and allergic gastroenteritis); ulcerative colitis or Crohn's disease; TNFα induced polycystic kidney disease (Li et al., 2008, *Nature Medicine*, Vol. 14(8), p. 863); or Cryopyrin-Associated Periodic Syndromes, including Muckle-Wells Syndrome.

In one embodiment, the treatment is treatment of a disorder mediated by osteoclasts.

In one embodiment, the treatment is treatment of a disorder characterised by excessive bone resorption.

In one embodiment, the treatment is treatment of bone loss.

In one embodiment, the treatment is treatment of bone loss associated with inflammation.

In one embodiment, the treatment is treatment of bone loss not associated with inflammation.

In one embodiment, the treatment is treatment of bone loss associated with excessive osteoclast activation.

In one embodiment, the treatment is treatment of joint destruction.

In one embodiment, the treatment is treatment of joint destruction associated with inflammation.

In one embodiment, the treatment is treatment of joint destruction associated with excessive osteoclast activation.

In one embodiment, the treatment is treatment of bone loss associated with rheumatoid arthritis, osteoporosis, cancer-associated bone disease, or Paget's disease of bone.

In one embodiment, the treatment is treatment of rheumatoid arthritis, osteoporosis, cancer-associated bone disease, or Paget's disease of bone.

In one embodiment, the treatment is treatment of neoplasia of bones, whether as a primary tumour or as metastases, including but not limited to, osteosarcoma and osteoma (Zheng et al., 1998, *J. Cell Biochem.*, Vol. 70, p. 121) and cancer-associated bone disease (e.g., hypercalcaemia of malignancy, bone metastases, osteolytic bone metastases, multiple myeloma, breast carcinoma).

In one embodiment, the treatment is treatment of hypercalcaemia caused by conditions associated with increased bone resorption, including, but not limited to: vitamin D intoxication, primary or tertiary hyperparathyroidism, immobilisation, and sarcoidosis.

In one embodiment, the treatment is treatment of aseptic loosening of prosthetic implants (e.g., artificial joints, e.g., knees, hips, etc., can loosen due to osteoclast activity driven by local inflammation) (see, e.g., Childs, L. M., et al., 2001, *Journal of Bone and Mineral Research*, Vol. 16, No. 2, pp. 338-347).

In one embodiment, the treatment is treatment of osteopetrosis, osteoarthritis, or ectopic bone formation.

Treatment

The term "treatment," as used herein in the context of treating a condition, pertains generally to treatment and therapy, whether of a human or an animal (e.g., in veterinary applications), in which some desired therapeutic effect is achieved, for example, the inhibition of the progress of the condition, and includes a reduction in the rate of progress, a halt in the rate of progress, alleviatiation of symptoms of the condition, amelioration of the condition, and cure of the condition. Treatment as a prophylactic measure (i.e., prophylaxis) is also included. For example, use with patients who have not yet developed the condition, but who are at risk of developing the condition, is encompassed by the term "treatment."

For example, use with perimenopausal women who may not yet have osteoporosis, but who are at risk of osteoporosis, is encompassed by the term "treatment."

The term "therapeutically-effective amount," as used herein, pertains to that amount of a compound, or a material, composition or dosage form comprising a compound, which is effective for producing some desired therapeutic effect, commensurate with a reasonable benefit/risk ratio, when administered in accordance with a desired treatment regimen.

The term "treatment" includes combination treatments and therapies, in which two or more treatments or therapies are combined, for example, sequentially or simultaneously. Examples of treatments and therapies include, but are not limited to, chemotherapy (the administration of active agents, including, e.g., drugs, antibodies (e.g., as in immunotherapy), prodrugs (e.g., as in photodynamic therapy, GDEPT, ADEPT, etc.); surgery; radiation therapy; and gene therapy.

Other Uses

The APSAC compounds described herein may also be used as cell culture additives to inhibit immune cell function, for example, to inhibit the survival, formation, and/or activity of macrophages, T-cells, or other cells involved in the immune response.

The APSAC compounds, as described herein, may also be used as cell culture additives, for example, to inhibit osteoclasts, for example, to inhibit the survival, formation, and/or activity of osteoclasts.

The APSAC compounds described herein may also be used as part of an in vitro assay, for example, in order to determine whether a candidate host is likely to benefit from treatment with the compound in question.

The APSAC compounds described herein may also be used as a standard, for example, in an assay, in order to identify other active compounds, other osteoclast inhibitors, etc.

Kits

One aspect of the invention pertains to a kit comprising (a) an APSAC compound as described herein, or a composition comprising an APSAC compound as described herein, e.g., preferably provided in a suitable container and/or with suitable packaging; and (b) instructions for use, e.g., written instructions on how to administer the compound or composition.

The written instructions may also include a list of indications for which the APSAC compound is a suitable treatment.

Routes of Administration

The APSAC compound or pharmaceutical composition comprising the APSAC compound may be administered to a subject by any convenient route of administration, whether systemically/peripherally or topically (i.e., at the site of desired action).

Routes of administration include, but are not limited to, oral (e.g., by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eyedrops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly.

The Subject/Patient

The subject/patient may be a chordate, a vertebrate, a mammal, a placental mammal, a marsupial (e.g., kangaroo, wombat), a rodent (e.g., a guinea pig, a hamster, a rat, a mouse), murine (e.g., a mouse), a lagomorph (e.g., a rabbit), avian (e.g., a bird), canine (e.g., a dog), feline (e.g., a cat), equine (e.g., a horse), porcine (e.g., a pig), ovine (e.g., a sheep), bovine (e.g., a cow), a primate, simian (e.g., a monkey or ape), a monkey (e.g., marmoset, baboon), an ape (e.g., gorilla, chimpanzee, orangutang, gibbon), or a human.

Furthermore, the subject/patient may be any of its forms of development, for example, a fetus.

In one preferred embodiment, the subject/patient is a human.

Formulations

While it is possible for the APSAC compound to be administered alone, it is preferable to present it as a pharmaceutical formulation (e.g., composition, preparation, medicament) comprising at least one APSAC compound, as described herein, together with one or more other pharmaceutically acceptable ingredients well known to those skilled in the art, including, but not limited to, pharmaceutically acceptable carriers, diluents, excipients, adjuvants, fillers, buffers, preservatives, anti-oxidants, lubricants, stabilisers, solubilisers, surfactants (e.g., wetting agents), masking agents, colouring agents, flavouring agents, and sweetening agents. The formulation may further comprise other active agents, for example, other therapeutic or prophylactic agents.

Thus, the present invention further provides pharmaceutical compositions, as defined above, and methods of making a pharmaceutical composition comprising admixing at least one APSAC compound, as described herein, together with one or more other pharmaceutically acceptable ingredients well known to those skilled in the art, e.g., carriers, diluents, excipients, etc. If formulated as discrete units (e.g., tablets, etc.), each unit contains a predetermined amount (dosage) of the compound.

The term "pharmaceutically acceptable," as used herein, pertains to compounds, ingredients, materials, compositions, dosage forms, etc., which are, within the scope of sound medical judgment, suitable for use in contact with the tissues of the subject in question (e.g., human) without excessive toxicity, irritation, allergic response, or other problem or complication, commensurate with a reasonable benefit/risk ratio. Each carrier, diluent, excipient, etc. must also be "acceptable" in the sense of being compatible with the other ingredients of the formulation.

Suitable carriers, diluents, excipients, etc. can be found in standard pharmaceutical texts, for example, *Remington's Pharmaceutical Sciences*, 18th edition, Mack Publishing Company, Easton, Pa., 1990; and *Handbook of Pharmaceutical Excipients,* 5th edition, 2005.

The formulations may be prepared by any methods well known in the art of pharmacy. Such methods include the step of bringing into association the compound with a carrier which constitutes one or more accessory ingredients. In general, the formulations are prepared by uniformly and intimately bringing into association the compound with carriers (e.g., liquid carriers, finely divided solid carrier, etc.), and then shaping the product, if necessary.

The formulation may be prepared to provide for rapid or slow release; immediate, delayed, timed, or sustained release; or a combination thereof.

Formulations may suitably be in the form of liquids, solutions (e.g., aqueous, non-aqueous), suspensions (e.g., aqueous, non-aqueous), emulsions (e.g., oil-in-water, water-in-oil), elixirs, syrups, electuaries, mouthwashes, drops, tablets (including, e.g., coated tablets), granules, powders, losenges, pastilles, capsules (including, e.g., hard and soft gelatin capsules), cachets, pills, ampoules, boluses, suppositories, pessaries, tinctures, gels, pastes, ointments, creams, lotions, oils, foams, sprays, mists, or aerosols.

Formulations may suitably be provided as a patch, adhesive plaster, bandage, dressing, or the like which is impregnated with one or more compounds and optionally one or more other pharmaceutically acceptable ingredients, including, for example, penetration, permeation, and absorption enhancers. Formulations may also suitably be provided in the form of a depot or reservoir.

The compound may be dissolved in, suspended in, or admixed with one or more other pharmaceutically acceptable ingredients. The compound may be presented in a liposome or other microparticulate which is designed to target the compound, for example, to blood components or one or more organs.

Formulations suitable for oral administration (e.g., by ingestion) include liquids, solutions (e.g., aqueous, non-aqueous), suspensions (e.g., aqueous, non-aqueous), emulsions (e.g., oil-in-water, water-in-oil), elixirs, syrups, electuaries, tablets, granules, powders, capsules, cachets, pills, ampoules, boluses.

Formulations suitable for buccal administration include mouthwashes, losenges, pastilles, as well as patches, adhesive plasters, depots, and reservoirs. Losenges typically comprise the compound in a flavored basis, usually sucrose and acacia or tragacanth. Pastilles typically comprise the compound in an inert matrix, such as gelatin and glycerin, or sucrose and acacia. Mouthwashes typically comprise the compound in a suitable liquid carrier.

Formulations suitable for sublingual administration include tablets, losenges, pastilles, capsules, and pills.

Formulations suitable for oral transmucosal administration include liquids, solutions (e.g., aqueous, non-aqueous), suspensions (e.g., aqueous, non-aqueous), emulsions (e.g., oil-in-water, water-in-oil), mouthwashes, losenges, pastilles, as well as patches, adhesive plasters, depots, and reservoirs.

Formulations suitable for non-oral transmucosal administration include liquids, solutions (e.g., aqueous, non-aqueous), suspensions (e.g., aqueous, non-aqueous), emulsions (e.g., oil-in-water, water-in-oil), suppositories, pessaries, gels, pastes, ointments, creams, lotions, oils, as well as patches, adhesive plasters, depots, and reservoirs.

Formulations suitable for transdermal administration include gels, pastes, ointments, creams, lotions, and oils, as well as patches, adhesive plasters, bandages, dressings, depots, and reservoirs.

Tablets may be made by conventional means, e.g., compression or moulding, optionally with one or more accessory ingredients. Compressed tablets may be prepared by compressing in a suitable machine the compound in a free-flowing form such as a powder or granules, optionally mixed with one or more binders (e.g., povidone, gelatin, acacia, sorbitol, tragacanth, hydroxypropylmethyl cellulose); fillers or diluents (e.g., lactose, microcrystalline cellulose, calcium hydrogen phosphate); lubricants (e.g., magnesium stearate, talc, silica); disintegrants (e.g., sodium starch glycolate, cross-linked povidone, cross-linked sodium carboxymethyl cellulose); surface-active or dispersing or wetting agents (e.g., sodium lauryl sulfate); preservatives (e.g., methyl p-hydroxybenzoate, propyl p-hydroxybenzoate, sorbic acid); flavours, flavour enhancing agents, and sweeteners. Moulded tablets may be made by moulding in a suitable machine a mixture of the powdered compound moistened with an inert liquid diluent. The tablets may optionally be coated or scored and may be formulated so as to provide slow or controlled release of the compound therein using, for example, hydroxypropylmethyl cellulose in varying proportions to provide the desired release profile. Tablets may optionally be provided with a coating, for example, to affect release, for example an enteric coating, to provide release in parts of the gut other than the stomach.

Ointments are typically prepared from the compound and a paraffinic or a water-miscible ointment base.

Creams are typically prepared from the compound and an oil-in-water cream base. If desired, the aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof. The topical formulations may desirably include a compound which enhances absorption or penetration of the compound through the skin or other affected areas. Examples of such dermal penetration enhancers include dimethylsulfoxide and related analogues.

Emulsions are typically prepared from the compound and an oily phase, which may optionally comprise merely an emulsifier (otherwise known as an emulgent), or it may comprises a mixture of at least one emulsifier with a fat or an oil or with both a fat and an oil. Preferably, a hydrophilic emulsifier is included together with a lipophilic emulsifier which acts as a stabiliser. It is also preferred to include both an oil and a fat. Together, the emulsifier(s) with or without stabiliser(s) make up the so-called emulsifying wax, and the wax together with the oil and/or fat make up the so-called emulsifying ointment base which forms the oily dispersed phase of the cream formulations.

Suitable emulgents and emulsion stabilisers include Tween 60, Span 80, cetostearyl alcohol, myristyl alcohol, glyceryl monostearate and sodium lauryl sulfate. The choice of suitable oils or fats for the formulation is based on achieving the desired cosmetic properties, since the solubility of the compound in most oils likely to be used in pharmaceutical emulsion formulations may be very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for intranasal administration, where the carrier is a liquid, include, for example, nasal spray, nasal drops, or by aerosol administration by nebuliser, include aqueous or oily solutions of the compound.

Formulations suitable for intranasal administration, where the carrier is a solid, include, for example, those presented as a coarse powder having a particle size, for example, in the range of about 20 to about 500 microns which is administered in the manner in which snuff is taken, i.e., by rapid inhalation through the nasal passage from a container of the powder held close up to the nose.

Formulations suitable for pulmonary administration (e.g., by inhalation or insufflation therapy) include those presented as an aerosol spray from a pressurised pack, with the use of a suitable propellant, such as dichlorodifluoromethane, trichlorofluoromethane, dichoro-tetrafluoroethane, carbon dioxide, or other suitable gases.

Formulations suitable for ocular administration include eye drops wherein the compound is dissolved or suspended in a suitable carrier, especially an aqueous solvent for the compound.

Formulations suitable for rectal administration may be presented as a suppository with a suitable base comprising, for example, natural or hardened oils, waxes, fats, semi-liquid or liquid polyols, for example, cocoa butter or a salicylate; or as a solution or suspension for treatment by enema.

Formulations suitable for vaginal administration may be presented as pessaries, tampons, creams, gels, pastes, foams or spray formulations containing in addition to the compound, such carriers as are known in the art to be appropriate.

Formulations suitable for parenteral administration (e.g., by injection), include aqueous or non-aqueous, isotonic, pyrogen-free, sterile liquids (e.g., solutions, suspensions), in which the compound is dissolved, suspended, or otherwise provided (e.g., in a liposome or other microparticulate). Such liquids may additional contain other pharmaceutically acceptable ingredients, such as anti-oxidants, buffers, preservatives, stabilisers, bacteriostats, suspending agents, thickening agents, and solutes which render the formulation isotonic with the blood (or other relevant bodily fluid) of the intended recipient. Examples of excipients include, for example, water, alcohols, polyols, glycerol, vegetable oils, and the like. Examples of suitable isotonic carriers for use in such formulations include Sodium Chloride Injection, Ringer's Solution, or Lactated Ringer's Injection. Typically, the concentration of the compound in the liquid is from about 1 ng/mL to about 100 μg/mL, for example from about 10 ng/mL to about 10 μg/mL, for example from about 10 ng/mL to about 1 μg/mL. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets.

Dosage

It will be appreciated by one of skill in the art that appropriate dosages of the APSAC compounds, and compositions comprising the APSAC compounds, can vary from patient to patient. Determining the optimal dosage will generally involve the balancing of the level of therapeutic benefit against any risk or deleterious side effects. The selected dosage level will depend on a variety of factors including, but not limited to, the activity of the particular APSAC compound, the route of administration, the time of administration, the rate of excretion of the APSAC compound, the duration of the treatment, other drugs, compounds, and/or materials used in combination, the severity of the condition, and the species, sex, age, weight, condition, general health, and prior medical history of the patient. The amount of APSAC compound and route of administration will ultimately be at the discretion of the physician, veterinarian, or clinician, although generally the dosage will be selected to achieve local concentrations at the site of action which achieve the desired effect without causing substantial harmful or deleterious side-effects.

Administration can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell(s) being treated, and the subject being treated. Single or multiple administrations can be carried out with the dose level and pattern being selected by the treating physician, veterinarian, or clinician.

In general, a suitable dose of the APSAC compound is in the range of about 10 μg to about 250 mg (more typically about 100 μg to about 25 mg) per kilogram body weight of the subject per day. Where the compound is a salt, an ester, an amide, a prodrug, or the like, the amount administered is calculated on the basis of the parent compound and so the actual weight to be used is increased proportionately.

EXAMPLES

The following examples are provided solely to illustrate the present invention and are not intended to limit the scope of the invention, as described herein.

Chemical Synthesis

Synthesis 1

4-Bromo-N-(trans-4-hydroxycyclohexyl)benzene-sulfonamide (ABD598)

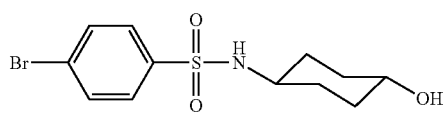

Method A:

4-Bromobenzene sulfonyl chloride (1 g) was dissolved in DCM (30 mL). Trans-4-aminocyclohexanol hydrochloride (1 g) was added, followed by pyridine (3 mL). The mixture was stirred for 3 hours, giving a brick red suspension, and then poured into 2 M HCl and separated. The organic phase was collected and the aqueous phase washed with ethyl acetate. The two organic phases were combined and the resultant solution was dried and evaporated to give an orange residue. The residue was recrystallised from ethyl acetate/petrol, filtered and the resultant powder boiled with ether and the title compound obtained as a white powder. $^{13}$C NMR (62.5 MHz, DMSO-$d_6$): δ 31.0, 33.6, 51.8, 67.6, 125.9, 128.3, 132.1 and 141.5.

Synthesis 2

2',4'-Difluoro-N-(trans-4-hydroxycyclohexyl)biphenyl-4-sulfonamide (ABD599)

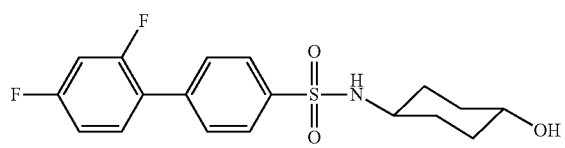 [SMILES: CC1(O)CCC(NS(=O)(=O)c2ccc(-c3ccc(F)cc3F)cc2)CC1]

Method B:

ABD598 (1.0 g) was dissolved in a mixture of toluene (15 mL) and ethanol (15 mL). 2,4-Difluorophenylboronic acid (1 g) was added followed by (PPh$_3$)$_4$Pd (0.15 g). The mixture was stirred vigorously under N$_2$ and 2 M Na$_2$CO$_3$ (15 mL) added. The mixture was refluxed with stirring for 3 hours under an atmosphere of N$_2$. The organic solvents were removed under vacuum, the residue dissolved in ethyl acetate and washed with water and saturated NaCl solution. After drying (Na$_2$SO$_4$), the solvent was evaporated and the brown residue was purified by column chromatography (ethyl acetate/petrol) and the title compound was obtained as a white powder (0.4 g). $^1$H NMR (250 MHz, DMSO-$d_6$): δ 1.15 (4H, m), 1.70 (4H, m), 2.92 (1H, m), 3.28 (1H, m), 4.51 (1H, d, J=4.3 Hz), 7.23 (1H, t, J=8.5 Hz), 7.42 (1H, t, J=9.2 Hz), 7.66 (2H, m), 7.74 (2H, d, J=8.2 Hz) and 7.90 (2H, d, J=8.2 Hz). MS, m/z: Calcd, 367.11. Found, 367.32 (M).

Synthesis 3

4'-Chloro,2'-fluoro-N-(trans-4-hydroxycyclohexyl)biphenyl-4-sulfonamide (ABD655)

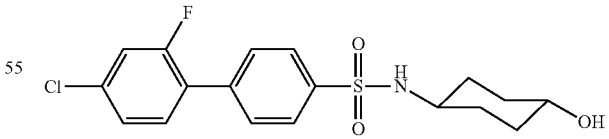

Using a method analogous to Method B, with ABD598 and 4-chloro, 2-fluorophenylboronic acid, the title compound was obtained as a white powder. $^1$H NMR (250 MHz, DMSO-$d_6$): δ 1.11 (4H, m), 1.66 (4H, m), 2.94 (1H, s), 3.30 (1H, s), 4.49 (1H, d, J=4.3 Hz), 7.43 (1H, d, J=8.2 Hz), 7.58 (1H, s), 7.63 (1H, d, J=7.3 Hz), 7.68 (1H, m), 7.76 (2H, d, J=7.6 Hz) and 7.91 (2H, d, J=8.2 Hz). $^{13}$C NMR (62.5 MHz, DMSO-$d_6$): δ 31.1, 33.6, 51.8, 67.6, 116.7, 125.3, 125.9 (d, J=13.7 Hz), 126.5, 129.7, 132.0, 133.9, 137.6, 141.8, 159.0 (d, J=251.0 Hz). MS, m/z: Calcd, 383.076. Found, 383.25 (M).

Synthesis 4

2',4'-Difluorobiphenylsulfonyl chloride

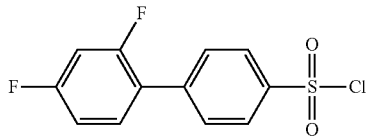 [SMILES: O=S(=O)(Cl)c1ccc(-c2ccc(F)cc2F)cc1]

2,4-Difluorophenylboronic acid (15 g, 129 mmol) was added to a solution of bromobenzene (19.8 g, 126 mmol) in DME (500 mL). To this was added a solution of sodium carbonate (55.8 g, 520 mmol) in water (260 mL). The solution was degassed by bubbling argon through the mixture and then stirred under argon. Pd(dppf)Cl$_2$ (1.5 g, 2.1 mmol) was added and the mixture heated overnight at 90° C. under argon. The mixture was cooled to room temperature and water (150 mL) and ethyl acetate (500 mL) were added. The layers were separated and the organic layer was washed with 2 M NaOH (100 mL), water (100 mL) and brine (100 mL). The black ethyl acetate layer was dried over MgSO$_4$, charcoal was added, and the mixture was filtered through a short pad of silica. Evaporation of the solvents gave 2,4-difluorobiphenyl as a brown oil, which crystallised on standing (21.2 g).

2,4-Difluorobiphenyl (21.2 g, 111 mmol) was dissolved in chloroform (120 mL) and chlorosulfonic acid (12.5 mL, 188 mmol) was added dropwise. The mixture was stirred overnight at room temperature. The reaction mixture was concentrated in vacuo and the residue taken up into EtOAc (100 mL) and washed with water (3×25 mL). The organics were shaken with brine, whereupon a flocculent solid formed. This was filtered and washed with EtOAc and dried to give 2',4'-difluorobiphenyl-4-sulfonic acid as an off-white solid (12.1 g).

2',4'-Difluorobiphenyl-4-sulphonic acid (12.1 g, 47 mmol) was suspended in thionyl chloride (100 mL). The mixture was heated at reflux for 30 minutes, when a catalytic amount of dry DMF was added and the reaction mixture was heated at reflux for a further 4 hours. The reaction mixture was then cooled, the thionyl chloride evaporated and the residue was then azeotroped with toluene (3×10 mL). The resulting yellow/orange gum was taken up into EtOAc (250 mL) and washed with water (50 mL) and brine (50 mL), and dried over MgSO$_4$. Filtration and evaporation gave the title compound as a brown oil which crystallized on standing (11 g).

Synthesis 5

(1R,3S)-Methyl 3-aminocyclopentanecarboxylate hydrochloride

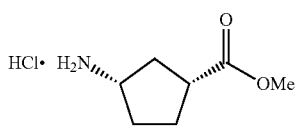

A suspension of (1R,3S)-3-aminocyclopentanecarboxylic acid (500 mg, 3.8 mmol) in methanol (10 mL) was stirred at 0° C. and thionyl chloride (1.40 mL, 19.3 mmol) was added dropwise. The mixture was allowed to warm to room temperature and stirred overnight. The resulting clear solution was evaporated, azeotroped with methanol (2×5 mL), air-dried and the title compound obtained as a white powder (680 mg).

Synthesis 6

(1R,3S)-Methyl 3-(2',4'-difluorobiphenyl-4-ylsulfonamido)cyclopentanecarboxylate (ABD773a)

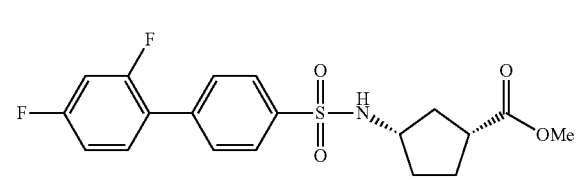 [SMILES: COC(=O)[C@@H]1CC[C@H](NS(=O)(=O)c2ccc(-c3ccc(F)cc3F)cc2)C1]

Using a method analogous to Method A, using (1R,3S)-methyl 3-aminocyclopentanecarboxylate and 2',4'-difluorobiphenyl-4-sulphonyl chloride, the title compound was obtained as a pale yellow gum.

Synthesis 7

2',4'-Difluoro-N-((1S,3R)-3-(hydroxymethyl)cyclopentyl)biphenyl-4-sulfonamide (ABD773)

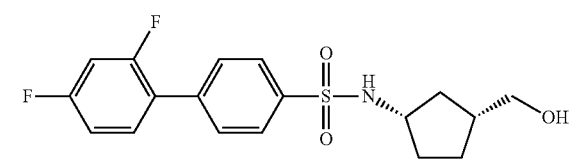

A solution of 1 M LiAlH$_4$ in THF (1.85 mL, 1.85 mmol) was added dropwise to a stirred solution of ABD773a (148 mg, 0.37 mmol) in THF (5 mL) at 0° C., then stirred at room temperature overnight. The mixture was partitioned between water (10 mL) and EtOAc (20 mL), separated and the aqueous layer extracted with further EtOAc (10 mL). The organic phase was washed with brine (10 mL) and dried over MgSO$_4$. The solvent was evaporated, the residue purified by flash chromatography (SiO$_2$, 20% acetone/hexane) and the title compound obtained as a light brown gum (133 mg). $^1$H NMR (300 MHz, CDCl$_3$): δ 1.24-1.27 (2H, m), 1.50-1.58 (2H, m), 1.66-1.76 (2H, m), 1.96-2.08 (1H, m), 2.12-2.22 (1H, m), 3.59 (2H, m), 3.70-3.78 (1H, m), 5.25-5.30 (1H, m), 6.90-7.10 (2H, m), 7.42-7.48 (1H, m), 7.63 (2H, d, J=8 Hz) and 7.93 (2H, d, J=8 Hz). MS, m/z: Calcd, 367.11. Found, 368.07 (M+H).

Synthesis 8

Methyl trans-4-aminocyclohexanecarboxylate

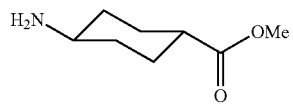

A suspension of trans-4-amino-cyclohexancarboxylic acid (5.0 g, 34.9 mmol) in methanol (50 mL) was stirred at room temperature and SOCl$_2$ (7.14 mL, 11.7 g, 98.4 mmol) was added dropwise over 20 minutes. The solid dissolved, giving a brown solution, which was stirred overnight. The solvent was removed under reduced pressure, giving a brown solid, which was triturated with ether, redissolved in methanol (20 mL) and again evaporated to give a slightly sticky brown solid (6.52 g). A portion of the product (820 mg) was dissolved in methanol (10 mL) and split in two batches, each of which was loaded onto a 5 g SCX column. These were eluted with MeOH (2×10 mL) and then 2 M NH$_3$/MeOH (4×10 mL), and the title compound obtained as a beige solid (425 mg combined).

Synthesis 9

Methyl 4-(2',4'-difluorobiphenyl-4-ylsulfonamido) trans-cyclohexanecarboxylate (ABD776a)

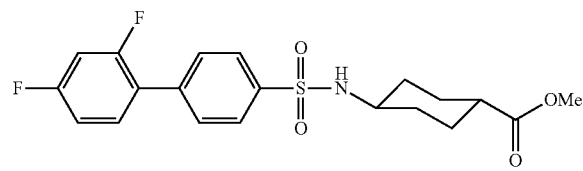 [SMILES: COC(=O)C1CCC(NS(=O)(=O)c2ccc(-c3ccc(F)cc3F)cc2)CC1]

Using a method analogous to Method A with 2',4'-difluorobiphenyl-4-sulfonyl chloride and methyl trans-4-aminocyclohexanecarboxylate, the title compound was obtained as a white solid.

Synthesis 10

2',4'-Difluoro-N-(4-(trans-hydroxymethyl)cyclohexyl)biphenyl-4-sulfonamide (ABD776)

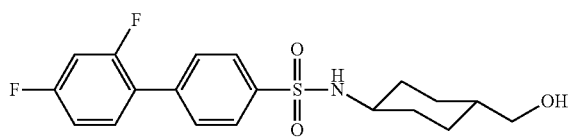 [SMILES: O=S(=O)(NC1CCC(CO)CC1)c1ccc(-c2ccc(F)cc2F)cc1]

A solution of ABD776a (100 mg, 0.24 mmol) in dry THF (10 mL) was cooled to 0° C. under argon and 1 M LiAlH$_4$ in THF (1.22 mL, 1.22 mmol) was added by syringe. The mixture was stirred overnight, allowing it to warm to room temperature. The solution was then cooled to 0° C. before saturated NH$_4$Cl (5 mL) and EtOAc (20 mL) were added. The mixture was filtered through Celite and the layers separated. The aqueous phase was extracted with further EtOAc (3×5 mL) and the combined organics were washed with 1 M HCl (10 mL), water (10 mL) and brine (10 mL) and dried over MgSO$_4$. Evaporation of the solvents afforded a brown gum, which was purified by SP4 chromatography (10 g Isolute II SiO$_2$ cartridge, 10-30% acetone/hexane) to give a light brown gum. Final purification by reverse phase HPLC (40-48.5% NH$_4$OH/H$_2$O in CH$_3$CN) gave the title compound as a white solid (28 mg). $^1$H NMR (400 MHz, CDCl$_3$): δ 0.99 (2H, q, J=9 Hz), 1.18 (2H, q, J=9 Hz), 1.34-1.45 (1H, m), 1.78 (2H, d, J=12 Hz), 1.93 (2H, d, J=12 Hz), 3.07-3.19 (1H, m), 3.42 (2H, t, J=5 Hz), 4.32 (1H, d, J=8 Hz), 6.88-7.02 (2H, m), 7.38-7.46 (1H, m), 7.65 (2H, d, J=8 Hz) and 7.94 (2H, d, J=8 Hz). MS, m/z: Calcd, 381.121. Found, 381.59 (M).

Synthesis 11

4-Bromo-N-(4-oxocyclohexyl)benzenesulfonamide (ABD777b)

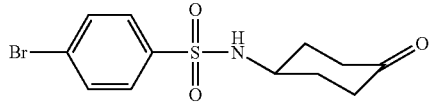 [SMILES: O=C1CCC(NS(=O)(=O)c2ccc(Br)cc2)CC1]

Jones' reagent was prepared by dissolving Cro$_3$ (1.33 g, 13.3 mmol) in concentrated H$_2$SO$_4$ (1.15 mL) and diluting the mixture up to 5 mL with water. A solution of ABD598 (390 mg, 1.17 mmol) in acetone (15 mL) was stirred at room temperature and Jones' reagent was added dropwise until an orange colour persisted. TLC indicated complete consumption of the starting material and the formation of a new, less polar, compound. The mixture was filtered through Celite, the solvent was evaporated and the residue taken up in EtOAc (50 mL). The solution was washed with water (2×10 mL) and 10% aqueous Na$_2$S$_2$O$_3$ (2×10 mL) and dried over MgSO$_4$. Evaporation of the solvent gave the title compound as a white solid (390 mg).

Synthesis 12

4-Bromo-N-(cis-4-hydroxycyclohexyl)benzenesulfonamide (ABD777a)

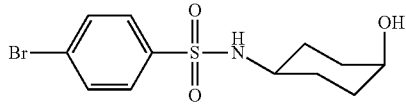 [SMILES: O=S(=O)(NC1CCC(O)CC1)c1ccc(Br)cc1]

A solution of ABD777b (205 mg, 0.62 mmol) in dry THF (5 mL) was cooled to 0° C. under argon. 1 M L S-Selectride in THF (1.32 mL, 1.32 mmol) was added by syringe and the solution was stirred for 1 hour. Water (1 mL) was added and the mixture was stirred for 10 minutes before being diluted with EtOAc (20 mL) and 1 M HCl (4 mL). The layers were separated and the organic phase was washed with water (5 mL) and brine (5 mL) and dried over MgSO$_4$. Evaporation of the solvents afforded a colourless oil which was purified by SP4 chromatography (20 g Isolute II SiO$_2$ cartridge, eluting with 0-40% acetone/hexane) and the title compound obtained as a white solid (165 mg).

Synthesis 13

2',4'-Difluoro-N-(cis-4-hydroxycyclohexyl)biphenyl-4-sulfonamide (ABD777)

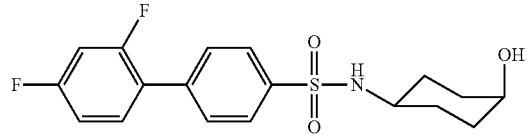

Method C:

ABD777a (160 mg, 0.48 mmol), 2,4-difluorophenylboronic acid (113 mg, 0.72 mmol) and 1 M Na$_2$CO$_3$ solution (1 mL, 1 mmol) were stirred in DME and the flask was flushed with argon. Pd(dppf)Cl$_2$ (17 mg, 0.02 mmol) was added and the flask was placed into an oil bath that had been pre-heated to 90° C. and stirred for 1.5 hours. The mixture was cooled, poured into EtOAc (30 mL) and washed with water (5 mL) and brine (5 mL). The solvents were dried over MgSO$_4$ and evaporated to afford a dark oil, which was purified by SP4 chromatography twice (20 g Isolute II SiO$_2$ column, eluting with 0-40% acetone/hexane, then 10 g Isolute II SiO$_2$ column, eluting with 0-40% acetone/hexane) to give a colourless glassy solid. This was triturated with ether/hexane and the title compound was obtained as a white powder. $^1$H NMR (300 MHz, DMSO-d$_6$): δ 1.24-1.40 (4H, m), 1.40-1.59 (4H, m), 2.98 (1H, br s), 3.55 (1H, br s), 4.32 (1H, d, J=3 Hz), 7.21 (1H, td, J=17, 2 Hz), 7.40 (1H, td, J=20, 3 Hz), 7.60-7.80 (3H, m) and 7.88 (2H, d, J=8 Hz). MS, m/z: Calcd, 367.105. Found, 367.31 (M).

Synthesis 14

Methyl cis-4-aminocyclohexanecarboxylate

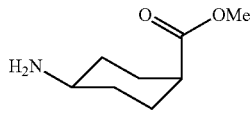

A suspension of cis-4-aminocyclohexanecarboxylic acid (5.0 g, 34.9 mmol) in methanol (50 mL) was stirred at room temperature and SOCl$_2$ (7.1 mL, 98.4 mmol) was added dropwise over 20 minutes, causing the solid to dissolve. The solution was stirred overnight and the methanol was then removed under reduced pressure. The residual solid was triturated with diethyl ether and air-dried and the title compound obtained as an off-white powder (6.0 g).

Synthesis 15

Methyl 4-(4-bromophenylsulfonamido)cis-cyclohexanecarboxylate (ABD781 b)

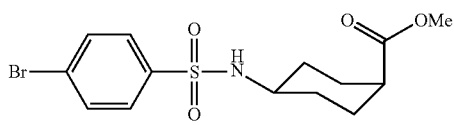 [SMILES: COC(=O)C1CCC(NS(=O)(=O)c2ccc(Br)cc2)CC1]

Using a method analogous to Method A with 4-bromophenylsulfonyl chloride and methyl cis-4-aminocyclohexanecarboxylate, the title compound was obtained as a pale brown solid.

Synthesis 16

Methyl 4-(2',4'-difluorobiphenyl-4-ylsulfonamido) cis-cyclohexanecarboxylate (ABD781a)

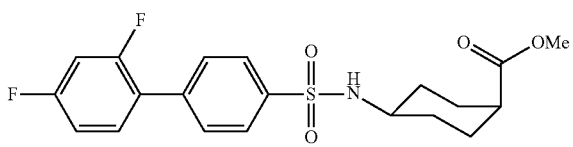 [SMILES: COC(=O)C1CCC(NS(=O)(=O)c2ccc(-c3ccc(F)cc3F)cc2)CC1]

Using a method analogous to Method A with 2',4'-difluorophenylsulfonyl chloride and ABD781b, the title compound was obtained as an orange gum.

Synthesis 17

2',4'-Difluoro-N-(cis-4-(hydroxymethyl)cyclohexyl) biphenyl-4-sulfonamide (ABD781)

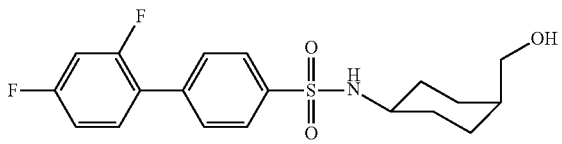 [SMILES: O=S(=O)(NC1CCC(CO)CC1)c1ccc(-c2ccc(F)cc2F)cc1]

A solution of ABD781a (123 mg, 0.30 mmol) in dry THF (3 mL) was cooled under argon to 0° C. and 1 M LiAlH$_4$ in THF (1.5 mL, 1.5 mmol) was added by syringe. The mixture was stirred for 2 hours, whilst warming to room temperature. Ice and water were then added and the mixture was adjusted to pH 2 with 2 M HCl and extracted with EtOAc (4×10 mL). The combined extracts were washed with brine (10 mL), dried over MgSO$_4$ and evaporated. The crude product was purified by column chromatography (SiO$_2$, 30%-40% acetone/hexane) and then trituration with ether/hexane gave the title compound as a white solid (64 mg). $^1$H NMR (300 MHz, CDCl$_3$): δ 1.15-1.30 (2H, m), 1.50-1.70 (7H, m), 3.45-3.56 (3H, m), 4.63 (1H, d, J=7 Hz), 6.91-7.04 (2H, m), 7.43 (1H, td, J=9 Hz, 7 Hz), 7.65 (2H, d, J=8 Hz) and 7.93 (2H, d, J=8 Hz). MS, m/z: Calcd, 381.12. Found, 381.25 (M).

Synthesis 18

2',4'-Difluoro-N-(4-oxocyclohexyl)biphenyl-4-sulfonamide (ABD786)

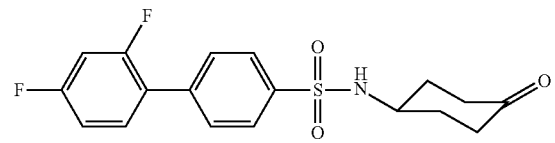 [SMILES: O=C1CCC(NS(=O)(=O)c2ccc(-c3ccc(F)cc3F)cc2)CC1]

Using a method analogous to Method C, with ABD777b and 2,4-difluorophenylboronic acid, the title compound was obtained as a white powder. $^1$H NMR (300 MHz, DMSO-d$_6$): δ 1.63 (2H, m), 1.85 (2H, m), 2.25 (4H, m), 3.51 (1H, br m), 7.22 (1H, td, J=9 Hz, 3 Hz), 7.41 (1H, ddd, J=12 Hz, 8 Hz, 3 Hz), 7.65 (1H, td, J=8 Hz, 7 Hz), 7.74 (2H, dd, J=8 Hz, 2 Hz), 7.92 (2H, d, J=8 Hz) and 7.97 (1H, br s). MS, m/z: Calcd, 365.09. Found, 365.52 (M).

Synthesis 19

2',4'-Difluoro-N-(trans-4-(2-hydroxypropan-2-yl) cyclohexyl)biphenyl-4-sulfonamide

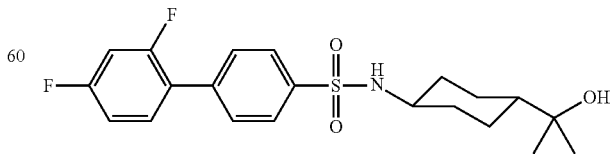

A solution of ABD776a (100 mg, 0.24 mmol) in dry THF (10 mL) was cooled under argon to 0° C. 3 M Methylmagnesium bromide solution in Et$_2$O (25 μL, 0.75 mmol) was added by syringe and the mixture was stirred for 2 hours, allowing it to warm to room temperature. The solution was cooled to 0° C. and saturated NH₄Cl solution (2 mL) was added, followed by water to dissolve the solids. The mixture was extracted with EtOAc (3×10 mL) and the combined extracts were washed with brine (5 mL) and water (5 mL) and dried over MgSO₄. The solvents were evaporated to afford a brown gum, which was purified by SP4 chromatography (10 g Isolute II SiO₂ cartridge, 10-40% acetone/hexane) to give a glassy solid (64 mg). The title compound was obtained as a white solid by reverse phase HPLC (50-55% NH₄OH/CH₃CN) (31 mg). ¹H NMR (400 MHz, CDCl₃): δ 1.13 (6H, s), 1.00-1.30 (4H, m), 1.81 (2H, d, J=12 Hz), 1.95 (2H, d, J=12 Hz), 3.05-3.16 (1H, m), 4.29 (1H, d, J=7 Hz), 6.89-7.02 (2H, m), 7.43 (1H, m), 7.63 (2H, d, J=8 Hz) and 7.93 (2H, d, J=8 Hz). MS, m/z: Calcd, 409.152. Found, 409.59 (M).

Synthesis 20

2',4'-Difluoro-N-(cis-4-(2-hydroxypropan-2-yl)cyclohexyl)biphenyl-4-sulfonamide (ABD7951)

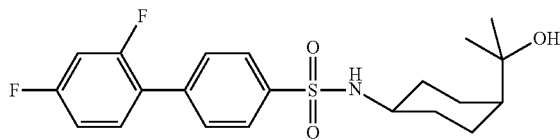 [SMILES: CC(C)(O)C1CCC(NS(=O)(=O)c2ccc(-c3ccc(F)cc3F)cc2)CC1]

A solution of ABD781a (300 mg, 0.73 mmol) in dry THF (10 mL) was cooled under argon to 0° C. and 3 M methylmagnesium bromide in Et₂O (0.97 mL, 2.93 mmol) was added by syringe. The ice bath was removed and the reaction mixture was stirred at room temperature for 1 hour. Saturated NH₄Cl (2 mL) was then added and the mixture was stirred a further 10 minutes before being diluted with water (10 mL) and diethyl ether (20 mL). The layers were separated and the aqueous phase was extracted with diethyl ether (2×10 mL). The combined organics were dried over MgSO₄ and evaporated to give an off-white foamy solid. This was triturated with diethyl ether/hexane (1:1, 3×5 mL) and the title compound obtained as a white powder (250 mg). ¹H NMR (300 MHz, DMSO-d₆): δ 0.96 (6H, s), 1.06 (1H, t, J=6 Hz), 1.16-1.34 (4H, m), 1.39-1.47 (2H, m), 1.53-1.60 (2H, m), 3.22 (1H, br s), 7.22 (1H, t, J=7 Hz), 7.39 (1H, t, J=9 Hz), 7.60-7.70 (1H, m), 7.72 (2H, d, J=8 Hz) and 7.88 (2H, d, J=8 Hz). MS, m/z: Calcd, 409.152. Found, 409.59 (M).

Synthesis 21

(1R,3S)-Methyl 3-(4-bromophenylsulfonamido)cyclopentanecarboxylate (ABD796b)

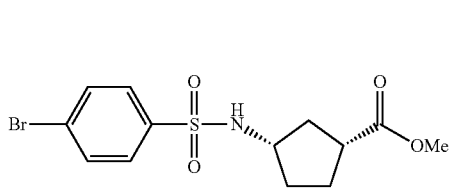 [SMILES: COC(=O)[C@@H]1CC[C@H](NS(=O)(=O)c2ccc(Br)cc2)C1]

Using a method analogous to Method A, with (1R,3S)-methyl 3-aminocyclopentanecarboxylate and 4-bromobenzenesulphonyl chloride, the title compound was obtained as a light brown gum.

Synthesis 22

4-Bromo-N-((1S,3R)-3-(2-hydroxypropan-2-yl)cyclopentyl)benzenesulfonamide (ABD796a)

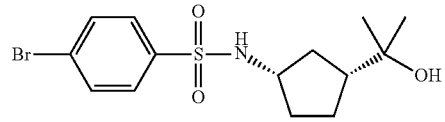 [SMILES: CC(C)(O)[C@@H]1CC[C@H](NS(=O)(=O)c2ccc(Br)cc2)C1]

3 M Methylmagnesium bromide in ether (360 μL, 1.08 mmol) was added to a stirred solution of ABD796b (130 mg, 0.36 mmol) in dry THF (10 mL) at 0° C. The reaction mixture was allowed to warm to room temperature and stirred overnight. Saturated ammonium chloride solution (3 mL) was added and the THF layer was separated. The aqueous phase was extracted with THF (2×10 mL) and the combined organic layers were washed with brine and dried over MgSO₄. Evaporation of the solvent gave the title compound as a brown gum.

Synthesis 23

2',4'-Difluoro-N-((1S,3R)-3-(2-hydroxypropan-2-yl)cyclopentyl)biphenyl-4-sulfonamide (ABD796)

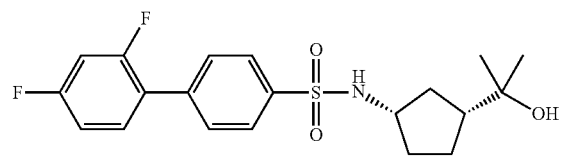 [SMILES: CC(C)(O)[C@@H]1CC[C@H](NS(=O)(=O)c2ccc(-c3ccc(F)cc3F)cc2)C1]

Using a method analogous to Method C with ABD796a and 2,4-difluorophenylboronic acid, the title compound was obtained as a white solid. ¹H NMR (300 MHz, CDCl₃): δ 1.15 (3H, s), 1.18 (3H, s), 1.40-1.45 (2H, m), 1.50-1.70 (4H, m), 1.80-1.95 (2H, m), 3.71-3.74 (1H, m), 5.53 (1H, d, J=9 Hz), 6.90-7.10 (2H, m), 7.35-7.45 (1H, m), 7.63 (2H, d, J=8 Hz) and 7.93 (2H, d, J=8 Hz). MS, m/z: Calcd, 395.137. Found, 395.59 (M).

Synthesis 24

N-(cis-4-(Dimethylamino)cyclohexyl)-2',4'-difluorobiphenyl-4-sulfonamide (ABD798)

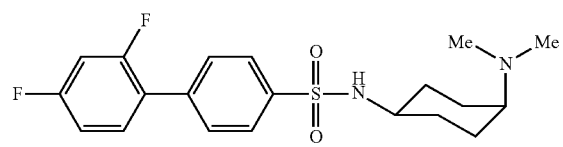 [SMILES: CN(C)C1CCC(NS(=O)(=O)c2ccc(-c3ccc(F)cc3F)cc2)CC1]

A solution of ABD786 (200 mg, 0.55 mmol) in dry THF (5 mL) was stirred at room temperature and 2 M dimethylamine in THF (0.55 mL, 1.10 mmol) was added by syringe. The solution was cooled to 0° C. under argon and sodium triacetoxyborohydride (150 mg, 0.71 mmol) was added in one portion. The reaction mixture was stirred at 0° C. for 1 hour and then at room temperature overnight. TLC indicated incomplete reaction so further 2 M dimethylamine in THF (0.5 mL, 1 mmol) and sodium triacetoxyborohydride (100 mg, 0.47 mmol) were added. After a further 24 hours, 2 M NaOH (3 mL) was added. The layers were separated and the aqueous phase was extracted with diethyl ether (2×10 mL). The combined organic solvents were dried over $MgSO_4$ and then evaporated to afford a viscous yellow oil. This was dissolved in MeOH (5 mL) and loaded onto a 5 g SCX-2 column, which was eluted with MeOH (2×10 mL) and then with 25% 2 M $NH_3$/MeOH in DCM (5×10 mL). The fractions containing a UV-active component were combined and evaporated to afford the target compound as a pale yellow oil (230 mg, 1:1 mixture of isomers). The crude mixture of isomers (150 mg) was separated by preparative HPLC and the title compound obtained as a white solid (28 mg). $^1$H NMR (400 MHz, $CDCl_3$): δ 1.15-1.31 (2H, m), 1.53-1.75 (2H, br s), 1.85 (2H, br d, J=6 Hz), 1.95 (2H, br d, J=6 Hz), 2.13 (1H, br t, J=5 Hz), 2.24 (6H, s), 3.13 (1H, br t, J=5 Hz), 4.35 (1H, br s), 6.92-7.02 (2H, m), 7.44 (1H, td, J=9 Hz, 7 Hz), 7.63 (2H, d, J=8 Hz) and 7.93 (2H, d, J=8 Hz). MS, m/z: Calcd, 394.153. Found, 394.29 (M).

Synthesis 25

N-(trans-4-(Dimethylamino)cyclohexyl)-2',4'-difluorobiphenyl-4-sulfonamide (ABD799)

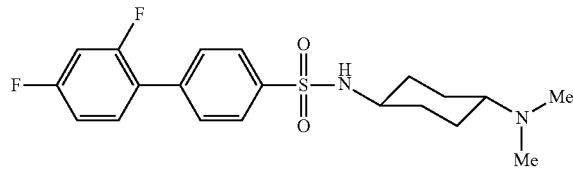 [SMILES: CN(C)C1CCC(NS(=O)(=O)c2ccc(-c3ccc(F)cc3F)cc2)CC1]

The title compound was obtained as a white solid by preparative HPLC of the mixture of isomers obtained in the previous synthesis. $^1$H NMR (400 MHz, $CDCl_3$): δ 1.45-1.75 (8H, m), 2.07 (1H, br s), 2.23 (6H, s), 3.45 (1H, br s), 4.58 (1H, br s), 6.92-7.02 (2H, m), 7.44 (1H, td, J=9 Hz, 7 Hz), 7.63 (2H, d, J=8 Hz) and 7.92 (2H, d, J=8 Hz). MS, m/z: Calcd, 394.153. Found, 394.29 (M).

Synthesis 26

4-Bromo-3-fluoro-N-(trans-4-hydroxycyclohexyl)benzenesulfonamide (ABD665a)

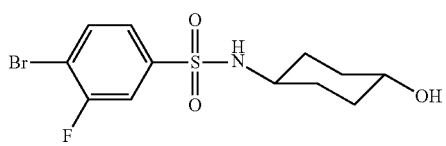 [SMILES: O=S(=O)(NC1CCC(O)CC1)c1ccc(Br)c(F)c1]

Method D:

4-Bromo-3-fluorobenzene sulfonyl chloride (1 g) was dissolved in DCM (30 mL). Trans-4-aminocyclohexanol (1 g) was added and the mixture stirred overnight. Pyridine (3 mL) was added and the mixture was stirred for 3 hours, poured into 2 M HCl and separated. The organic phase was collected and the aqueous phase washed with ethyl acetate. The two organic phases were combined and the resultant solution was dried and evaporated to give an off-white residue. The residue was recrystallised from diethyl ether/petrol, to give the title compound as a white powder.

Synthesis 27

2-Fluoro-N-(trans-4-hydroxycyclohexyl)-4'-(trifluoromethoxy)biphenyl-4-sulfonamide (ABD665)

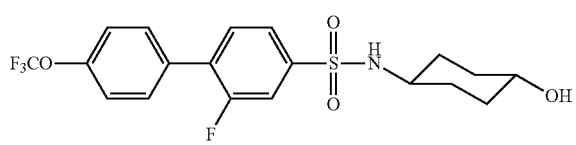

Using a method analogous to Method B, with ABD665a and 4-trifluoromethoxyphenylboronic acid, the title compound was obtained as a white powder. $^1$H NMR (250 MHz, DMSO-$d_6$): δ 1.06-1.20 (4H, m), 1.66 (4H, m), 2.97 (1H, br s), 3.32 (1H, br s), 4.51 (1H, d, J=4.3 Hz), 7.52 (2H, d, J=8.2 Hz), and 7.74 (6H, m).

Synthesis 28

2',5'-Difluoro-N-(trans-4-hydroxycyclohexyl)biphenyl-4-sulfonamide (ABD679)

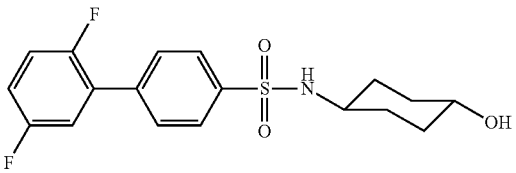 [SMILES: O=S(=O)(NC1CCC(O)CC1)c1ccc(-c2cc(F)ccc2F)cc1]

Using a method analogous to Method B, with ABD598 and 2,5-difluorophenylboronic acid, the title compound was obtained as a white powder. $^1$H NMR (300 MHz, DMSO-$d_6$): δ1.02-1.20 (4H, m), 1.60-1.72 (4H, m), 2.94 (1H, m), 3.29 (1H, m), 4.49 (1H, d, J=4.2 Hz), 7.32 (1H, m), 7.42 (1H, m), 7.52 (1H, m), 7.73 (1H, d, J=7.2 Hz), 7.76 (2H, d, J=7.8 Hz), and 7.90 (2H, d, J=8.7 Hz). MS, m/z: Calcd, 367.11. Found, 366.1 (M−1).

Synthesis 29

2'-Chloro-N-(trans-4-hydroxycyclohexyl)biphenyl-4-sulfonamide (ABD682)

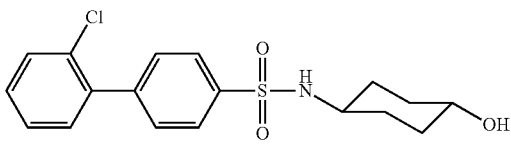 [SMILES: O=S(=O)(NC1CCC(O)CC1)c1ccc(-c2ccccc2Cl)cc1]

Using a method analogous to Method B, with ABD598 and 2-chlorophenylboronic acid, the title compound was obtained as a white powder. ¹H NMR (300 MHz, DMSO-d₆): δ 1.01-1.20 (4H, m), 1.60-1.72 (4H, m), 2.94 (1H, m), 3.29 (1H, m), 4.47 (1H, d, J=4.2 Hz), 7.45 (3H, m), 7.59 (1H, m), 7.63 (2H, d, J=8.4 Hz), 7.72 (1H, m), and 7.88 (2H, d, J=8.4 Hz). MS, m/z: Calcd, 365.09. Found, 364.6 (M−1).

Synthesis 30

N-(trans-4-Hydroxycyclohexyl)-3'-(trifluoromethyl)biphenyl-4-sulfonamide (ABD683)

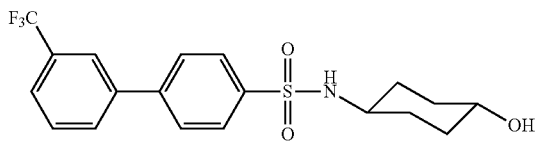 [SMILES: O=S(=O)(NC1CCC(O)CC1)c1ccc(-c2cccc(C(F)(F)F)c2)cc1]

Using a method analogous to Method B, with ABD598 and 3-trifluoromethylphenylboronic acid, the title compound was obtained as a white powder. ¹H NMR (300 MHz, DMSO-d₆): δ 1.00-1.20 (4H, m), 1.59-1.71 (4H, m), 2.92 (1H, m), 3.30 (1H, m), 4.47 (1H, d, J=4.2 Hz), 7.68-7.78 (3H, m), 7.89 (2H, d, J=8.4 Hz), 7.97 (2H, d, J=8.4 Hz), and 8.06 (2H, m). MS, m/z: Calcd, 399.11. Found, 398.5 (M−1).

Synthesis 31

4-Bromo-N-(trans-4-hydroxycyclohexyl)-2-(trifluoromethoxy)benzenesulfonamide (ABD684a)

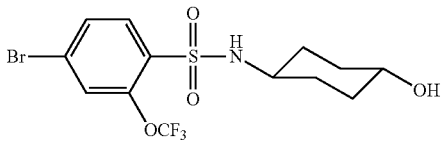

Using a method analogous to Method D, with 4-bromo-2-trifluoromethoxybenzene sulfonyl chloride and trans-4-aminocyclohexanol, the title compound was obtained as a white powder.

Synthesis 32

N-(trans-4-Hydroxycyclohexyl)-4'-methyl-3-(trifluoromethoxy)biphenyl-4-sulfonamide (ABD6841

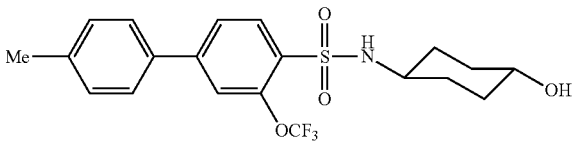 [SMILES: Cc1ccc(-c2ccc(S(=O)(=O)NC3CCC(O)CC3)c(OC(F)(F)F)c2)cc1]

Using a method analogous to Method B, with ABD684a and 4-methylphenylboronic acid, the title compound was obtained as a white powder. ¹H NMR (300 MHz, DMSO-d₆): δ 1.07 (2H, m), 1.25 (2H, m), 1.63 (2H, m), 1.72 (2H, m), 2.36 (3H, s), 3.05 (1H, m), 3.27 (1H, m), 4.49 (1H, d, J=4.2 Hz), 7.32 (2H, d, J=8.1 Hz), 7.66 (2H, d, J=8.1 Hz), 7.69 (1H, s), 7.84 (2H, m) and 7.97 (1H, d, J=8.4 Hz). MS, m/z: Calcd, 429.12. Found, 428.5 (M−1).

Synthesis 33

2',4'-Difluoro-N-(trans-4-hydroxycyclohexyl)-3-(trifluoromethoxy)biphenyl-4-sulfonamide (ABD689)

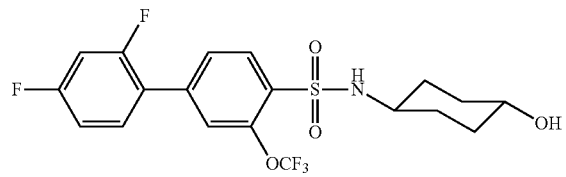 [SMILES: O=S(=O)(NC1CCC(O)CC1)c1ccc(-c2ccc(F)cc2F)cc1OC(F)(F)F]

Using a method analogous to Method B, with ABD684a and 2,4-difluorophenylboronic acid, the title compound was obtained as a white powder. ¹H NMR (300 MHz, DMSO-d₆): δ 1.08 (2H, m), 1.23 (2H, m), 1.63-1.76 (4H, m), 3.09 (1H, m), 3.31 (1H, m), 4.50 (1H, m), 7.26 (1H, t, J=8.4 Hz), 7.48 (1H, t, J=9.0 Hz), 7.65 (1H, s), 7.71 (2H, m), 7.92 (1H, d, J=7.5 Hz) and 8.01 (1H, d, J=8.1 Hz). MS, m/z: Calcd, 451.09. Found, 450.5 (M−1).

Synthesis 34

2',4'-Difluoro-N-(trans-4-hydroxycyclohexyl)-3-methylbiphenyl-4-sulfonamide (ABD699)

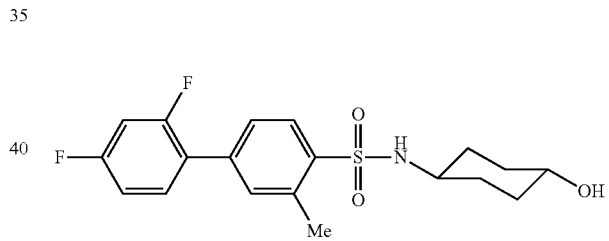

Using a method analogous to Method D, with 2',4'-difluoro-3-methylbiphenyl sulfonyl chloride and trans-4-aminocyclohexanol, the title compound was obtained as a clear oil which solidified on standing. ¹H NMR (250 MHz, DMSO-d₆): δ 1.10 (2H, m), 1.29 (2H, m), 1.58-1.75 (4H, m), 2.62 (3H, s), 2.94 (1H, br s), 3.31 (1H, br s), 4.50 (1H, s), 7.20 (1H, br t), 7.37 (1H, br t), 7.52 (2H, m), 7.63 (1H, br d), 7.72 (1H, br d) and 7.90 (1H, br d).

Synthesis 35

4-Bromo-N-(trans-4-hydroxycyclohexyl)-3-methylbenzenesulfonamide (ABD702a)

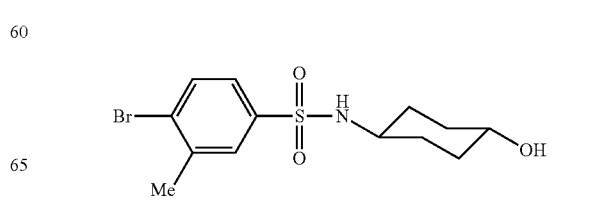

Using a method analogous to Method D, with 4-bromo-3-methylbenzene sulfonyl chloride and trans-4-aminocyclohexanol, the title compound was obtained as a white powder.

Synthesis 36

4'-Fluoro-N-(trans-4-hydroxycyclohexyl)-2-methyl-biphenyl-4-sulfonamide (ABD702)

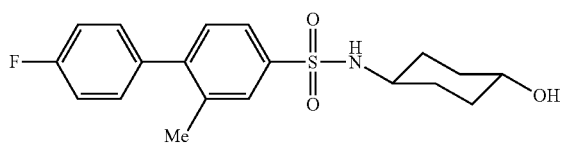 [SMILES: Cc1cc(S(=O)(=O)NC2CCC(O)CC2)ccc1-c1ccc(F)cc1]

Using a method analogous to Method B, with ABD702a and 2,4-difluorophenylboronic acid, the title compound was obtained as a white powder. $^1$H NMR (300 MHz, DMSO-d$_6$): δ 1.05-1.21 (4H, m), 1.71 (4H, m), 2.29 (3H, s), 2.91 (1H, m), 3.30 (1H, m), 4.47 (1H, m), 7.29 (2H, t, J=9.0 Hz), 7.43 (3H, m), 7.67 (2H, m) and 7.89 (1H, s). MS, m/z: Calcd, 363.13. Found, 362.73 (M).

Synthesis 37

4'-Cyano-N-(trans-4-hydroxycyclohexyl)-2-methyl-biphenyl-4-sulfonamide (ABD703)

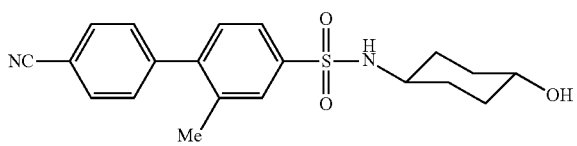 [SMILES: Cc1cc(S(=O)(=O)NC2CCC(O)CC2)ccc1-c1ccc(C#N)cc1]

Using a method analogous to Method B, with ABD702a and 4-cyanophenylboronic acid, the title compound was obtained as a white powder. $^1$H NMR (300 MHz, DMSO-d$_6$): δ 1.05-1.21 (4H, m), 1.70 (4H, m), 2.29 (3H, s), 2.93 (1H, m), 3.28 (1H, m), 4.47 (1H, d. J=4.2 Hz), 7.43 (1H, d, J=8.1 Hz), 7.62 (2H, d, J=8.1 Hz), 7.68 (2H, m), 7.75 (1H, s) and 7.89 (2H, d, J=8.1 Hz). MS, m/z: Calcd, 370.14. Found, 369.7 (M).

Synthesis 38

4-Bromo-2-chloro-N-(trans-4-hydroxycyclohexyl)benzenesulfonamide (ABD704a)

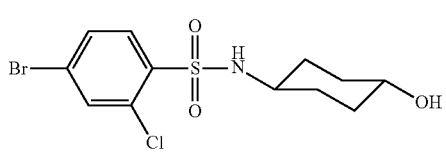 [SMILES: O=S(=O)(NC1CCC(O)CC1)c1ccc(Br)cc1Cl]

Using a method analogous to Method D, with 4-bromo-2-chlorobenzene sulfonyl chloride and trans-4-aminocyclohexanol, the title compound was obtained as a white powder.

Synthesis 39

3-Chloro-N-(trans-4-hydroxycyclohexyl)-4'-methyl-biphenyl-4-sulfonamide (ABD704)

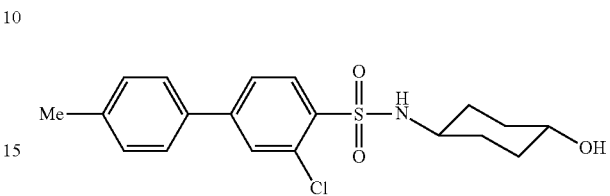

Using a method analogous to Method B, with ABD704a and 4-methylphenylboronic acid, the title compound was obtained as a white powder. $^1$H NMR (300 MHz, DMSO-d$_6$): δ 1.70 (2H, m), 1.88 (2H, m), 2.22 (4H, m), 2.37 (3H, s), 3.57 (1H, m), 7.33 (2H, d, J=7.2 Hz), 7.70 (2H, d, J=8.1 Hz), 7.83 (1H, d, J=8.4 Hz), 7.95 (1H, s), 8.06 (1H, d, J=8.1 Hz) and 8.15 (1H, d, J=7.5 Hz). MS, m/z: Calcd, 379.10. Found, 378.20 (M−1).

Synthesis 40

3-Chloro-2',4'-difluoro-N-(trans-4-hydroxycyclohexyl)biphenyl-4-sulfonamide (ABD705)

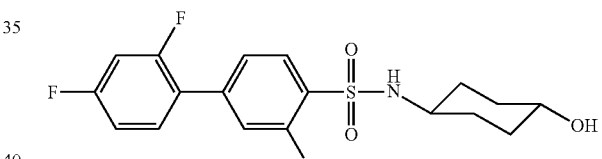

Using a method analogous to Method B, with ABD704a and 2,4-difluorophenylboronic acid, the title compound was obtained as a white powder. $^1$H NMR (DMSO-d$_6$): δ 1.08 (2H, m), 1.26 (2H, m), 1.67 (4H, m), 2.99 (1H, br s), 3.28 (1H, m), 4.51 (1H, d, J=4.3 Hz), 7.24 (1H, t, J=9.1 Hz), 7.43 (1H, t, J=9.1 Hz), 7.69 (1H, d, J=7.9 Hz), 7.72 (1H, d, J=7.9 Hz), 7.81 (1H, s), 7.93 (1H, d, J=7.6 Hz) and 8.07 (1H, d, J=8.2 Hz).

Synthesis 41

4'-Ethoxy-2-fluoro-N-(trans-4-hydroxycyclohexyl)biphenyl-4-sulfonamide (ABD706)

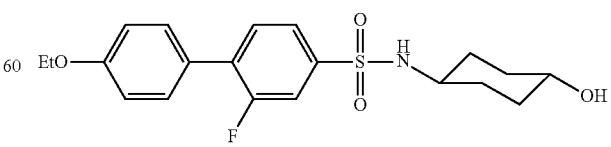

Using a method analogous to Method B, with ABD665a and 4-ethoxyphenylboronic acid, the title compound was obtained as a white powder. $^1$H NMR (300 MHz, DMSO-d$_6$):

δ 1.05-1.16 (4H, m), 1.34 (3H, t, J=6.9 Hz), 1.69 (4H, m), 2.94 (1H, m), 3.29 (1H, m), 4.08 (2H, q, J=6.9 Hz), 4.48 (1H, d. J=4.2 Hz), 7.05 (2H, d, J=8.7 Hz), 7.55 (2H, d, J=7.2 Hz) and 7.66-7.77 (4H, m). MS, m/z: Calcd, 393.14. Found, 392.47 (M−1).

Synthesis 42

2-Fluoro-N-(trans-4-hydroxycyclohexyl)-4'-methoxybiphenyl-4-sulfonamide (ABD710)

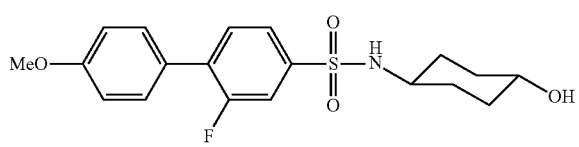 [SMILES: COc1ccc(-c2ccc(S(=O)(=O)NC3CCC(O)CC3)cc2F)cc1]

Using a method analogous to Method B, with ABD665a and 4-methoxyphenylboronic acid, the title compound was obtained as a white powder. $^1$H NMR (DMSO-$d_6$): δ 1.15 (4H, m), 1.70 (4H, m), 2.99 (1H, br s), 3.32 (1H, m), 3.81 (3H, s), 4.50 (1H, s), 7.06 (2H, d, J=7.9 Hz), 7.55 (2H, d, J=7.9 Hz), 7.70 (3H, m) and 7.82 (1H, d, J=7.9 Hz).

Synthesis 43

4'-Chloro-N-(trans-4-hydroxycyclohexyl)-3'-(trifluoromethyl)biphenyl-4-sulfonamide (ABD712)

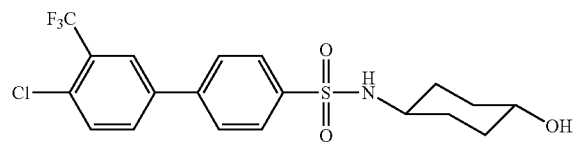 [SMILES: O=S(=O)(NC1CCC(O)CC1)c1ccc(-c2ccc(Cl)c(C(F)(F)F)c2)cc1]

Using a method analogous to Method B, with ABD598 and 4-chloro-3-trifluoromethylphenylboronic acid, the title compound was obtained as a white powder. $^{13}$C NMR (DMSO-$d_6$): δ 31.1, 33.6, 51.8, 67.6, 126.8, 127.1, 127.3, 127.6, 127.9, 130.8, 132.5, 138.1, 140.8, and 142.0. $^1$H NMR (DMSO-$d_6$): δ 1.05-1.22 (4H, m), 1.70 (4H, m), 2.93 (1H, br s), 3.32 (1H, br s), 4.51 (1H, d, J=4.0 Hz), 7.75 (1H, d, J=7.0 Hz), 7.82 (1H, d, J=8.5 Hz), 7.91 (2H, d, J=8.5 Hz), 7.97 (2H, d, J=7.6 Hz), 8.05 (1H, d, J=7.9 Hz) and 8.12 (1H, s).

Synthesis 44

2-Fluoro-N-(trans-4-hydroxycyclohexyl)-4'-(trifluoromethyl)biphenyl-4-sulfonamide (ABD714)

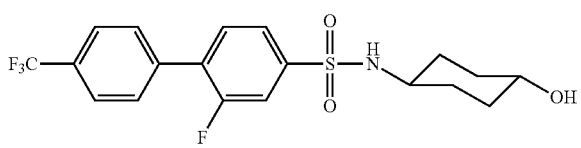

Using a method analogous to Method B, with ABD665a and 4-trifluoromethylphenylboronic acid, the title compound was obtained as a white powder. $^1$H NMR (300 MHz, DMSO-$d_6$): δ 1.05-1.17 (4H, m), 1.68 (4H, m), 2.96 (1H, m), 3.29 (1H, m), 4.49 (1H, d. J=4.2 Hz) and 7.59-7.87 (7H, m). MS, m/z: Calcd, 417.10. Found, 416.3 (M−1).

Synthesis 45

4'-Acetyl-3-chloro-N-(trans-4-hydroxycyclohexyl)biphenyl-4-sulfonamide (ABD716)

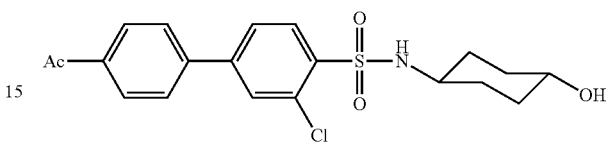

Using a method analogous to Method B, with ABD704a and 4-acetylphenylboronic acid, the title compound was obtained as a white powder. $^1$H NMR (300 MHz, DMSO-$d_6$): δ 1.06 (2H, m), 1.23 (2H, m), 1.63-1.76 (4H, m), 2.62 (3H, s), 2.97 (1H, m), 3.28 (1H, m), 4.48 (1H, d, J=4.2 Hz), 7.90 (2H, m), 7.95 (2H, d, J=8.4 Hz), 8.04 (2H, m) and 8.07 (2H, d, J=9.0 Hz). MS, m/z: Calcd, 407.10. Found, 406.5 (M−1), 408.3 (M+1).

Synthesis 46

4-Bromo-2-ethyl-N-(trans-4-hydroxycyclohexyl)benzenesulfonamide (ABD730a)

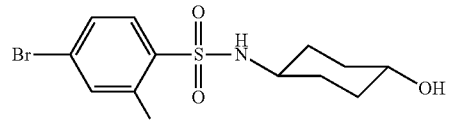

Using a method analogous to Method D, with 4-bromo-2-ethylbenzene sulfonyl chloride and trans-4-aminocyclohexanol, the title compound was obtained as a white powder.

Synthesis 47

3-Ethyl-2',4'-difluoro-N-(trans-4-hydroxycyclohexyl)biphenyl-4-sulfonamide (ABD730)

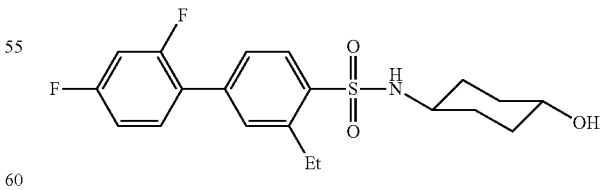

Using a method analogous to Method B, with ABD730a and 2,4-difluorophenylboronic acid, the title compound was obtained as a white powder. $^1$H NMR (300 MHz, DMSO-$d_6$): δ 1.08 (2H, m), 1.23 (2H, m), 1.25 (3H, t, J=7.3 Hz), 1.68 (4H, m), 2.97 (1H, m), 3.01 (2H, q, J=7.3 Hz), 3.26 (1H, m), 4.48 (1H, d, J=4.5 Hz), 7.23 (1H, t, J=8.4 Hz), 7.43 (1H, t, J=9.0

Hz), 7.53 (1H, d, J=8.1 Hz), 7.56 (1H, s), 7.63 (1H, m), 7.75 (1H, d, J=7.8 Hz) and 7.92 (1H, d, J=8.1 Hz). MS, m/z: Calcd, 395.14. Found, 394.3 (M−1).

Synthesis 48

3-Chloro-4'-cyano-N-(trans-4-hydroxycyclohexyl)biphenyl-4-sulfonamide (ABD732)

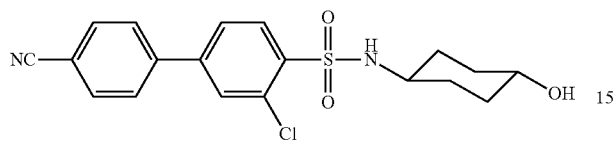

Using a method analogous to Method B, with ABD704a and 4-cyanophenylboronic acid, the title compound was obtained as a white powder. $^{13}$C NMR (DMSO-$d_6$): δ 31.0, 33.7, 51.9, 67.7, 111.6, 118.6, 126.3, 128.2, 130.2, 131.2, 131.5, 133.0, 138.8, 141.5 and 143.2. $^{1}$H NMR (DMSO-$d_6$): δ 1.03 (2H, m), 1.31 (2H, m), 1.67 (4H, m), 2.97 (1H, br s), 3.30 (1H, br s), 4.51 (1H, d, J=4.0 Hz) and 7.87-8.10 (8H, m).

Synthesis 49

2',4'-Difluoro-N-(trans-4-hydroxycyclohexyl)-2-methylbiphenyl-4-sulfonamide (ABD735)

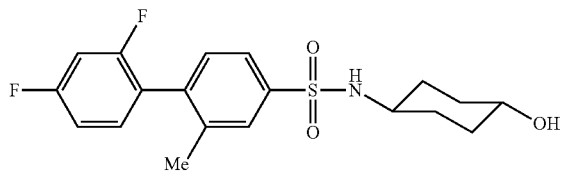 [SMILES: Cc1cc(S(=O)(=O)NC2CCC(O)CC2)ccc1-c1ccc(F)cc1F]

Using a method analogous to Method B, with ABD702a and 2,4-difluorophenylboronic acid, the title compound was obtained as a white powder. $^{1}$H NMR (DMSO-$d_6$): δ 1.11 (4H, m), 1.68 (4H, m), 2.20 (3H, s), 2.93 (1H, br s), 3.32 (1H, br s), 4.50 (1H, s), 7.19 (1H, m), 7.39 (1H, m), 7.40 (2H, d, J=8.2 Hz), 7.69 (2H, m) and 7.77 (1H, s). $^{13}$C NMR (DMSO-$d_6$): δ 19.6, 31.1, 33.6, 51.7, 67.6, 104.2 (m), 111.9 (m), 123.4, 123.7, 127.5 (dd, J=14.7, 8.7 Hz), 130.9, 132.7, 137.5, 138.0, 142.0, 158.8 (dd, J=246.1, 11.7 Hz) and 162.0 (dd, J=250.0, 13.7 Hz). MS, m/z: Calcd, 381.12. Found, 380.7 (M).

Synthesis 50

N-(trans-4-Hydroxycyclohexyl)-2-methyl-4'-(trifluoromethoxy)biphenyl-4-sulfonamide

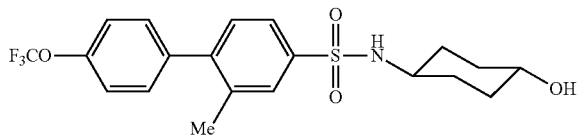 [SMILES: Cc1cc(S(=O)(=O)NC2CCC(O)CC2)ccc1-c1ccc(OC(F)(F)F)cc1]

Using a method analogous to Method B, with ABD702a and 4-trifluoromethoxyphenylboronic acid, the title compound was obtained as a white powder. $^{1}$H NMR (250 MHz, DMSO-$d_6$): δ 1.06-1.22 (4H, m), 1.70 (4H, m), 2.30 (3H, s), 2.94 (1H, br s), 3.31 (1H, br s), 4.51 (1H, d, J=4.3 Hz), 7.43 (3H, m), 7.53 (2H, d, J=8.5 Hz), 7.69 (2H, m) and 7.76 (1H, s). $^{13}$C NMR (250 MHz, DMSO-$d_6$): δ 20.2, 31.1, 33.6, 51.7, 67.6, 120.9, 123.9, 128.0, 130.4, 130.9, 136.2, 139.1, 141.4, 143.4 and 147.9.

Synthesis 51

2',4'-Dichloro-N-(trans-4-hydroxycyclohexyl)-3-(trifluoromethoxy)biphenyl-4-sulfonamide (ABD756)

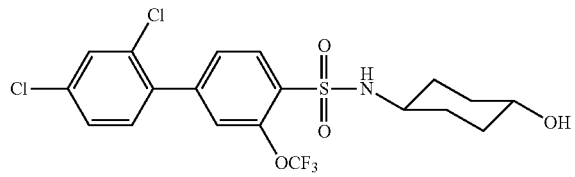

Using a method analogous to Method B, with ABD684a and 2,4-dichlorophenylboronic acid, the title compound was obtained as a white powder. $^{1}$H NMR (250 MHz, DMSO-$d_6$): δ 1.10 (2H, m), 1.27 (2H, m), 1.69 (4H, m), 3.08 (1H, br s), 3.32 (1H, br s), 4.52 (1H, d. J=4.3 Hz), 7.58 (3H, m), 7.62 (1H, d, J=8.2 Hz), 7.80 (1H, s), 7.93 (1H, br d) and 8.02 (1H, d, J=7.9 Hz).

Synthesis 52

Ethyl-cis-2-(2',4'-difluorobiphenyl-4-ylsulfonamido)cyclopentane carboxylate (ABD769a)

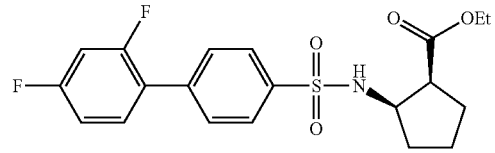 [SMILES: CCOC(=O)[C@H]1CCC[C@H]1NS(=O)(=O)c1ccc(-c2ccc(F)cc2F)cc1]

Ethyl cis-2-aminocyclopentanecarboxylate hydrochloride (390 mg, 2.0 mmol) and 2',4'-difluorobiphenylsulfonyl chloride (480 mg, 1.67 mmol) were stirred in DCM (5 mL) and pyridine (400 μL) was added. The mixture was stirred at room temperature overnight, after which TLC indicated both starting materials were still present. DMAP (10 mg) and additional pyridine (1 mL) were added and stirring was continued for a further 24 hours, when TLC indicated no starting materials remained and a new compound had formed. The reaction mixture was diluted with DCM (10 mL) and water (5 mL) and conc. HCl (1.5 mL) was added and the mixture was stirred for 10 minutes. The layers were separated and the DCM was washed with water (2×5 mL), dried (hydrophobic membrane) and evaporated. The crude product was purified by chromatography on SiO$_2$ (70 g Isolute II cartridge, SP4), eluting with 0-40% acetone/hexane to give the title compound as a pale yellow solid (410 mg, 60%).

Synthesis 53

2',4'-Difluoro-N-(cis-2-(hydroxymethyl)cyclopentyl) biphenyl-4-sulfonamide (ABD769)

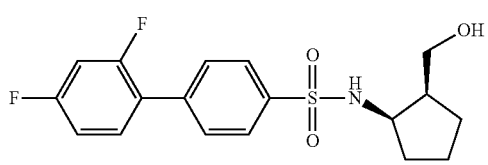 [SMILES: O=S(=O)(N[C@@H]1CCC[C@@H]1CO)c1ccc(-c2ccc(F)cc2F)cc1]

A solution of ABD769a (100 mg, 0.24 mmol) in dry THF (5 mL) was cooled under argon to 0° C. and LiAlH$_4$ (1 M in THF, 1.22 mL, 1.22 mmol) was added by syringe. The ice bath was removed after 15 minutes and the solution was stirred overnight at room temperature. The mixture was then cooled back to 0° C. and dry THF (10 mL) was added, followed by Na$_2$SO$_4$.10H$_2$O (~1 g). The suspension was stirred for 1 hour at room temperature and then filtered. Evaporation of the solvents afforded a colourless glassy solid, which was triturated with ether and hexane at low temperature to give the title compound as a white powder (64 mg, 73%). $^1$H NMR (300 MHz, DMSO-d$_6$): δ 1.20-1.65 (6H, m), 1.89 (1H, br s), 3.15-3.25 (1H, m), 3.43-3.58 (2H, m), 7.21 (1H, t, J=8 Hz), 7.40 (1H, t, J=10 Hz), 7.64 (1H, q, J=8 Hz), 7.70 (2H, d, J=8 Hz) and 7.86 (2H, d, J=8 Hz).

Synthesis 54

N-(cis-4-Aminocyclohexyl)-2',4'-difluorobiphenyl-4-sulfonamide (ABD812)

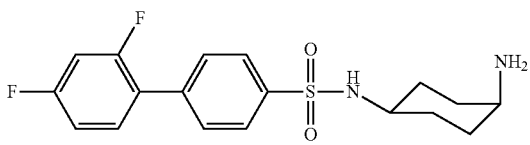 [SMILES: NC1CCC(NS(=O)(=O)c2ccc(-c3ccc(F)cc3F)cc2)CC1]

N-(cis-4-(2,4-Dimethoxybenzylamino)cyclohexyl)-2',4'-difluorobiphenyl-4-sulfonamide (see ABD787a) (52 mg, 0.10 mmol) was stirred in acetonitrile (3 mL) and water (1 mL) and ceric ammonium nitrate (144 mg, 0.26 mmol) was added. The mixture was stirred at 50° C. overnight and then diluted with EtOAc (15 mL) and washed with water (2×5 mL). The washings were extracted with EtOAc (5 mL) and the combined organics were dried over MgSO$_4$. After evaporation of the solvents, the residue was loaded onto a 1 g SCX column and eluted with MeOH and then 20% 2 M NH$_3$/MeOH in DCM. The resulting material was further purified by chromatography (2 g Isolute II cartridge), eluting with 0-10% 2 M NH$_3$/MeOH in DCM to afford the title compound as an off-white powder (9 mg, 25%). $^1$H NMR (300 MHz, DMSO-d$_6$): δ 0.86-0.98 (2H, m), 1.09-1.26 (2H, m), 1.55-1.68 (4H, m), 2.40 (1H, br s), 2.87 (1H, br s), 4.12 (1H, br s), 7.22 (1H, td, J=8 Hz, 2 Hz), 7.40 (1H, td, J=10 Hz, 2.5 Hz), 7.65 (1H, q, J=7 Hz), 7.71 (2H, d, J=9 Hz) and 7.85 (2H, d, J=9 Hz). LCMS: (MH)$^+$=367.

Synthesis 55

(1S,3S)-Methyl 3-(2',4'-difluorobiphenyl-4ylsulfonamido)cyclopentane carboxylate (ABD813a)

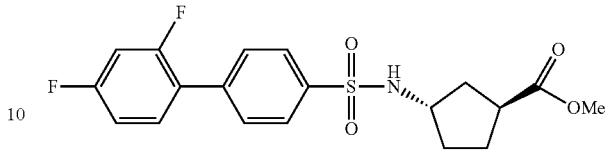

Using a method analogous to Method A, with methyl (1S, 3S)-3-aminocyclopentanecarboxylate hydrochloride and 2',4'-difluorobiphenylsulfonyl chloride, the title compound was obtained as a pale yellow solid (61%).

Synthesis 56

2',4'-Difluoro-N-((1S,3S)-3-(hydroxymethyl)cyclopentyl)biphenyl-4-sulfonamide (ABD813)

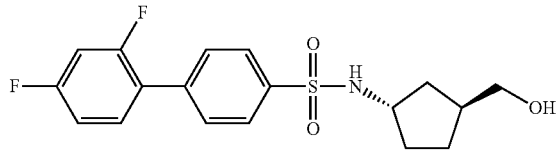

A solution of ABD813a (105 mg, 0.27 mmol) in dry THF (5 mL) was cooled under argon to 0° C. and LiAlH$_4$ (1 M in THF, 1.33 mL, 1.33 mmol) was added by syringe. After 5 minutes the ice bath was removed and the solution was stirred at room temperature for 2 hours. After cooling back to 0° C., the reaction was quenched by adding Na$_2$SO$_4$10.H$_2$O (~500 mg) cautiously. Once bubbling had stopped the mixture was diluted with EtOAc (10 mL) and stirred for 1 hour at room temperature before being filtered, rinsing the solids well with EtOAc. Evaporation of the solvent afforded the crude product as a colourless glassy solid which was purified by repeated chromatography on SiO$_2$ (acetone/hexane) and finally trituration with Et$_2$O, to give the title compound as a white powder (6 mg, 6%). $^1$H NMR (300 MHz, CDCl$_3$): δ 1.20-1.52 (3H, m), 1.60-1.73 (2H, m), 1.76-1.90 (2H, m), 2.24 (1H, quintet, J=7 Hz), 3.48 (2H, br s), 3.71 (1H, q, J=6 Hz), 4.56 (1H, d, J=7 Hz), 6.94-7.00 (2H, m), 7.43 (1H, q, J=7 Hz), 7.64 (2H, d, J=8 Hz) and 7.93 (2H, d, J=8 Hz). LCMS: (MH)$^+$=368.

Synthesis 57

2',4'-Difluoro-((1S,3S)-3-(2-hydroxypropan-2yl) cyclopentyl) biphenyl-4-sulfonamide (ABD815)

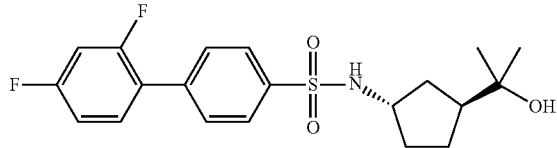

A solution of ABD813a (105 mg, 0.27 mmol) in dry THF (5 mL) was cooled under argon to 0° C. and MeMgBr (3 M in Et$_2$O, 440 μL, 1.33 mmol) was added by syringe and the solution was stirred for 2 hours. TLC indicated some starting material remaining, and so further MeMgBr (3 M in Et$_2$O, 440 μL, 1.33 mmol) was added and stirring continued at room temperature for a further 2 hours. The mixture was diluted with Et$_2$O (30 mL) and quenched with NH$_4$Cl (sat. aq., 10 mL). The layers were separated and the aqueous phase was extracted with further Et$_2$O (10 mL) and the combined organics were washed with brine (10 mL) and dried over MgSO$_4$. After evaporation of the solvent the crude product was purified by chromatography on SiO$_2$ (20% acetone/hexane) to give the title compound as a colourless gum (77 mg, 72%). $^1$H NMR (300 MHz, CDCl$_3$): δ 1.12 (3H, s), 1.13 (3H, s), 1.45-1.75 (6H, m), 1.84-1.97 (1H, m), 2.07 (1H, t, J=8 Hz), 3.68 (1H, q, J=5 Hz), 4.60 (1H, d, J=7 Hz), 6.94-7.00 (2H, m), 7.42 (1H, td, J=8 Hz, 6 Hz), 7.64 (2H, dd, J=8 Hz, 2 Hz) and 7.93 (2H, d, J=8 Hz). LCMS: (MH)$^+$=396.

Synthesis 58

2',4'-Difluoro-N-(4-(methylamino)cyclohexyl)biphenyl-4-sulfonamide (ABD816)

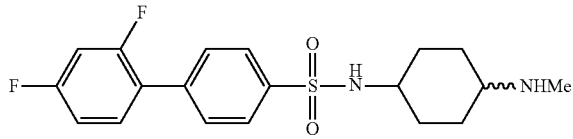 [SMILES: CNC1CCC(NS(=O)(=O)c2ccc(-c3ccc(F)cc3F)cc2)CC1]

A solution of ABD786 (250 mg, 0.68 mmol) in dry THF (5 mL) was stirred under argon and methylamine (2 M in THF, 1.35 mL) was added by syringe. The solution was stirred for 1 hour and then STAB (360 mg, 1.7 mmol) was added in one portion. The mixture was stirred at room temperature overnight. TLC indicated starting material to still be present, and so further methylamine (2 M in THF, 1.35 mL) and STAB (360 mg, 1.7 mmol) and a drop of acetic acid were added and stirring was continued for a further 3 days. The reaction was quenched by the addition of 2 M NaOH (aq., 4 mL) and Et$_2$O (20 mL) and the layers were separated. The aqueous phase was extracted with Et$_2$O (5 mL) and the combined organics were washed with water (2×5 mL) and dried over MgSO$_4$. After evaporation of the solvents, the crude product was purified by catch-and-release on a 5 g SCX cartridge, eluting with MeOH and then 25% 2 M NH$_3$/MeOH in DCM, to afford the crude amine. This was further purified by column chromatography (10 g Isolute II cartridge), eluting with 5%-10% 2 M NH$_3$/MeOH in DCM and finally by trituration with ether and petrol to give the title compound as a white powder (~1:1 mixture of stereoisomers) (93 mg, 36%). $^1$H NMR (300 MHz, DMSO-d$_6$): δ 0.80-1.80 (8H, m), 2.08 (0.5H, br s), 2.16 (3H, s), 2.30 (0.5H, br s), 2.90 (0.5H, br s), 3.03 (0.5H, br s), 4.84 (0.5H, br d, J=6 Hz), 7.21 (1H, t, J=8 Hz), 7.39 (1H, t, J=9 Hz), 7.64 (1H, q, J=7 Hz), 7.70 (2H, d, J=9 Hz) and 7.86 (2H, d, J=9 Hz). LCMS: (MH)$^+$=381.

Synthesis 59

N-(4-(Ethylamino)cyclohexyl)-2',4'-difluorobiphenyl-4-sulfonamide (ABD817)

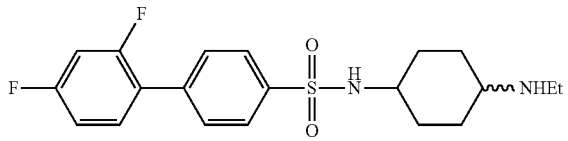

A solution of ABD786 (250 mg, 0.68 mmol) in dry THF (5 mL) was stirred under argon and ethylamine (2 M in THF, 1.35 mL) was added by syringe. The solution was stirred for 1 hour and then STAB (360 mg, 1.7 mmol) was added in one portion. The mixture was stirred at room temperature overnight. TLC indicated starting material to still be present, and so further ethylamine (2 M in THF, 1.35 mL) and STAB (360 mg, 1.7 mmol) and a drop of acetic acid were added and stirring was continued for a further 3 days. The reaction was quenched by the addition of 2 M NaOH (aq., 4 mL) and Et$_2$O (20 mL) and the layers were separated. The aqueous phase was extracted with Et$_2$O (5 mL) and the combined organics were washed with water (2×5 mL) and dried over MgSO$_4$. After evaporation of the solvents, the crude product was purified by catch-and-release on a 5 g SCX cartridge, eluting with MeOH and then 25% 2 M NH$_3$/MeOH in DCM, to afford the crude amine. This was further purified by column chromatography (10 g Isolute II cartridge), eluting with 5%-10% 2 M NH$_3$/MeOH in DCM and finally by trituration with ether and petrol to give the title compound as a white powder (~1:1 mixture of stereoisomers) (95 mg, 35%). $^1$H NMR (300 MHz, DMSO-d$_6$): δ 0.88-0.97 (3H, m), 1.08-1.63 (8H, m), 1.75 (1H, d, J=11 Hz), 2.19 (1H, br s), 2.42 (2H, q, J=7 Hz), 2.90 (0.5H, br s), 3.04 (0.5H, br s), 7.21 (1H, td, J=8 Hz, 2 Hz), 7.40 (1H, td, J=10 Hz, 2 Hz), 7.64 (1H, q, J=7 Hz), 7.70 (2H, d, J=9 Hz), 7.85 (1H, d, J=9 Hz) and 7.87 (1H, d, J=9 Hz). LCMS: (MH)$^+$=395.

Synthesis 60

2',4'-Difluoro-N-(4-(isopropylamino)cyclohexyl)biphenyl-4-sulfonamide (ABD818)

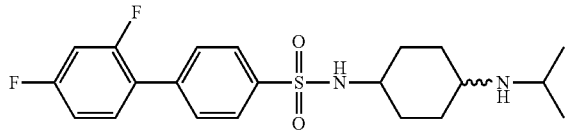 [SMILES: CC(C)NC1CCC(NS(=O)(=O)c2ccc(-c3ccc(F)cc3F)cc2)CC1]

ABD786 (450 mg, 1.23 mmol) was stirred in DCM (5 mL) and $^i$PrNH$_2$ (160 μL, 110 mg, 1.85 mmol) was added and the solution was stirred overnight at room temperature. It was then diluted with further DCM (5 mL) and STAB (1.30 g, 6.15 mmol) was added and stirring was continued for 2 hours. 2 M NaOH (aq., 7 mL) and EtOAc (30 mL) were added and the mixture was stirred for a further 30 minutes before the layers were separated. The aqueous phase was extracted with further EtOAc (10 mL) and the combined organics were washed with water (2×10 mL) and brine (10 mL) and dried over MgSO$_4$. After evaporation of the solvents the crude product was split into two portions and each was purified by catch and release chromatography on a 2 g SCX cartridge, eluting with MeOH and then 10% 2 M NH$_3$/MeOH in DCM, affording the desired material as a red-brown glassy solid. This was triturated with Et$_2$O at 0° C. to give the title compound as an off-white powdery solid (200 mg, 40%, highly enriched (7:1) in one isomer). The trituration solvents were evaporated and the residue was purified by chromatography on SiO$_2$ (10 g Isolute II cartridge), eluting with 10% 2 M NH$_3$/MeOH in DCM to afford a pale yellow glassy solid, trituration of which with ether and hexane afforded a second crop of the title compound as an off-white powdery solid (78 mg, 15%, 4:6 mixture of isomers). $^1$H NMR (second crop) (300 MHz, DMSO-d$_6$): δ 0.86 (3H, d, J=7.5 Hz), 0.90 (3H, d, J=7.5 Hz), 1.15 (1H, q, J=15 Hz), 1.28-1.41 (4H, m), 1.47-1.55 (1H, m), 1.66 (1H, d, J=13 Hz), 1.70 (1H, d, J=15 Hz), 2.25-2.33 (0.6H, m), 2.51-2.55 (0.4H, m), 2.74 (1H, octet, J=7.5 Hz), 2.89 (0.4H, br s), 3.05 (0.6H, br s), 7.21 (1H, td, J=11 Hz, 3 Hz), 7.40 (1H, ddd, J=14 Hz, 11 Hz, 3 Hz), 7.63 (1H, t, J=10 Hz), 7.70 (2H, d, J=9 Hz), 7.85 (1.2H, d, J=10 Hz) and 7.87 (0.8H, d, J=10 Hz). LCMS: (MH)$^+$=409.

Synthesis 61

N-(4-(Diethylamino)cyclohexyl)-2',4'-difluorobiphenyl-4-sulfonamide (ABD819)

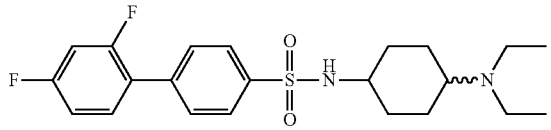 [SMILES: CCN(CC)C1CCC(NS(=O)(=O)c2ccc(-c3ccc(F)cc3F)cc2)CC1]

Prepared in an analogous fashion to ABD817, using diethylamine, to give the title compound as an off-white powder (~1:1 mixture of stereoisomers) (168 mg, 58%). $^1$H NMR (300 MHz, DMSO-$d_6$): δ 0.84-0.89 (6H, m), 1.05-1.75 (8H, m), 2.35 (4H, q, J=7 Hz), 2.90 (0.5H, br s), 3.20 (0.5H, br s), 7.21 (1H, td, J=8 Hz, 2 Hz), 7.41 (1H, ddd, J=12 Hz, 9 Hz, 3 Hz), 7.60-7.65 (1H, m), 7.71 (2H, d, J=9 Hz) and 7.84-7.89 (2H, m). LCMS: (MH)$^+$=423.

Synthesis 62

2',4'-Difluoro-N-(4-(pyrrolidin-1-yl)cyclohexyl)biphenyl-4-sulfonamide (ABD820)

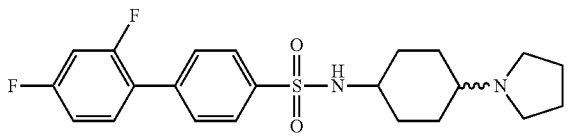 [SMILES: O=S(=O)(NC1CCC(N2CCCC2)CC1)c1ccc(-c2ccc(F)cc2F)cc1]

Prepared in an analogous fashion to ABD817, using pyrrolidine, to give the title compound as an off-white powder (~2:3 mixture of stereoisomers) (26 mg, 9%). $^1$H NMR (400 MHz, DMSO-$d_6$): δ 1.00-1.47 (6H, m), 1.60-1.65 (4H, m), 1.79-2.01 (3H, m), 2.48 (4H, br s), 2.93 (0.5H, br s), 3.07 (0.5H, br s), 7.21 (1H, td, J=8 Hz, 2 Hz), 7.40 (1H, ddd, J=12 Hz, 9 Hz, 3 Hz), 7.61-7.66 (1H, m), 7.70 (2H, d, J=9 Hz) and 7.84-7.89 (2H, m). LCMS: (MH)$^+$=421.

Synthesis 63

2',4'-Difluoro-N-(4-morpholinocyclohexyl)biphenyl-4-sulfonamide (ABD821)

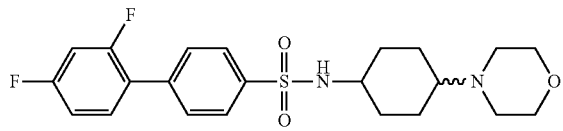 [SMILES: O=S(=O)(NC1CCC(N2CCOCC2)CC1)c1ccc(-c2ccc(F)cc2F)cc1]

Prepared in an analogous fashion to ABD817, using morpholine, to give the title compound as an off-white powder (~3:2 mixture of stereoisomers) (63 mg, 21%). $^1$H NMR (300 MHz, DMSO-$d_6$): δ 1.11 (2H, q, J=8 Hz), 1.25-1.42 (2H, m), 1.51-1.60 (2H, m), 1.67 (2H, d, J=9 Hz), 2.02 (1H, br s), 2.34-2.38 (4H, m), 2.90 (0.5H, br s), 3.15 (0.5H, br s), 3.45-3.52 (4H, m), 7.21 (1H, td, J=8 Hz, 2 Hz), 7.40 (1H, ddd, J=12 Hz, 9 Hz, 3 Hz), 7.64 (1H, q, J=8 Hz), 7.70 (2H, d, J=9 Hz), 7.86 (1H, d, J=8 Hz) and 7.87 (1H, d, J=8 Hz). LCMS: (MH)$^+$=437; (M−H)$^-$=435.

Synthesis 64

N-(4-(Ethyl(methyl)amino)cyclohexyl)-2',4'-difluorobiphenyl-4-sulfonamide (ABD822)

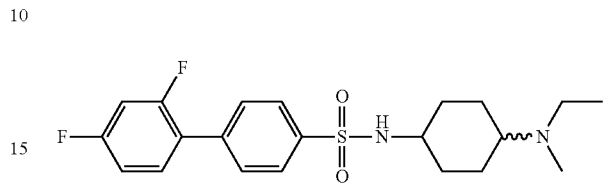

Prepared in an analogous fashion to ABD817, using N-ethylmethylamine, to give the title compound as an off-white powder (~7:3 mixture of stereoisomers) (73 mg, 26%). $^1$H NMR (400 MHz, DMSO-$d_6$): δ 0.88-0.91 (3H, m), 1.13-1.17 (2H, m), 1.29-1.36 (2H, m), 1.52-1.66 (4H, m), 2.06 (2H, s [Me of major isomer]), 2.13 (1H, s [Me of minor isomer]), 2.26 (1H, br s), 2.37 (2H, q, J=9 Hz), 2.89 (1H, br s), 3.18 (1H, br s), 7.21 (1H, t, J=10 Hz), 7.39 (1H, t, J=12 Hz), 7.63 (1H, q, J=8 Hz), 7.70 (2H, d, J=9 Hz) and 7.82-7.89 (2H, m). LCMS: (MH)$^+$=409.

Synthesis 65 cis-4-(2',4'-Difluorobiphenyl-4-ylsulfonamido)cyclohexanecarboxylic acid (ABD824b)

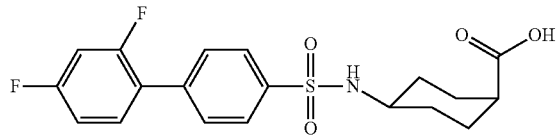 [SMILES: O=C(O)C1CCC(NS(=O)(=O)c2ccc(-c3ccc(F)cc3F)cc2)CC1]

A mixture of (ABD781a) (1.06 g, 2.6 mmol), MeOH (5 mL), THF (5 mL) and water (5 mL) was stirred at room temperature and LiOH.H$_2$O (550 mg, 13 mmol) was added. The mixture was stirred overnight before the MeOH and THF were removed under reduced pressure. The residue was diluted to 40 mL with water and acidified with 2 M HCl (aq.). The resulting suspension was stirred vigorously for 1 hour and the off-white solid was then collected by suction and air-dried to give the title compound (920 mg, 89%).

Synthesis 66 cis-4-(2',4'-Difluorobiphenyl-4-ylsulfonamido)-N-methylcyclohexane carboxamide (ABD824a)

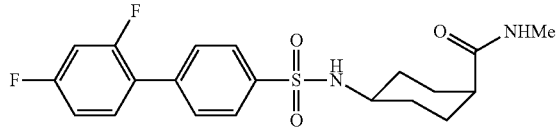 [SMILES: CNC(=O)C1CCC(NS(=O)(=O)c2ccc(-c3ccc(F)cc3F)cc2)CC1]

A suspension of ABD824b (920 mg, 2.33 mmol) in dry DCM (15 mL) was cooled under argon to 0° C. and (COCl)$_2$ (245 µL, 325 mg, 2.56 mmol) was added, followed by DMF (30 µL, catalytic). The ice bath was removed and the mixture was stirred at room temperature for 1.5 hours, giving a pale yellow solution. A solution of methylamine (2 M in THF, 5.8 mL, 11.6 mmol) in dry DCM (15 mL) was cooled under argon to 0° C. and the solution of the acid chloride was added by cannula, resulting in the formation of a precipitate. The mixture was stirred for 1 hour, allowing it to warm to room temperature, and then diluted with further DCM (30 mL) and washed with water (2×10 mL) and brine (10 mL). The organic solvents were dried over MgSO$_4$ and evaporated to give the title compound as a pale yellow solid (890 mg, 94%), which required no further purification. $^1$H NMR (300 MHz, CDCl$_3$): δ 1.48-1.78 (8H, m), 2.05-2.15 (1H, m), 2.78 (3H, d, J=5 Hz), 3.48-3.57 (1H, m), 4.97 (1H, br s), 5.49 (1H, br s), 6.87-7.05 (2H, m), 7.40 (1H, q, J=5 Hz), 7.64 (2H, d, J=9 Hz) and 7.94 (2H, d, J=9 Hz). LCMS: (MH)$^+$=409; (M−H)$^−$=407.

Synthesis 67

2',4'-Difluoro-N-(cis-4-((methylamino)methyl)cyclohexyl)biphenyl-4-sulfonamide (ABD824)

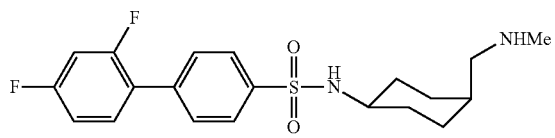 [SMILES: CNCC1CCC(NS(=O)(=O)c2ccc(-c3ccc(F)cc3F)cc2)CC1]

A solution of ABD824a (240 mg, 0.59 mmol) in dry THF (10 mL) was cooled to 0° C. under argon and BH$_3$ (1 M in THF, 1.8 mL, 1.8 mmol) was added by syringe. The solution was stirred overnight, allowing it to warm to room temperature, after which TLC indicated that starting material was still present, as well as a more polar compound. Further BH$_3$ (1 M in THF, 1.0 mL, 1.0 mmol) was added and the solution was heated at reflux for 3 hours. After cooling to room temperature, the reaction was quenched with NH$_4$Cl (sat. aq., 5 mL) and water was added to dissolve the solids. The mixture was extracted with Et$_2$O (3×15 mL) and the organics were dried over MgSO$_4$ and evaporated to afford the crude product as a colourless glass. This was purified by SCX catch-and-release chromatography, eluting with MeOH and then 10% 2 M NH$_3$/MeOH in DCM, and finally by trituration with Et$_2$O to give the title compound as a white powder (81 mg, 35%). $^1$H NMR (300 MHz, DMSO-d$_6$): δ 1.20-1.53 (8H, m), 2.22 (3H, s), 2.31 (2H, d, J=7 Hz), 3.17 (2H, br s), 7.21 (1H, td, J=11 Hz, 3 Hz), 7.40 (1H, ddd, J=14 Hz, 11 Hz, 3 Hz), 7.64 (1H, td, J=11 Hz, 8 Hz), 7.70 (2H, d, J=9 Hz) and 7.87 (2H, d, J=10 Hz). LCMS: (MH)$^+$=395.

Synthesis 68 cis-4-(2',4'-Difluorobiphenyl-4-ylsulfonamido)-N,N-dimethyl cyclohexanecarboxamide (ABD826a)

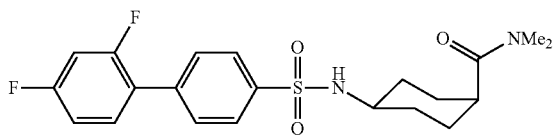 [SMILES: CN(C)C(=O)C1CCC(NS(=O)(=O)c2ccc(-c3ccc(F)cc3F)cc2)CC1]

A suspension of ABD824b (850 mg, 2.15 mmol) in dry DCM (15 mL) was cooled under argon to 0° C. and (COCl)$_2$ (225 µL, 300 mg, 2.4 mmol) was added, followed by DMF (30 µL, catalytic). The ice bath was removed and the mixture was stirred at room temperature for 1 hour, giving a pale yellow solution. Half of the solution of the acid chloride was cooled to 0° C. under argon and dimethylamine (2 M in THF, 2.5 mL, 5 mmol) was added by syringe. The mixture was stirred overnight, allowing it to warm to room temperature. It was then diluted with further DCM (20 mL) and washed with water (3×5 mL) and brine (5 mL). The organic solvents were dried over MgSO$_4$ and evaporated to afford the crude product as an off-white solid. This was purified by chromatography on SiO$_2$ (20 g Isolute II cartridge), eluting with 50% acetone/hexane, to give the title compound as a white solid (395 mg, 87%). $^1$H NMR (300 MHz, CDCl$_3$): δ 1.45-1.62 (4H, m), 1.65-1.82 (4H, m), 2.48-2.59 (1H, m), 2.99 (3H, s), 3.00 (3H, s), 3.55-3.63 (1H, m), 5.17 (1H, d, J=8 Hz), 6.87-7.03 (2H, m), 7.42 (1H, q, J=5 Hz), 7.61 (2H, d, J=9 Hz) and 7.95 (2H, d, J=9 Hz). LCMS: (MH)$^+$=423; (M−H)$^−$=421.

Synthesis 69

N-(cis-4-((Dimethylamino)methyl)cyclohexyl)-2',4'-difluorobiphenyl-4-sulfonamide (ABD826)

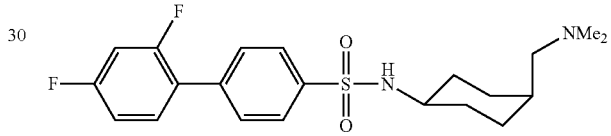

A solution of ABD826a (200 mg, 0.47 mmol) in dry THF (5 mL) was cooled under argon to 0° C. and LiAlH$_4$ (1 M in THF, 2.36 mL, 2.36 mmol) was added dropwise by syringe over 2 minutes. Once gas evolution ceased, the mixture was allowed to warm to room temperature and stirred for 1 hour. The solution was then cooled back to 0° C. and quenched with Na$_2$SO$_4$.10H$_2$O (s, ~500 mg) and allowed to stir overnight. The mixture was filtered, rinsing the solid well with additional THF. After evaporation of the solvents the crude product was purified by trituration with Et$_2$O/hexane, to give the title compound as a white powder (95 mg, 49%). $^1$H NMR (400 MHz, DMSO-d$_6$): δ 1.18-1.47 (8H, m), 1.97 (2H, d, J=9 Hz), 2.03 (6H, s), 3.18 (2H, br s), 4.34 (1H, br s), 7.21 (1H, t, J=9 Hz), 7.39 (1H, t, J=11 Hz), 7.58-7.67 (2H, m), 7.70 (2H, d, J=10 Hz) and 7.87 (2H, d, J=10 Hz). LCMS: (MH)$^+$=409.

Synthesis 70

4-(N-(trans-4-Hydroxycyclohexyl)sulfamoyl)phenylboronic acid (ABD836a)

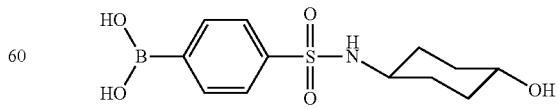

ABD598 (500 mg, 1.5 mmol), bis(pinacolato)diboron (420 mg, 1.65 mmol), KOAc (294 mg, 3 mmol) and Pd(dppf)Cl$_2$ (55 mg, 0.08 mmol) were combined in DMSO (10 mL) and placed in an ultrasonic bath under a stream of argon for 5 minutes. The flask was then placed in an oil bath at 90° C. and stirred for 1 hour. The reaction mixture was then cooled to room temperature and poured into water (40 mL) and extracted with EtOAc (3×20 mL). The combined organics were washed with water (20 mL) and brine (10 mL), dried (Na$_2$SO$_4$) and filtered. Evaporation gave a brown solid (555 mg), containing both the boronic acid and the ester, which was used without further purification.

Synthesis 71

4-(3,5-Dichloropyridin-2-yl)-N-(trans-4-hydroxycyclohexyl)benzene sulfonamide (ABD836)

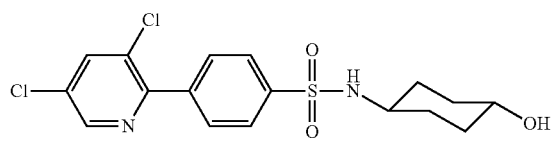 [SMILES: O=S(=O)(NC1CCC(O)CC1)c1ccc(-c2ncc(Cl)cc2Cl)cc1]

ABD836a (278 mg, 0.92 mmol) was dissolved in DME (4 mL) and 2-bromo-3,5-dichloropyridine (171 mg, 0.76 mmol), Pd(dppf)Cl$_2$ (23 mg, 5 mol %) and Na$_2$CO$_3$ (2 M soln, 1.15 mL, 2.30 mmol) were added. The mixture was placed in an ultrasonic bath under a stream of argon for 5 minutes. It was then placed in a preheated oil bath (90° C.) for 1.75 hours. After this time, the reaction mixture was cooled to room temperature and poured into water (80 mL) and extracted with EtOAc (3×60 mL). The combined organics were washed with water (50 mL) and brine (50 mL), dried (Na$_2$SO$_4$), filtered and evaporated onto silica. The crude material was purified by flash column chromatography on SiO$_2$, eluting with 2:1 EtOAc/hexane. Evaporation of the desired fractions and re-crystallisation (DCM-hexane) gave the title compound as colourless needles (21 mg, 7%). $^1$H NMR (300 MHz, CDCl$_3$): δ 1.20-1.34 (4H, m), 1.38 (1H, d, J=4 Hz), 1.91 (4H, d, J=8 Hz), 3.18 (1H, br s), 3.56 (1H, br s), 4.46 (1H, d, J=7.5 Hz), 7.85 (2H, d, J=8 Hz), 7.97 (3H, s overlapped with d, J=8 Hz) and 8.58 (1H, d, J=2 Hz). LCMS: (MH)$^+$=401.

Synthesis 72

4-(5-Chloropyrimidin-2-yl)-N-(trans-4-hydroxycyclohexyl)benzenesulfonamide (ABD837)

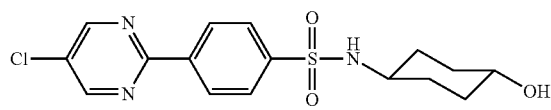 [SMILES: O=S(=O)(NC1CCC(O)CC1)c1ccc(-c2ncc(Cl)cn2)cc1]

A solution ABD836a (278 mg, 0.92 mmol) in DME (4 mL) was stirred and 2,5-dichloropyrimidine (112 mg, 0.76 mmol), Pd(dppf)Cl$_2$ (23 mg, 5 mol %) and Na$_2$CO$_3$ (2 M soln, 1.15 mL, 2.30 mmol) were added. The mixture was placed in an ultrasonic bath under a stream of argon for 5 minutes. It was then placed in a preheated oil bath (90° C.) for 1 hour. After this time, the reaction mixture was cooled to room temperature and poured into water (80 mL) and extracted with EtOAc (3×60 mL). The combined organics were washed with water (50 mL), brine (50 mL), dried (Na$_2$SO$_4$), filtered and absorbed onto silica. The crude material was purified by flash column chromatography, eluting with 1:1 v/v acetone-hexane. Evaporation of the desired fractions and washing the solid with diethyl ether gave the title compound (55 mg, 20%) as an off-white solid. $^1$H NMR (300 MHz, DMSO-d$_6$): δ 1.08 (4H, septet, J=11 Hz), 1.55 (2H, d, J=11 Hz), 1.66 (2H, d, J=11 Hz), 2.90 (1H, t, J=9 Hz), 3.20-3.28 (1H, br m), 4.45 (1H, br s), 7.74 (1H, br s), 7.93 (2H, d, J=8 Hz), 8.48 (2H, d, J=8 Hz) and 9.04 (2H, s). LCMS: (MH)$^+$=368.

Synthesis 73

N-(trans-4-Hydroxycyclohexyl)-4-(pyrimidin-5-yl)benzenesulfonamide (ABD861)

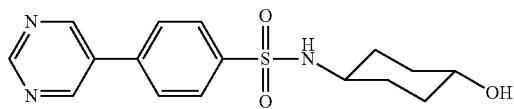

A solution of ABD836a (225 mg, 0.78 mmol) in DME (4 mL) was stirred at room temperature and 5-bromopyrimidine (99 mg, 0.63 mmol), Pd(dppf)Cl$_2$ (23 mg, 0.03 mmol) and Na$_2$CO$_3$ (2 M aq., 0.95 mL) were added. The mixture was placed in an ultrasonic bath under a stream of argon for 5 minutes and then in an oil bath that had been pre-heated to 90° C. The reaction mixture was heated for 1 hour and then cooled to room temperature, diluted with water (20 mL) and extracted with EtOAc (3×10 mL). The extracts were washed with water (5 mL) and brine (5 mL) and dried over MgSO$_4$. After evaporation of the solvents the residue was purified by column chromatography on SiO$_2$ (50% acetone/hexane) to afford a mixture of the desired material and a dimeric species produced during boronic acid formation. The partially purified material was triturated with Et$_2$O (2×2 mL) and then purified by a second SiO$_2$ column, this time eluting with 5%-10% 2 M NH$_3$/MeOH in DCM, to give the title compound as an off-white solid (65 mg, 31%). $^1$H NMR (300 MHz, DMSO-d$_6$): δ 1.10 (4H, septet, J=7 Hz), 1.55-1.73 (4H, m), 2.85-2.95 (1H, m), 3.20-3.30 (1H, m), 4.47 (1H, d, J=3 Hz), 7.73 (1H, d, J=6 Hz), 7.90 (2H, d, J=8.5 Hz), 8.01 (2H, d, J=8.5 Hz), 9.19 (2H, s) and 9.21 (1H, s). LCMS: (MH)$^+$=334.

Synthesis 74

N-(4-(2',4'-Difluorobiphenyl-4-ylsulfonamido)cyclohexyl)-2,2,2-trifluoroacetamide (ABD864a)

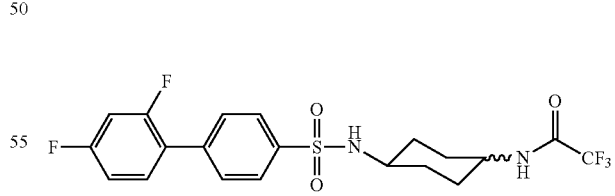

A solution of ABD787 (410 mg, 1.12 mmol) in dry THF (10 ml) was stirred at room temperature and triethylamine (350 μL, 250 mg, 2.5 mmol) and TFAA (200 μL, 300 mg, 1.44 mmol) were added, causing the solution to turn deep red and get warm. The mixture was stirred at room temperature for 3 hours and then poured into water (10 mL) and EtOAc (20 mL) and the layers were separated. The organic phase was washed with water (10 mL) and sat. NaHCO$_3$ (aq., 10 mL) and dried over MgSO$_4$. After evaporation of the solvents, the crude

Synthesis 75

2',4'-Difluoro-N-(cis-4-(2,2,2-trifluoroethylamino)cyclohexyl)biphenyl-4-sulfonamide (ABD864)

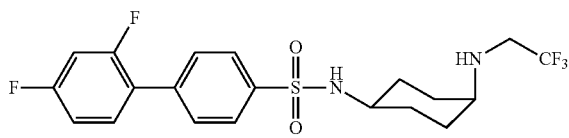 [SMILES: O=S(=O)(NC1CCC(NCC(F)(F)F)CC1)c1ccc(-c2ccc(F)cc2F)cc1]

A solution of N-(4-(2',4'-difluorobiphenyl-4-ylsulfonamido)cyclohexyl)-2,2,2-trifluoroacetamide (350 mg, 0.76 mmol) in THF (20 mL) was stirred under argon at room temperature and BH$_3$/THF (1 M, 3.8 mL) was added. The mixture was heated to 50° C. and stirred for 4 hours, after which LCMS analysis indicated the reaction to be proceeding, but significant starting material was present. Further BH$_3$/THF (1 M, 2.5 mL) was added and the mixture was heated at 50° C. overnight. The mixture was then cooled and NH$_4$Cl (sat. aq., 10 mL) was added cautiously, followed by water to dissolve all the solids. The mixture was then extracted with EtOAc (3×20 mL) and the combined extracts were dried over MgSO$_4$. After evaporation of the solvents, the crude material was purified by column chromatography on SiO$_2$ (30% acetone/hexane) affording a viscous pale yellow oil (270 mg, 79%), which LCMS indicated to be only 78% pure and a mixture of diastereomers.

The mixture of diastereomers was dissolved in HPLC grade MeOH (5 mL) and purified by reverse-phase preparative HPLC, eluting with 50%-80% acetonitrile/water containing 0.1% NH$_4$OH (aq.), to give baseline separation of the two peaks. The fractions corresponding to the first peak were combined and the acetonitrile was removed under reduced pressure. The residue was extracted with DCM (30 mL, 2×15 mL) and the combined extracts were dried over MgSO$_4$. Evaporation of the solvents gave the title cis-isomer as a pale yellow solid (66 mg, 24%). $^1$H NMR (300 MHz, CDCl$_3$): δ 1.07-1.30 (5H, m), 1.86-1.95 (4H, m), 2.46-2.54 (1H, m), 3.17 (2H, q, J=9.5 Hz), 3.22-3.11 (1H, m), 4.49 (1H, d, J=7.5 Hz), 6.91-7.03 (2H, m), 7.43 (1H, td, J=8.5 Hz, 6 Hz), 7.64 (2H, dd, J=8.5 Hz, 1.5 Hz) and 7.93 (2H, d, J=8.5 Hz). LCMS: (MH)$^+$=449.

Synthesis 76

2',4'-Difluoro-N-(trans-4-(2,2,2-trifluoroethylamino)cyclohexyl)biphenyl-4-sulfonamide (ABD865)

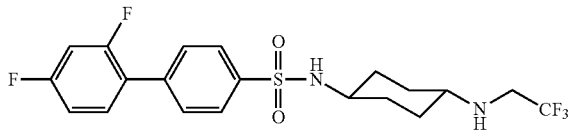 [SMILES: O=S(=O)(NC1CCC(NCC(F)(F)F)CC1)c1ccc(-c2ccc(F)cc2F)cc1]

Continuing from the separation as described for ABD864: the fractions corresponding to the second peak were combined and the acetonitrile was removed under reduced pressure, the residue was extracted with DCM (30 mL, 2×15 mL) and the combined extracts were dried over MgSO$_4$. Evaporation of the solvents gave the title trans-isomer as a pale yellow solid (48 mg, 24%). $^1$H NMR (300 MHz, CDCl$_3$): δ 1.39-1.71 (8H, m), 2.68 (1H, br s), 3.13 (2H, q, J=9.5 Hz), 3.38 (1H, br s), 4.92 (1H, d, J=7 Hz), 6.90-7.04 (2H, m), 7.43 (1H, td, J=8.5 Hz, 6.5 Hz), 7.63 (2H, dd, J=8.5 Hz, 2 Hz) and 7.95 (2H, d, J=8.5 Hz). LCMS: (MH)$^+$=449.

Synthesis 77 tert-Butyl-4-hydroxycyclohexylcarbamate

trans-4-Aminocyclohexanol hydrochloride (13.5 g) was suspended in dry DCM (100 mL) and cooled to 5-10° C. To this, BOC anhydride (24.6 mL, 23.32 g, 106.8 mmol) was added drop-wise over 15 minutes. The reaction mixture was stirred under nitrogen for 15 minutes. Triethylamine (37.2 mL) was added and the mixture was stirred overnight, allowing the temperature to rise to room temperature. The solution was diluted with water (100 mL) and extracted with DCM (2×50 mL), organic layer dried over Na$_2$SO$_4$. Evaporation of the solvents gave the title compound as a colorless solid (17.1 g, quantitative).

Synthesis 78 tert-Butyl 4-oxocyclohexylcarbamate

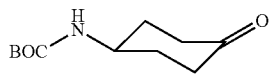 [SMILES: CC(C)(C)OC(=O)NC1CCC(=O)CC1]

tert-Butyl-4-hydroxycyclohexylcarbamate (17 g) and Celite (17 g) were suspended in dry DCM (100 mL). PCC (25.5 g) was added portion-wise within 10-15 minutes. The reaction was stirred under nitrogen for 2.5 hours. The solvent was removed under reduced pressure and the residue was re-dissolved in EtOAc/n-hexane (1000 mL) and filtered through celite. The organic layer was dried over Na$_2$SO$_4$. Evaporation of the solvents gave the title compound as a colorless solid (16.1 g, quantitative).

Synthesis 79 tert-Butyl cis-4-hydroxy-4-methylcyclohexylcarbamate and tert-butyl trans-4-hydroxy-4-methylcyclohexylcarbamate

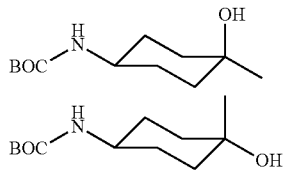

A solution of methylmagnesium chloride (3 M in THF, 71.4 mL) was added to a solution of tert-butyl 4-oxocyclohexylcarbamate (16 g, 75.01 mmol) in THF at −75° C. The mixture was stirred overnight, allowing the temperature to rise to room temperature. The reaction mixture was quenched with saturated ammonium chloride solution and the volatile solvent removed under reduced pressure. The residue was taken up in water (50 mL) and DCM (100 mL) and solid citric acid were added until the layers separated. The organic phase was washed with brine and dried (Na$_2$SO$_4$). Evaporation of the solvents gave a crude sticky mass which was purified by column chromatography and the trans isomer isolated as a colourless solid (660 mg) and the cis isomer as a colourless solid (1.0 g).

Synthesis 80 trans-4-Amino-1-methyl-cyclohexanol and cis-4-amino-1-methyl-cyclohexanol

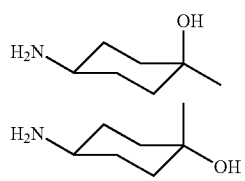

To the Boc-protected amines from Synthesis 79 was added ethanolic HCl (20 mL) at 0° C. The solution was allowed to warm to room temperature and stirred for 2 hours. The reaction mixture was concentrated to give the trans isomer as a light yellow oil (400 mg) and the cis isomer (800 mg) as a light yellow oil.

Synthesis 81

4-Bromo-N-(cis-4-hydroxy-4-methylcyclohexyl)benzenesulfonamide (ABD899a)

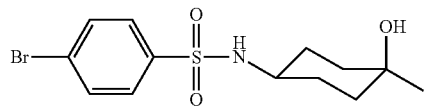 [SMILES: CC1(O)CCC(NS(=O)(=O)c2ccc(Br)cc2)CC1]

A suspension of cis-4-amino-1-methyl cyclohexanol (0.6 g) and 4-bromobenzenesulfonyl chloride (1.78 g) in chloroform (20 mL) was stirred under nitrogen at 0° C. Triethylamine (3.2 mL) was added and the mixture was stirred for 16 hours, allowing the temperature to rise to room temperature. The solution was diluted with EtOAc (50 mL) and washed with water (2×20 mL), 1 M HCl (20 mL) and brine (20 mL) and dried over Na$_2$SO$_4$. Evaporation of the solvents gave a light yellow solid, which was triturated with n-pentane and ether to give the title compound as a white solid (1.2 g, 75%).

Synthesis 82

2',4'-Difluoro-N-(cis-4-hydroxy-4-methylcyclohexyl)biphenyl-4-sulfonamide (ABD899)

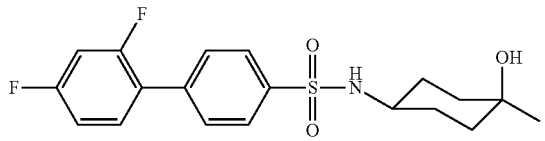 [SMILES: CC1(O)CCC(NS(=O)(=O)c2ccc(-c3ccc(F)cc3F)cc2)CC1]

Using a method analogous to Method B, with ABD899a and 2',4'-difluorophenylboronic acid, the title compound was obtained as a clear oil. Trituration with n-pentane and ether gave a white solid. $^1$H NMR (300 MHz, CDCl$_3$): δ 1.23 (1H, s), 1.25 (3H, s), 1.44-1.51 (4H, m), 1.65 (2H, m), 1.85 (2H, m), 3.35 (1H, m), 4.59 (1H, d, J=6.6 Hz), 6.91-7.03 (2H, m), 7.44 (1H, m), 7.63 (2H, dd, J=8.5 Hz, 2 Hz) and 7.94 (2H, dd, J=8.7 Hz). MS, m/z: Calcd, 381.12. Found, 380.4 (M).

Synthesis 83

2',4'-Difluoro-N-(trans-4-hydroxy-4-methylcyclohexyl)biphenyl-4-sulfonamide (ABD9001

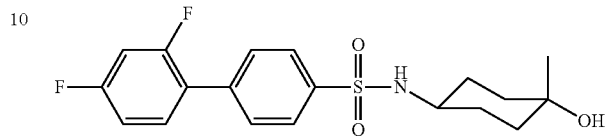

A suspension of trans-4-amino-1-methyl-cyclohexanol (0.3 g) and 2',4'-difluorobiphenylsulfonyl chloride (0.8 g) in chloroform (20 mL) were stirred under nitrogen at 0° C. Triethylamine (1.60 mL) was added and the mixture was stirred for 16 hours, allowing the temperature to rise to room temperature. The solution was diluted with EtOAc (50 mL) and washed with water (2×20 mL), 1 M HCl (20 mL) and brine (20 mL) and dried over Na$_2$SO$_4$. Evaporation of the solvents gave a dark brown solid which was purified by column chromatography followed by trituration with n-pentane and ether to give the title compound as a buff sticky solid (80 mg, 10% yield). Melting point: 105°-107° C. MS, m/z: Calcd, 381.12. Found, 380.5 (M). $^1$H NMR (300 MHz, CDCl$_3$): δ 0.98 (1H, s), 1.20 (3H, s), 1.40 (2H, m), 1.60 (5H, m), 3.18 (1H, m), 4.38 (1H, d, J=7.8 Hz), 6.91-7.03 (2H, m), 7.44 (1H, m), 7.63 (2H, dd, J=8.5 Hz, 2 Hz) and 7.94 (2H, dd, J=8.7 Hz). MS, m/z: Calcd, 381.12. Found, 380.5 (M).

Biological Methods

Initial screening of candidate compounds was performed using in vitro assays to determine potency, metabolic stability and solubility in biologically relevant fluids. Potency was assessed using a viability assay based on the survival of the J774 macrophage cell line. Macrophages are closely related to osteoclasts and have been used previously as a model system for osteoclast survival (see, e.g., Luckman et al., 1998). Like osteoclasts, J774 macrophages are dependent on continued NFκB activation for survival, thereby providing a valuable screen for compounds with anti-inflammatory activity. Metabolic stability was measured by determining the rate of disappearance of compound in the presence of human liver microsomal preparations, as quantified by LC-MS/MS. Solubility was measured by equilibration of the compound in fasted state simulated intestinal fluid (FaSSIF) and quantified by HPLC.

Alamar Blue Macrophage J774 Viability Assay

In vitro potency as anti-inflammatory agents was determined for a number of APSAC compounds by incubation with J774 macrophages and subsequent determination of cell viability.

J774 cells were plated at $10^4$ cells per well in 100 μL αMEM (α Modified Eagle Medium) in 96-well plates and grown overnight. The next day, test compounds were added to the cultures, and cultures were continued for another 72 hours. At the end of the culture period, cell survival was determined using an Alamar Blue assay as previously described (see, e.g., Nociari et al., 1998).

Alamar Blue is an oxidation-reduction sensitive indicator. The dye itself is in the oxidised state, which is blue and non-fluorescent. The dye can accept electrons from reducing species, such as NADPH and FADH, to form a reduced dye species, which is red and fluorescent. Thus the transformation from oxidised form to reduced form can be measured by fluorimetric or colourimetric means. For fluorescence measurements, 530-560 nm excitation and 590 nm emission wavelengths are typically used. For colourimetric measurements, absorbance at 570 nm (reduced form) and 600 nm (oxidised form) is typically measured. A simple calculation is performed to determine the relative quantities of the two species.

A high ratio of the reducing species, NADPH and FADH, to the corresponding oxidised species, NADP and FAD, is an indicator that cells are proliferating and viable. A low ratio indicates cells that are quiescent or non-viable.

Briefly, Alamar Blue (Biosource International) was added undiluted to the each well (1:10 v/v, 10 µL). The plate was incubated at 37° C. for 3-4 hours and the fluorescence was measured at 590 nm, with a 25 nm bandwidth. A high reading indicated cells with normal viability, and a low reading indicated cells that have been damaged and are no longer proliferating normally. The controls gave a high fluorescence reading, indicating a high number of live, healthy cells. A potent test compound gave a low fluorescence reading. The average results for each test compound (n=5) were expressed as a percent (%) of the average control value.

Addition of Compounds.

All of the compounds studied were made up as 100 mM solutions in DMSO. These stock solutions were then diluted 1000-10000× in culture medium (αMEM). From these 100 µM or 10 µM solutions, convenient quantities (3-33 µL) were added directly to the wells so as to give the desired final compound concentration.

This assay offers numerous advantages over other assays, including MTT assays: it permits a higher throughput; it is more sensitive; it is non-damaging to the cells; it is faster; and it generally gives an identical result to MTT assays.

Aqueous Solubility Measurements

Thermodynamic aqueous solubility was measured by equilibration of a number of APSAC compounds, in the solid state, with fasted state simulated intestinal fluid (FaSSIF) and quantified by HPLC. Measurement of solubility in FaSSIF provides a valuable model for the prediction of drug dissolution following oral administration.

FaSSIF was prepared as described below:
Preparation of blank FaSSIF:

NaOH pellets (174 mg), $NaH_2PO_4 \cdot 2H_2O$ (2.235 g), and NaCl (3.093 g) were dissolved in 500 mL of water. The pH was adjusted to 6.5 using 1 M NaOH solution.

Preparation of FaSSIF:

Sodium taurocholate (165 mg) was dissolved in 25 mL blank FaSSIF. 0.6 mL of a solution containing 100 mg/mL lecithin in methylene chloride was added. The methylene chloride was eliminated under vacuum at about 40° C. The vacuum was drawn for 15 minutes at 250 mbar, followed by 15 minutes at 100 mbar. This resulted in a clear, micellar solution, having no perceptible odour of methylene chloride. After cooling to room temperature, the solution was then adjusted to 100 mL with blank FaSSIF.

Aqueous solubility was determined by suspending separately sufficient compound in FaSSIF to give a maximum final concentration of 10 mg/mL of the parent free-form of the compound. The suspension was equilibrated at 25° C. for 24 hours, and then the pH was measured. The suspension was then filtered through a glass fibre C filter into a 96-well plate. The filtrate was then diluted by a factor of 100. Quantification was made by HPLC with reference to a standard solution of compound at approximately 0.1 mg/mL in DMSO. Different volumes of the standard, diluted and undiluted sample solutions were injected. The solubility was calculated using the peak areas determined by integration of the peak found at the same retention time as the principal peak in the standard injection. Detection conditions are shown in the table below. Analysis was performed on an Agilent HP1100 series system equipped with a diode array detector and using ChemStation software vB.02.01-SR1.

TABLE 1

HPLC Method Parameters for Solubility Measurements

| Type of method: | Reverse phase with gradient elution |
| --- | --- |
| Column: | Phenomenex Luna, C18 (2) 5 µm 50 × 4.6 mm |
| Column Temperature (° C.): | 25 |
| Standard Injections (µL): | 1, 2, 3, 5, 7, 10 |
| Test Injections (µL): | 1, 2, 3, 10, 20, 50 |
| Detection: Wavelength, Bandwidth (nm): | 260, 80 |
| Flow Rate (mL/min): | 2 |
| Phase A: | 0.1% TFA in water |
| Phase B: | 0.085% TFA in acetonitrile |

| Timetable: | Time (min) | % Phase A | % Phase B |
| --- | --- | --- | --- |
| | 0.0 | 95 | 5 |
| | 1.0 | 80 | 20 |
| | 2.3 | 5 | 95 |
| | 3.3 | 5 | 95 |
| | 3.5 | 95 | 5 |
| | 4.4 | 95 | 5 |

Human Liver Microsomal Stability Assay

Metabolic stability of APSAC derivatives was measured by determination of the rate of compound disappearance when incubated in the presence of human liver microsomes. Liver microsomes are prepared from the endoplasmic reticulum of hepatocytes and are the primary source of the most important enzymes (cytochrome P450) involved in drug metabolism. Study of drug stability in the presence of liver microsomes is accepted as a valuable model permitting rapid prediction of in vivo drug stability.

Protocol Summary:

Human liver microsomes were obtained from a commercial source. Test compounds (3 µM) were incubated with pooled liver microsomes (male and female). Samples were incubated for a 45 minute period and removed at 5 time points and test compounds were analysed by LC-MS/MS.

Microsomes (final protein concentration 0.5 mg/mL), 0.1 M phosphate buffer pH 7.4, and test compound (final concentration 3 µM; diluted from 10 mM stock solution to give a final DMSO concentration of 0.25%) were incubated at 37° C. prior to the addition of NADPH (final concentration 1 mM) to initiate the reaction. The final incubation volume was 25 µL. A control incubation was included for each compound tested, where 0.1 M phosphate buffer pH 7.4 was added instead of NADPH. The control compounds testosterone and 7-hydroxycoumarin were included in each experiment and all incubations were performed singularly for each compound.

Each compound was incubated for 0, 5, 15, 30, and 45 minutes. The control (minus NADPH) was incubated for 45 minutes only. The reactions were stopped by the addition of 50 µL methanol containing internal standard at the appropriate time points. The incubation plates were centrifuged at 2500 rpm for 20 minutes at 4° C. to precipitate the protein.

Quantitative Analysis:

Following protein precipitation, the sample supernatants were combined in cassettes of up to 4 compounds and analysed using standard LC-MS/MS conditions.

Data Analysis:

From a plot of the natural logarithm of the peak area ratio (i.e., the ratio of compound peak area:internal standard peak area) against time, the gradient of the line was determined. Subsequently, half-life and intrinsic clearance were calculated using the equations below:

Eliminated rate constant $(k)=(-\text{gradient})$.

Half life $(t_{1/2})(\text{min})=0.063/k$.

Intrinsic Clearance $(CL_{int})(\mu L/\text{min/million cells})=(V \times 0.693)/t_{1/2}$.

wherein V=Incubation volume (µL/mg microsomal protein).

Pharmacokinetics Studies

Absorption and metabolic stability were studied using an in vivo pharmacokinetics assay. Drug levels were assessed using ultra-performance LC/TOF-MS.

Three male Sprague-Dawley rats, 200-300 g, were dosed per route. Test compound was administered either orally or intravenously (dose level of 1 mg/kg body weight). Test compound was formulated in 50:50 tetraethylene glycol:PBS for both routes. Animals were given free access to food throughout the study. On the day prior to dosing, the carotid artery was cannulated for sample collection and for the intravenous study the jugular vein was cannulated to enable dosing.

Blood samples were taken from the carotid artery at the following time points and placed in heparinised tubes:
Oral dosing—predose, 0.25, 0.5, 1, 2, 4, 8 and 24 hours post dose.
IV dosing—predose, 0.08, 0.25, 0.5, 1, 2, 4 and 8 hours post dose.

After the final time point, the animals were sacrificed by an overdose of anaesthetic.

Blood samples were centrifuged to obtain plasma, which was transferred to a separate container and frozen at −20° C.

Sample Preparation:

Samples were thawed at room temperature and prepared by protein precipitation with acetonitrile in the ratio 1:2 with plasma, followed by centrifugation for 10 minutes at 16,100×g (Eppendorf 5415D, Eppendorf AG, Hamburg, Germany). The supernatants were collected for analysis. The standard samples were prepared similarly, after spiking blank rat plasma samples to study compound concentrations at 1, 2, 5, 10, 20, 50, 100, 200, 500 and 1000 ng/mL. In addition, extra samples were prepared from 0-1 hour i.v. samples by diluting 1/20 with 50% aqueous acetonitrile to avoid exceeding the linear range of the analytical method.

Analytical Methods:

A Waters Acquity liquid ultra-performance chromatographic system (Waters Corp., Milford, Mass., USA) with autosampler, vacuum degasser and column oven was used. The analytical column used for all compounds was a Waters BEH C18, (2.1×50 mm, 1.7 µm, Waters Corp, Milford, Mass., USA) together with a 0.2 µm on-line filter before the column. The eluents were 0.1% acetic acid (A, pH 3.2) and methanol (B). Gradient elution from 5% to 60% B in two minutes was employed, followed by one minute gradient to 90% B and column equilibration. The flow rate was 0.5 mL/min and the column oven temperature was 35° C. The flow was directed to the MS via Water Acquity photo-diode-array (PDA) detector. LC/TOF-MS data were recorded with a Micromass LCT Premier XE time-of-flight (TOF) mass spectrometer (Micromass Ltd., Manchester, England) equipped with a LockSpray electrospray ionization source. A positive ionization mode of electrospray was used for all compounds. The mass range of m/z 100-900 was acquired. The W-option of the reflector was used, and the DRE (dynamic range enhancement) option was set to on. The mass spectrometer and HPLC system were operated under Micromass MassLynx 4.1 software. Leucine enkephalin ($[M+H]^+$ m/z 556.2771) was used as a lock mass compound for accurate mass measurements and was delivered into the LockSpray probe with a syringe pump. MassLynx 4.1 software was used for controlling the instrumentation and for data processing.

Calculations:

The pharmacokinetic parameters for the test compounds were calculated by WinNonlin Pro (Pharsight Corp, CA) using standard noncompartmental methods. The elimination phase half-life ($t_{1/2}$) was calculated by least-squares regression analysis of the terminal linear part of the log concentration–time curve. The area under the plasma concentration–time curve (AUC) was determined by use of the linear trapezoidal rule up to the last measurable concentration and thereafter by extrapolation of the terminal elimination phase to infinity. The tentative oral bioavailability (F) was calculated by dividing the AUC (0-24 hours) after p.o. administration by the AUC (0-8 hours) after i.v. administration, i.e., F=AUC(p.o.)/AUC(i.v), and reported as percentages (%).

Caspase Induction Study

The ability to activate caspase 3 was studied using a fluorogenic enzyme substrate assay.

Briefly, human primary monocytes were isolated from whole blood using Ficoll gradients. The resulting cells were plated into microwell plates for 24 hours after which non-adherent cells were removed by washing. Cells were differentiated in the presence of 100 ng/mL MCSF. Cells were pre-treated with 10 µM test compound for 1 hour prior to stimulation with 10 ng/mL TNF α. Caspase 3 activation as an indicator of apoptosis was detected using the Nucview488 stain, which was added one hour prior to visualisation. The Nucview488 stain indicates the activation of caspase 3 (CPP32, apopain, YAMA), a cysteine peptidase which plays a key role in the induction of apoptosis in individual whole mammalian cells. Essentially, Nucview488 consists of a fluorogenic DNA dye and a DEVD substrate moiety specific for caspase 3. In itself, Nucview488 is nonfluorescent. However, upon entering the cell cytoplasm, Nucview488 is cleaved by caspase 3 to form a high-affinity DNA dye. The released DNA dye migrates to the cell nucleus to stain the nucleus bright green. This fluorescent staining produced in response to caspase 3 activity is monitored using fluorescent light microscopy.

Biological Data

Biological Study 1

The biological activity of a number of APSAC compounds was determined and compared with the biological activity of a range of structurally related compounds using the assays described previously.

$IC_{50}$ values were determined for several APSAC compounds, as well as several reference compounds, using the Alamar Blue macrophage J774 viability assay described above. The results are summarised in the following tables.

TABLE 2A

Alamar Blue Macrophage J774 Viability Assay Data (Reference Compounds)

| Compound | —R^X2 | —R^X4 | —Q^Ref | IC$_{50}$ (μM) |
|---|---|---|---|---|
| ABD455 | —Cl | —Cl | 3-(hydroxymethyl)phenyl | 0.50 |
| ABD456 | —F | —F | 3-(hydroxymethyl)phenyl | 0.25 |
| ABD466 | —F | —F | 4-(hydroxymethyl)phenyl | 3.0 |
| ABD575 | —F | —Cl | 3-(hydroxymethyl)phenyl | 0.40 |

TABLE 2B

Alamar Blue Macrophage J774 Viability Assay Data

| Compound | —R^X2 | —R^X4 | —DQ | IC$_{50}$ (μM) |
|---|---|---|---|---|
| ABD599 | —F | —F | trans-4-hydroxycyclohexyl | 0.07 |
| ABD777 | —F | —F | cis-4-hydroxycyclohexyl | 1.9 |
| ABD769 | —F | —F | (hydroxymethyl)cyclopentyl | 4.59 |
| ABD770 | —F | —F | (hydroxymethyl)cyclopentyl | — |
| ABD771 | —F | —F | (hydroxymethyl)cyclopentyl | — |
| ABD772 | —F | —F | (hydroxymethyl)cyclopentyl | — |
| ABD773 | —F | —F | (hydroxymethyl)cyclopentyl | 0.13 |
| ABD774 | —F | —F | (hydroxymethyl)cyclopentyl | — |
| ABD775 | —F | —F | (hydroxymethyl)cyclopentyl | — |
| ABD796 | —F | —F | (2-hydroxypropan-2-yl)cyclopentyl | <0.3 |
| ABD813 | —F | —F | (hydroxymethyl)cyclopentyl | 0.57 |
| ABD815 | —F | —F | (2-hydroxypropan-2-yl)cyclopentyl | <0.3 |
| ABD776 | —F | —F | trans-4-(hydroxymethyl)cyclohexyl | 0.8 |

TABLE 2B-continued

Alamar Blue Macrophage J774 Viability Assay Data

| Compound | —$R^{X2}$ | —$R^{X4}$ | —DQ | $IC_{50}$ (μM) |
|---|---|---|---|---|
| ABD781 | —F | —F | cyclohexyl-CH2OH | 0.3 |
| ABD786 | —F | —F | cyclohexanone | 0.28 |
| ABD787 | —F | —F | cyclohexyl-NH2 | 3.55 |
| ABD794 | —F | —F | cyclohexyl-C(Me)2OH | 2.1 |
| ABD795 | —F | —F | cyclohexyl-C(Me)2OH | 2.7 |
| ABD798 | —F | —F | cyclohexyl-NMe2 | 0.6 |
| ABD799 | —F | —F | cyclohexyl-NMe2 | 0.4 |
| ABD812 | —F | —F | cyclohexyl-NH2 | 7.6 |
| ABD816 | —F | —F | cyclohexyl-NHMe | 0.8 |
| ABD817 | —F | —F | cyclohexyl-NHEt | <1 |
| ABD819 | —F | —F | cyclohexyl-NEt2 | 2.4 |
| ABD820 | —F | —F | cyclohexyl-pyrrolidine | 2.5 |
| ABD821 | —F | —F | cyclohexyl-morpholine | >10 |
| ABD822 | —F | —F | cyclohexyl-N(Me)Et | 6.98 |
| ABD824 | —F | —F | cyclohexyl-CH2NMe2 | 7.2 |
| ABD826 | —F | —F | cyclohexyl-CH2NHMe | 1.0 |
| ABD864 | —F | —F | cyclohexyl-NH-CH2CF3 | >10 |
| ABD865 | —F | —F | cyclohexyl-NH-CH2CF3 | 5.9 |

TABLE 2C

Alamar Blue Macrophage J774 Viability Assay Data

| Compound | —Ar | $IC_{50}$ (μM) |
|---|---|---|
| ABD599 | 2,4-difluorobiphenyl | 0.07 |
| ABD655 | 2-F, 4-Cl biphenyl | 0.18 |

TABLE 2C-continued

Alamar Blue Macrophage J774 Viability Assay Data

Ar—S(=O)(=O)—NH—[trans-4-hydroxycyclohexyl]

| Compound | —Ar | IC$_{50}$ (μM) |
|---|---|---|
| ABD665 | 4'-(trifluoromethoxy)-2-fluoro-biphenyl-4-yl | 4.9 |
| ABD705 | 2',4'-difluoro-3-chloro-biphenyl-4-yl | 0.83 |
| ABD710 | 4'-methoxy-2-fluoro-biphenyl-4-yl | 1.98 |
| ABD712 | 3'-trifluoromethyl-4'-chloro-biphenyl-4-yl | 5.46 |
| ABD732 | 4'-cyano-3-chloro-biphenyl-4-yl | 4.32 |
| ABD735 | 2',4'-difluoro-2-methyl-biphenyl-4-yl | 0.09 |
| ABD742 | 4'-(trifluoromethoxy)-2-methyl-biphenyl-4-yl | 0.77 |
| ABD756 | 2',4'-dichloro-3-(trifluoromethoxy)-biphenyl-4-yl | 2.18 |
| ABD836 | 5,6-dichloro-pyridin-2-yl-phenyl | 0.28 |
| ABD837 | 5-chloro-pyrimidin-2-yl-phenyl | 8.88 |
| ABD861 | pyrimidin-5-yl-phenyl | Inactive |

These data demonstrate that it is possible to replace the phenylene group of -Q$^{Ref}$ with a saturated carbocyclic structure without a loss of potency. These data also demonstrate that it is possible to make a range of substitutions on the biaryl system and retain potency. The data also demonstrate that these replacements and substitutions are neither trivial nor predictable and can lead either to an increase or a decrease in potency.

Biological Study 2

The metabolic stability of a number of APSAC compounds was determined and compared with the metabolic stability of a range of structurally related compounds using the assays described previously.

Biological half-life values ($t_{1/2}$) were determined for several APSAC compounds, as well as several reference compounds, using the human liver microsomal stability assay described above. The results are summarised in the following tables.

TABLE 3A

Human Liver Microsomal Stability Data
(Reference Compounds)

R$^{X4}$–(phenyl with R$^{X2}$)–phenyl–S(=O)(=O)—NH—Q$^{Ref}$

| Compound | —R$^{X2}$ | —R$^{X4}$ | —Q$^{Ref}$ | T$_{1/2}$ (min) |
|---|---|---|---|---|
| ABD455 | —Cl | —Cl | 3-(hydroxymethyl)phenyl | 28 |
| ABD456 | —F | —F | 3-(hydroxymethyl)phenyl | 30 |

TABLE 3A-continued

Human Liver Microsomal Stability Data
(Reference Compounds)

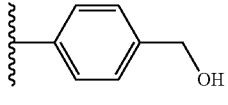 [SMILES: *c1ccc(CO)cc1]

| Compound | —R$^{X2}$ | —R$^{X4}$ | —Q$^{Ref}$ | T$_{1/2}$ (min) |
|---|---|---|---|---|
| ABD466 | —F | —F | 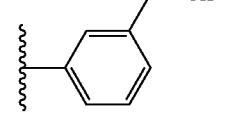 | 2 |
| ABD575 | —F | —Cl | 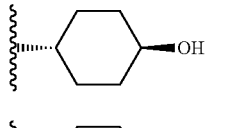 | 42 |

TABLE 3B

Human Liver Microsomal Stability Data

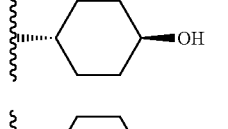

| Compound | —R$^{X2}$ | —R$^{X4}$ | —DQ | T$_{1/2}$ (min) |
|---|---|---|---|---|
| ABD599 | —F | —F | 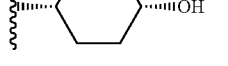 | 287 |
| ABD655 | —F | —Cl | 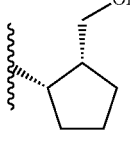 | 228 |
| ABD777 | —F | —F | 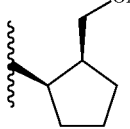 | 69 |
| ABD769 | —F | —F | 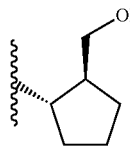 | 42 |
| ABD770 | —F | —F | 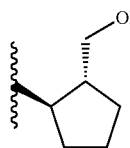 | — |

TABLE 3B-continued

Human Liver Microsomal Stability Data

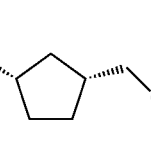

| Compound | —R$^{X2}$ | —R$^{X4}$ | —DQ | T$_{1/2}$ (min) |
|---|---|---|---|---|
| ABD771 | —F | —F | 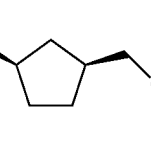 | — |
| ABD772 | —F | —F | 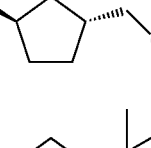 | — |
| ABD773 | —F | —F | 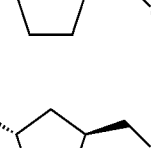 | 54 |
| ABD774 | —F | —F | 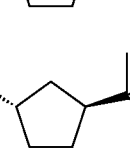 | — |
| ABD775 | —F | —F | 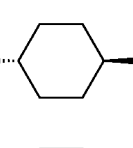 | — |
| ABD796 | —F | —F | 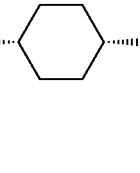 | 54 |
| ABD813 | —F | —F |  | 45.4 |
| ABD815 | —F | —F | | 13.2 |
| ABD776 | —F | —F | | 137 |
| ABD781 | —F | —F | | 41 |

TABLE 3B-continued

Human Liver Microsomal Stability Data

| Compound | —R$^{X2}$ | —R$^{X4}$ | —DQ | T$_{1/2}$ (min) |
|---|---|---|---|---|
| ABD786 | —F | —F | cyclohexyl-=O | 12 |
| ABD787 | —F | —F | cyclohexyl-NH$_2$ | Stable |
| ABD794 | —F | —F | cyclohexyl-C(CH$_3$)$_2$OH | Stable |
| ABD795 | —F | —F | cyclohexyl-C(CH$_3$)$_2$OH | 15 |
| ABD798 | —F | —F | cyclohexyl-NMe$_2$ | Stable |
| ABD799 | —F | —F | cyclohexyl-NMe$_2$ | Stable |
| ABD812 | —F | —F | cyclohexyl-NH$_2$ | 585 |

These data demonstrate that it is possible to replace the phenylene group of -Q$^{Ref}$ with a saturated carbocyclic structure without a loss of metabolic stability. The data also demonstrate that this replacement is neither trivial nor predictable and can lead either to an increase or a decrease in metabolic stability.

Biological Study 3

The solubility of a number of APSAC compounds was determined and compared with the solubility of a range of structurally related compounds using the assays described previously.

Solubility in the biological model fasted state simulated intestinal fluid (FaSSIF) was determined for several APSAC compounds, as well as several reference compounds, using the aqueous solubility assay described above. The results are summarised in the following tables.

TABLE 4A

Aqueous Solubility Data (Reference Compounds)

| Compound | R$^{X2}$ | R$^{X4}$ | Q$^{Ref}$ | Solubility (mg/mL) |
|---|---|---|---|---|
| ABD455 | Cl | Cl | phenyl-CH$_2$OH (meta) | 0.02 |
| ABD456 | F | F | phenyl-CH$_2$OH (meta) | 0.04 |
| ABD466 | F | F | phenyl-CH$_2$OH (para) | 0.04 |
| ABD575 | F | Cl | phenyl-CH$_2$OH (meta) | 0.07 |

TABLE 4B

Aqueous Solubility Data

| Compound | —R$^{X2}$ | —R$^{X4}$ | DQ | Solubility (mg/mL) |
|---|---|---|---|---|
| ABD599 | —F | —F | cyclohexyl-OH | 0.03 |
| ABD655 | —F | —Cl | cyclohexyl-OH | 0.03 |
| ABD777 | —F | —F | cyclohexyl-OH | 0.06 |

TABLE 4B-continued

Aqueous Solubility Data

Structure: $R^{X4}$ and $R^{X2}$ substituted biphenyl with -SO$_2$-NH-DQ group

| Compound | —R$^{X2}$ | —R$^{X4}$ | DQ | Solubility (mg/mL) |
|---|---|---|---|---|
| ABD769 | —F | —F | cis-2-(hydroxymethyl)cyclopentyl | 0.07 |
| ABD770 | —F | —F | cyclopentyl with CH$_2$OH | — |
| ABD771 | —F | —F | cyclopentyl with CH$_2$OH | — |
| ABD772 | —F | —F | cyclopentyl with CH$_2$OH | — |
| ABD773 | —F | —F | 3-(CH$_2$OH)-cyclopent-1-yl | 0.89 |
| ABD774 | —F | —F | cyclopentyl with CH$_2$OH | — |
| ABD775 | —F | —F | cyclopentyl with CH$_2$OH | — |
| ABD796 | —F | —F | cyclopentyl with C(CH$_3$)$_2$OH | 0.20 |
| ABD813 | —F | —F | cyclopentyl with CH$_2$OH | 0.33 |
| ABD815 | —F | —F | cyclopentyl with C(CH$_3$)$_2$OH | 0.25 |
| ABD776 | —F | —F | cyclohexyl with CH$_2$OH | 0.082 |
| ABD781 | —F | —F | 4-(CH$_2$OH)-cyclohex-1-yl | 0.59 |
| ABD786 | —F | —F | 4-oxocyclohexyl | 0.032 |
| ABD787 | —F | —F | 4-aminocyclohexyl | 0.14 |
| ABD794 | —F | —F | cyclohexyl with C(CH$_3$)$_2$OH | 0.012 |
| ABD795 | —F | —F | cyclohexyl with C(CH$_3$)$_2$OH | 0.05 |
| ABD798 | —F | —F | 4-(NMe$_2$)-cyclohexyl | 4.7 |
| ABD799 | —F | —F | 4-(NMe$_2$)-cyclohexyl | 7.2 |
| ABD812 | —F | —F | 4-aminocyclohexyl | 0.98 |

These data demonstrate that it is possible to achieve a substantial increase in solubility by replacing the phenylene group of -Q$^{Ref}$ with a saturated carbocyclic structure. The data also demonstrate that this replacement is neither trivial nor predictable and can lead either to an increase or a decrease in metabolic stability. Furthermore, the data show the exceptional aqueous solubility imparted by the groups 3-(CH$_2$OH)-cyclopent-1-yl (e.g., as found in ABD773), 4-(CH$_2$OH)-cyclohex-1-yl (e.g., as found in ABD781) and 4-(NMe$_2$)-cyclohexan-1-yl (e.g., as found in ABD798 and ABD799).

Biological Study 4

The oral absorption of the APSAC compounds, ABD773 and ABD781, was determined in a rat model as described previously.

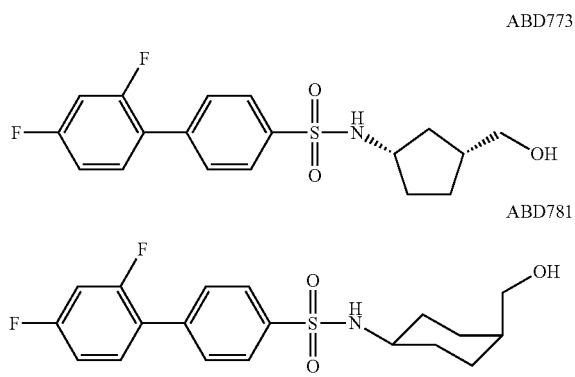

ABD773

ABD781

Plasma levels of ABD773 or ABD781, following oral or intravenous dosage (1 mg/kg) (see FIGS. 1 and 2 and FIGS. 3 and 4 respectively), were investigated in vivo in rats using an ultra-performance LC/TOF-MS detection system, as described previously. The pharmacokinetic data are summarised in the following table.

TABLE 4

Pharmacokinetic data

|  | ABD773 (1 mg/kg) | | ABD781 (1 mg/kg) | | Reference Compound ABD455 (2.5 mg/kg) | |
|---|---|---|---|---|---|---|
| Bioavailability F % | | | | | | |
|  | 13 | | 43 | | 3 | |
|  | p.o. | i.v. | p.o. | i.v. | p.o. | i.v. |
| AUC (ng/mL/min) | 1500 | 11900 | 9600 | 22400 | 1.2 | 9 |
| T½ (h) | 3.17 | 0.81 | 3.28 | 0.87 | 0.8 | 0.53 |

Figure 5:
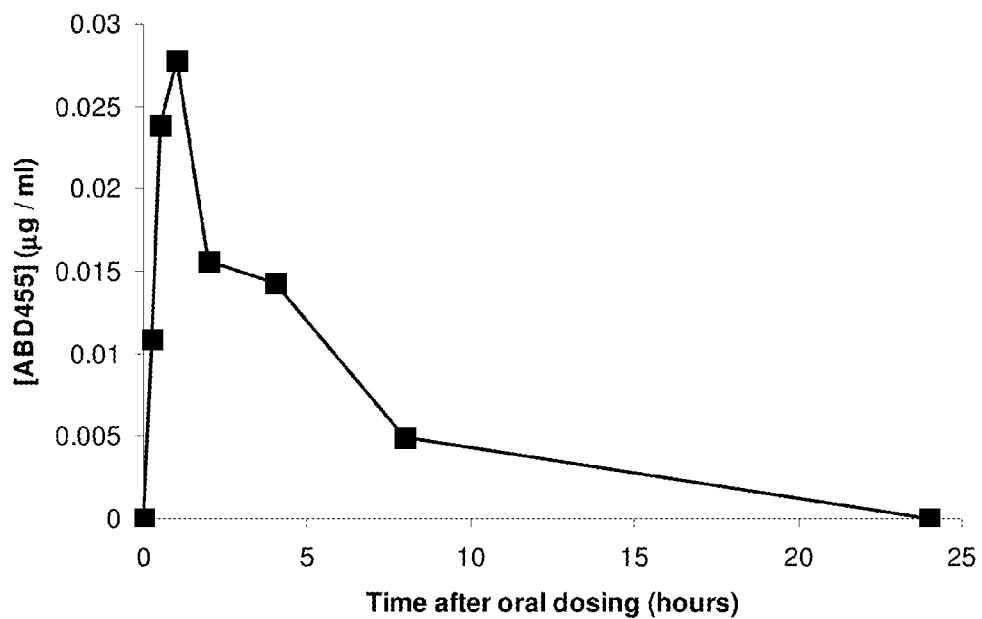
FIG. 5 is a graph showing mean plasma concentration (μg/mL) of the reference compound ABD455 (■) after oral administration (2.5 mg/kg) to a rat model.
Figure 6:
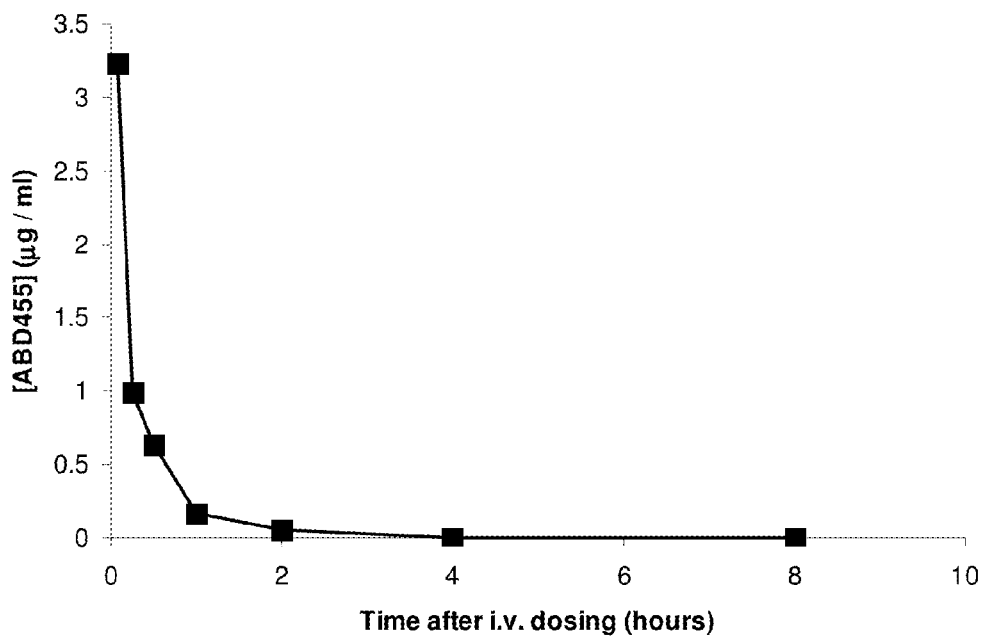
FIG. 6 is a graph showing mean plasma concentration (μg/mL) of the reference compound ABD455 (■) after intravenous administration (2.5 mg/kg) to a rat model.

The data show improved absorbance of the APSAC compound, ABD773, above that of the reference compound ABD455 (see FIGS. 5 and 6; Table 4) with a bioavailability (F) of 13% and an extended half life of 3.17 hours. The APSAC compound, ABD781, is especially well absorbed following oral administration with a bioavailability (F) of 43% and an extended half life of 3.28 hours and is superior to the reference compound ABD455. The data demonstrate that the APSAC compound ABD781 shows the properties required for an orally active drug.

Biological Study 5

The ability of APSAC compounds to activate caspase 3 in the presence of TNFα was determined using the fluorogenic enzyme substrate assay described previously.

Figure 7:
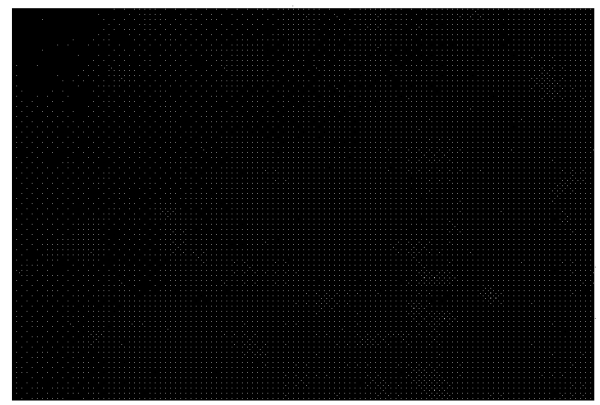
FIG. 7 is a series of images of human monocytes monitored using fluorescent light microscopy and showing the effects of ABD599 and ABD781 on caspase 3 activation in the presence of TNF α: (a) TNFα alone; (b) TNFα with 10 μM ABD599, and (c) TNFα with 10 μM ABD781.
Figure 7:
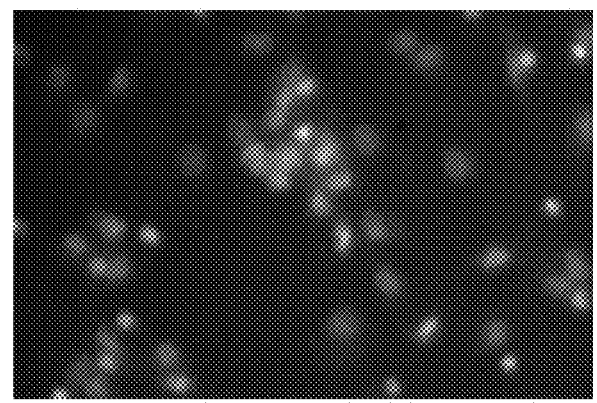
Figure 7:
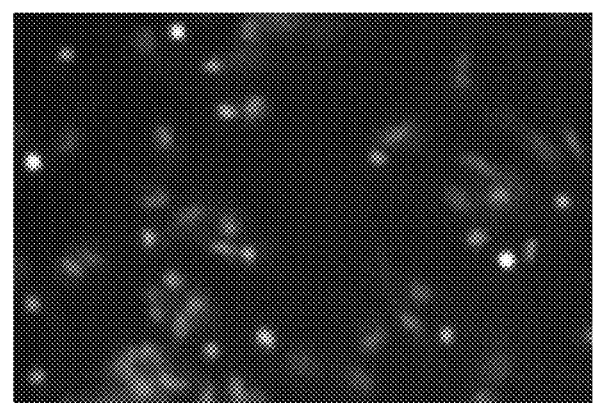

FIG. 7 shows a series of images of human monocytes monitored using fluorescent light microscopy and showing the effects of ABD599 and ABD781 on caspase 3 activation in the presence of TNF α: (a) TNFα alone; (b) TNFα with 10 μM ABD599, and (c) TNFα with 10 μM ABD781, by the use of a dye which fluoresces only on activation by caspase 3.

These data show that in the presence of TNFα alone no fluorescence is detected (the image is plain black with no light emission from the cells, as would be shown by white spots). This indicates that there is little activation of caspase 3 and that the cells do not undergo active apoptosis upon treatment with TNFα alone. Upon the addition of either ABD599 or ABD781, fluorescence is detected in the cell population, as demonstrated by the images showing a black background with multiple light emitting cells which appear as white dots. These data indicate that there has been significant activation of caspase 3 and that the cells are undergoing active apoptosis.

These data demonstrates that the APSAC compounds are able to activate caspase 3, and thus induce apoptosis, and therefore may be useful in the treatment of tumours associated with inactivation or impairment of caspase induction or with aberrant caspase signalling.

The foregoing has described the principles, preferred embodiments, and modes of operation of the present invention. However, the invention should not be construed as limited to the particular embodiments discussed. Instead, the above-described embodiments should be regarded as illustrative rather than restrictive, and it should be appreciated that variations may be made in those embodiments by workers skilled in the art without departing from the scope of the present invention.

REFERENCES

A number of patents and publications are cited herein in order to more fully describe and disclose the invention and the state of the art to which the invention pertains. Full citations for these references are provided below. Each of these references is incorporated herein by reference in its entirety into the present disclosure, to the same extent as if each individual reference was specifically and individually indicated to be incorporated by reference.

Baud et al., 1999, "Signaling by proinflammatory cytokines: oligomerization of TRAF2 and TRAF6 is sufficient for JNK and IKK activation and target gene induction via an amino-terminal effector domain", *Genes Dev.*, Vol. 13, pp. 1297-1308.

Baud et al., 2009, "Is NFκB a good target for cancer therapy? Hopes and pitfalls", *Nat. Rev. Drug Disc.*, Vol. 8, pp. 33-40.

Brennan et al., 1989, "Inhibitory effect of TNF alpha antibodies on synovial cell interleukin-1 production in rheumatoid arthritis", *Lancet*, Vol. 2, pp. 244-247.

Brennan et al., 1992, "Enhanced expression of tumor necrosis factor receptor mRNA and protein in mononuclear cells isolated from rheumatoid arthritis synovial joints", *Eur. J. Immunol.*, Vol. 22, pp. 1907-1912.

Brennan et al., 1996, "Cytokines in autoimmunity", *Curr. Opin. Immunol.*, Vol. 8, pp. 872-877.

Elliott et al., 1994, "Randomised double-blind comparison of chimeric monoclonal antibody to tumour necrosis factor alpha (cA2) versus placebo in rheumatoid arthritis", *Lancet*, Vol. 344, pp. 1105-1110.

Feldmann et al., 1994, "TNF alpha as a therapeutic target in rheumatoid arthritis," *Circ. Shock*, Vol. 43, pp. 179-184.

Feldmann et al., 1996, "Rheumatoid arthritis", *Cell*, Vol. 85, pp. 307-310.

Feldmann et al., 2001, "The role of TNF alpha and IL-1 in rheumatoid arthritis," *Curr. Dir. Autoimmun.*, Vol. 3, pp. 188-199.

Firestein et al., 1999, "Signal transduction and transcription factors in rheumatic disease", *Arthritis Rheum.*, Vol. 42, pp. 609-621.

Firestein, 1996, "Invasive fibroblast-like synoviocytes in rheumatoid arthritis. Passive responders or transformed aggressors?", *Arthritis Rheum.*, Vol. 39, pp. 1781-1790.

Firestein, 2005 "Immunologic mechanisms in the pathogenesis of rheumatoid arthritis", *J. Clin. Rheumatol.*, Vol. 11. pp. S39-S44.

Gottlieb, 2005, "Psoriasis: Emerging Therapeutic Strategies", *Nat. Rev. Drug Disc.*, Vol. 4, pp. 19-34.

Greig et al., 2004, "Alkyl aryl sulfonamides as therapeutic agents for the treatment of bone conditions". Published international application publication number WO 2005/118528.

Greig et al., 2006, "Development and characterization of biphenylsulfonamides as novel inhibitors of bone resorption", *J. Med. Chem.*, Vol 49: pp 7487-7492.

Greig et al., 2008, "Biphenyl-4-yl-sulfonic acid arylamides and Their Use as Therapeutic Agents", International patent publication number WO 2008/114022 (application number PCT/GB2008/000989) published 25 Sep. 2008.

Jin et al., 2004, "CCR8 Antagonists", International patent publication number WO 2004/073619 A2 published 2 Sep. 2004

Jimi et al., 2004, "Selective inhibition of NF-kappa B blocks osteoclastogenesis and prevents inflammatory bone destruction in vivo", *Nat. Med.*, Vol. 10, pp. 617-624.

Joosten et al., 1996, "Anticytokine treatment of established type II collagen-induced arthritis in DBA/1 mice. A comparative study using anti-TNF alpha, anti-IL-1 alpha/beta, and IL-1 Ra," *Arthritis Rheum.*, Vol. 39, pp. 797-809.

Klareskog et al., 2006, "A long-term, open-label trial of the safety and efficacy of etanercept (Enbrel) in patients with rheumatoid arthritis not treated with other disease-modifying antirheumatic drugs", *Ann. Rheum. Dis.*, Vol. 65, pp. 1578-1584.

Klareskog et al., 2006, "Mechanisms of disease: Genetic susceptibility and environmental triggers in the development of rheumatoid arthritis," Nat. Clin. Pract. Rheumatol., Vol. 2, pp. 425-433.

Korzenik et al., 2006, "Evolving knowledge and therapy of inflammatory bowel disease," *Nat. Rev. Drug Disc.*, Vol. 5, pp. 197-209.

Li et al., 2008, "A tumor necrosis factor-[alpha]-mediated pathway promoting autosomal dominant polycystic kidney disease", *Nature Medicine*, Vol. 14(8), pp. 863-868.

Liu, 2005, "Molecular mechanism of TNF signaling and beyond," *Cell Res.*, Vol. 15, pp. 24-27.

Luckman et al. 1998, "Heterocycle-containing bisphosphonates cause apoptosis and inhibit bone resorption by preventing protein prenylation: evidence from structure-activity relationships in J774 macrophages," *J. Bone Miner. Res.*, Vol. 13, pp. 1668-1678.

Mantovani, 2009, "Inflaming metastasis", *Nature*, Vol. 457, pp. 36-37.

McInnes et al., 2005, "Targeting cytokines beyond tumor necrosis factor-alpha and interleukin-1 in rheumatoid arthritis", *Curr. Pain Headache Rep.*, Vol. 9, pp. 405-411.

Mount et al., 2005, "Rheumatoid arthritis market", *Nat. Rev. Drug Disc.*, Vol. 2, pp. 11-12.

Nociari et al., 1998, "A Novel one-step, highly sensitive fluorimetric assay to evaluate cell-mediated cytotoxicity", *Journal of Immunological Methods*, Vol. 213, pp. 157-167.

O'Brien et al., 2000, "Structure-activity relationships and pharmacokinetic analysis for a series of potent, systemically available biphenylsulfonamide matrix metalloproteinase inhibitors". *J. Med. Chem. Vol* 43: pp 156-166.

Philchenkov et al., 2004, "Caspases and cancer: mechanisms of inactivation and new treatment modalities", *Exp. Oncol.*, Vol 26, pp 82-97.

Roodman, 2006, "Regulation of osteoclast differentiation", *Ann. N. Y. Acad. Sci.*, Vol. 1068, pp. 100-109.

Smolen et al., 2003, "Therapeutic Strategies for Rheumatoid Arthritis", *Nat. Rev. Drug Disc.*, Vol. 2, pp. 473-488.

Tanaka et al., 2003, Signal transduction pathways regulating osteoclast differentiation and function," *J. Bone Miner. Metab.*, Vol. 21, pp. 123-133.

van den Berg et al., 1999, "Pathogenesis of joint damage in rheumatoid arthritis: evidence of a dominant role for interleukin-I", *Baillieres Best Pract. Res. Clin. Rheumatol.*, Vol. 13, pp. 577-597.

van den Berg, 2002, "Is there a rationale for combined TNF and IL-1 blocking in arthritis?", *Clin. Exp. Rheumatol.*, Vol. 20, pp. S21-S25.

Weissmann, 2006, "The pathogenesis of rheumatoid arthritis," *Bull. Hosp. Jt. Dis.*, Vol. 64, pp. 12-15.

Ziff, 1990, "Rheumatoid arthritis—it's present and future", *J. Rheumatol.*, Vol. 17, pp. 127-133.

The invention claimed is:

1. A method of treatment of rheumatoid arthritis in a patient in need of said treatment comprising administering to said patient a therapeutically effective amount of a compound selected from compounds of the following formula, and pharmaceutically acceptable salts thereof:

wherein:
either: =W— is —CH= and —Y= is —CH=;
or: =W— is —CH= and —Y= is —N=;
—$R^{X2}$ is —$R^{X2S}$;
—$R^{X4}$ is —$R^{X4S}$;
—$R^{X2S}$ is independently —F, —Cl, or —$CF_3$;
—$R^{X4S}$ is independently —F, —Cl, or —$CF_3$;
—$R^{XC1}$ is independently —H or —$R^{XCC}$;
—$R^{XC2}$ is independently —H;
—$R^{XCC}$ is independently —F, —Cl, or —$R^{XCCC}$;
—$R^{XCCC}$ is independently -Me or -Et;
—$R^{SN}$ is —H;
-DQ is -$D^1$-$Q^1$;
either: -$D^1$ is cyclohexane-1,4-di-yl;
or: -$D^1$- is 4-methyl-cyclohexane-1,4-di-yl; and
-$Q^1$ is —OH.

2. A method according to claim 1, wherein =W— is —CH= and —Y= is —CH=.

3. A method according to claim 1, wherein =W— is —CH= and —Y= is —N=.

4. A method according to claim 2, wherein -$D^1$ is cyclohexane-1,4-di-yl.

5. A method according to claim 3, wherein -$D^1$ is cyclohexane-1,4-di-yl.

6. A method according to claim 2, wherein -$D^1$ is 4-methyl-cyclohexane-1,4-di-yl.

7. A method according to claim 3, wherein -$D^1$ is 4-methyl-cyclohexane-1,4-di-yl.

8. A method according to claim 4, wherein —$R^{X2S}$ is —F; and —$R^{X4S}$ is —F.

9. A method according to claim 5, wherein —$R^{X2S}$ is —F; and —$R^{X4S}$ is —F.

10. A method according to claim 6, wherein —$R^{X2S}$ is —F; and —$R^{X4S}$ is —F.

11. A method according to claim 7, wherein —$R^{X2S}$ is —F; and —$R^{X4S}$ is —F.

12. A method according to claim 4, wherein —$R^{X2S}$ is —Cl; and —$R^{X4S}$ is —Cl.

13. A method according to claim 5, wherein —$R^{X2S}$ is —Cl; and —$R^{X4S}$ is —Cl.

14. A method according to claim 6, wherein —$R^{X2S}$ is —Cl; and —$R^{X4S}$ is —Cl.

15. A method according to claim 7, wherein —$R^{X2S}$ is —Cl; and —$R^{X4S}$ is —Cl.

16. A method according to claim 8, wherein —$R^{XC1}$ is —H.

17. A method according to claim 9, wherein —$R^{XC1}$ is —H.

18. A method according to claim 10, wherein —$R^{XC1}$ is —H.

19. A method according to claim 11, wherein —$R^{XC1}$ is —H.

20. A method according to claim 12, wherein —$R^{XC1}$ is —H.

21. A method according to claim 13, wherein —$R^{XC1}$ is —H.

22. A method according to claim 14, wherein —$R^{XC1}$ is —H.

23. A method according to claim 15, wherein —$R^{XC1}$ is —H.

24. A method according to claim 8, wherein —$R^{XC1}$ is —$R^{XCC}$; and —$R^{XCC}$ is —F.

25. A method according to claim 9, wherein —$R^{XC1}$ is —$R^{XCC}$; and —$R^{XCC}$ is —F.

26. A method according to claim 10, wherein —$R^{XC1}$ is —$R^{XCC}$; and —$R^{XCC}$ is —F.

27. A method according to claim 11, wherein —$R^{XC1}$ is —$R^{XCC}$; and —$R^{XCC}$ is —F.

28. A method according to claim 12, wherein —$R^{XC1}$ is —$R^{XCC}$; and —$R^{XCC}$ is —F.

29. A method according to claim 13, wherein —$R^{XC1}$ is —$R^{XCC}$; and —$R^{XCC}$ is —F.

30. A method according to claim 14, wherein —$R^{XC1}$ is —$R^{XCC}$; and —$R^{XCC}$ is —F.

31. A method according to claim 15, wherein —$R^{XC1}$ is —$R^{XCC}$; and —$R^{XCC}$ is —F.

32. A method according to claim 8, wherein —$R^{XCC}$ is —$R^{XCCC}$; and —$R^{XCCC}$ is -Me.

33. A method according to claim 9, wherein —$R^{XCC}$ is —$R^{XCCC}$; and —$R^{XCCC}$ is -Me.

34. A method according to claim 10, wherein —$R^{XCC}$ is —$R^{XCCC}$; and —$R^{XCCC}$ is -Me.

35. A method according to claim 11, wherein —$R^{XCC}$ is —$R^{XCCC}$; and —$R^{XCCC}$ is -Me.

36. A method according to claim 12, wherein —$R^{XCC}$ is —$R^{XCCC}$; and —$R^{XCCC}$ is -Me.

37. A method according to claim 12, wherein —$R^{XCC}$ is —$R^{XCCC}$; and —$R^{XCCC}$ is -Me.

38. A method according to claim 14, wherein —$R^{XCC}$ is —$R^{XCCC}$; and —$R^{XCCC}$ is -Me.

39. A method according to claim 15, wherein —$R^{XCC}$ is —$R^{XCCC}$; and —$R^{XCCC}$ is -Me.

40. A method of treatment of rheumatoid arthritis in a patient in need of said treatment comprising administering to said patient a therapeutically effective amount of a compound selected from compounds of the following formula, and pharmaceutically acceptable salts thereof:

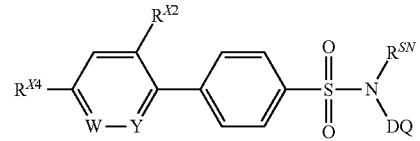

wherein:
either: =W— is —CH= and —Y= is —CH=;
or: =W— is —CH= and —Y= is —N=;
—$R^{X2}$ is —$R^{X2S}$;
—$R^{X4}$ is —$R^{X4S}$;
—$R^{X2S}$ is —$R^{X}$;
—$R^{X4S}$ is —$R^{X}$;
each —$R^{X}$ is independently —F, —Cl, —Br, —I, —$R^{XX}$, —OH, —$OR^{XX}$, —$SR^{XX}$, —$CF_3$, —$OCF_3$, —$SCF_3$, —C(=O)$R^{XX}$, —CN, or —$NO_2$;
each —$R^{XX}$ is saturated aliphatic $C_{1-4}$alkyl;
—$R^{SN}$ is —H;
-DQ is -$D^1$-$Q^1$;
either: -$D^1$ is cyclohexane-1,4-di-yl;
or: -$D^1$- is 4-methyl-cyclohexane-1,4-di-yl; and
-$Q^1$ is —OH.

41. A method according to claim 40, wherein =W— is —CH= and —Y= is —CH=.

42. A method according to claim 40, wherein =W— is —CH= and —Y= is —N=.

43. A method according to claim 41, wherein -$D^1$ is cyclohexane-1,4-di-yl.

44. A method according to claim 42, wherein -$D^1$ is cyclohexane-1,4-di-yl.

45. A method according to claim 41, wherein -$D^1$ is 4-methyl-cyclohexane-1,4-di-yl.

46. A method according to claim 42, wherein -$D^1$ is 4-methyl-cyclohexane-1,4-di-yl.

47. A method of treatment of rheumatoid arthritis in a patient in need of said treatment comprising administering to said patient a therapeutically effective amount of a compound selected from compounds of the following formulae, and pharmaceutically acceptable salts thereof:

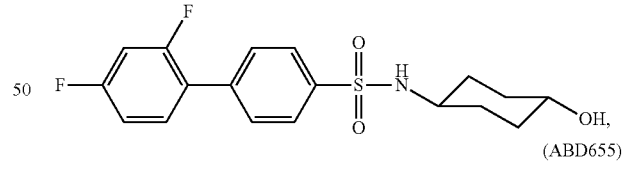
(ABD599)

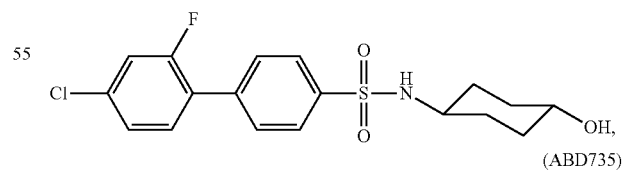
(ABD655)

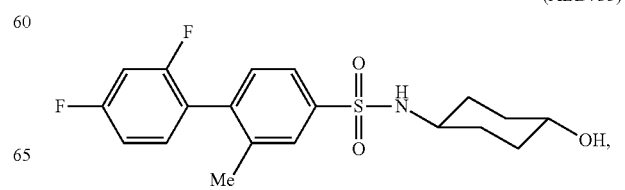
(ABD735)

-continued (ABD777)

(ABD836)

(ABD899)

and (ABD900)

48. A method according to claim 47, wherein the compound is a compound of the following formula, or a pharmaceutically acceptable salt thereof:

(ABD599)

49. A method according to claim 47, wherein the compound is a compound of the following formula, or a pharmaceutically acceptable salt thereof:

(ABD655)

50. A method according to claim 47, wherein the compound is a compound of the following formula, or a pharmaceutically acceptable salt thereof:

(ABD735)

51. A method according to claim 47, wherein the compound is a compound of the following formula, or a pharmaceutically acceptable salt thereof:

(ABD777)

52. A method according to claim 47, wherein the compound is a compound of the following formula, or a pharmaceutically acceptable salt thereof:

(ABD836)

53. A method according to claim 47, wherein the compound is a compound of the following formula, or a pharmaceutically acceptable salt thereof:

(ABD899)

54. A method according to claim 47, wherein the compound is a compound of the following formula, or a pharmaceutically acceptable salt thereof:

(ABD900)

* * * * *